US011474077B2

(12) United States Patent
Lal et al.

(10) Patent No.: US 11,474,077 B2
(45) Date of Patent: Oct. 18, 2022

(54) ACOUSTIC SENSING SYSTEMS, DEVICES AND METHODS

(71) Applicant: Cornell University, Ithaca, NY (US)

(72) Inventors: Amit Lal, Ithaca, NY (US); Mamdouh Abdelmejeed, Ithaca, NY (US); Justin Kuo, Ithaca, NY (US)

(73) Assignee: Cornell University, Ithaca, NY (US)

( * ) Notice: Subject to any disclaimer, the term of this patent is extended or adjusted under 35 U.S.C. 154(b) by 63 days.

(21) Appl. No.: 15/733,459

(22) PCT Filed: Feb. 4, 2019

(86) PCT No.: PCT/US2019/016564
§ 371 (c)(1),
(2) Date: Jul. 31, 2020

(87) PCT Pub. No.: WO2019/152961
PCT Pub. Date: Aug. 8, 2019

(65) Prior Publication Data
US 2021/0003534 A1    Jan. 7, 2021

Related U.S. Application Data

(60) Provisional application No. 62/625,887, filed on Feb. 2, 2018, provisional application No. 62/791,716, filed on Jan. 11, 2019.

(51) Int. Cl.
*G01K 11/22* (2006.01)
*G01N 29/24* (2006.01)
(Continued)

(52) U.S. Cl.
CPC ............. *G01N 29/07* (2013.01); *G01K 11/22* (2013.01); *G01N 29/2437* (2013.01);
(Continued)

(58) Field of Classification Search
CPC .... G01N 29/2437; G01N 33/24; G01N 29/07; G01N 2291/0231; G01N 2291/011;
(Continued)

(56) References Cited

U.S. PATENT DOCUMENTS 7,257,051 B2 * 8/2007 Thomenius .......... G01N 29/262
367/153
8,711,128 B2 * 4/2014 Small .................... G06F 3/0436
345/177
(Continued)

FOREIGN PATENT DOCUMENTS

WO    2014014968 A1    1/2014

OTHER PUBLICATIONS

Extended European Search Report, EP Application No. 19747141.0, dated Oct. 7, 2021, 10 pages.
(Continued)

*Primary Examiner* — Jacques M Saint Surin
(74) *Attorney, Agent, or Firm* — Perkins Coie LLP

(57) ABSTRACT

Disclosed are devices, systems and methods for touch, force and/or thermal sensing by an ultrasonic transceiver chip. In some aspects, an ultrasonic transceiver sensor device includes a semiconductor substrate; a CMOS layer attached to the substrate; an array of piezoelectric transducers coupled to the CMOS layer to generate ultrasonic pulses; and a contact layer attached to the substrate on a side opposite the substrate for providing a surface for contact with an object, where an ultrasonic pulse generated by a piezoelectric transducer propagates through the substrate and the contact layer, such that when the object is in contact with the surface of the contact layer, a reflected ultrasonic pulse is produced and propagates through the contact layer and the substrate to be received at the array of piezoelectric transducers, and the CMOS layer receive and process out-
(Continued)

puts from the piezoelectric transducers produced in response to the received reflected ultrasonic pulses.

25 Claims, 30 Drawing Sheets

(51) Int. Cl.
    *G01N 33/24*     (2006.01)
    *G10K 11/28*     (2006.01)
    *H05B 1/02*     (2006.01)
    *G01N 29/07*     (2006.01)

(52) U.S. Cl.
    CPC .............. *G01N 33/24* (2013.01); *G10K 11/28* (2013.01); *H05B 1/023* (2013.01); *G01N 2291/011* (2013.01); *G01N 2291/0231* (2013.01); *G01N 2291/02881* (2013.01); *G01N 2291/044* (2013.01); *G01N 2291/106* (2013.01)

(58) Field of Classification Search
    CPC ... G01N 2291/02881; G01N 2291/106; G01N 2291/044; G10K 11/28; G06F 3/0416; G06F 3/0436; G06F 21/32; G06F 3/04166; H05B 1/023; G01K 11/22; G06K 9/0002
    USPC .......................................................... 73/597
    See application file for complete search history.

(56) References Cited

U.S. PATENT DOCUMENTS

| | | | |
|---|---|---|---|
| 9,984,270 B2* | 5/2018 | Yousefpor | G06K 9/228 |
| 10,441,975 B2* | 10/2019 | Apte | B06B 1/0292 |
| 10,891,461 B2* | 1/2021 | Liu | G06K 9/2018 |
| 2007/0039745 A1 | 2/2007 | Anderson et al. | |
| 2008/0018199 A1 | 1/2008 | Trolier-McKinstry et al. | |
| 2010/0111133 A1 | 5/2010 | Yuhas et al. | |
| 2011/0073492 A1 | 3/2011 | Reich et al. | |
| 2012/0286847 A1 | 11/2012 | Peshkin et al. | |
| 2013/0099606 A1 | 4/2013 | Inoue et al. | |
| 2014/0198072 A1 | 7/2014 | Schuele et al. | |
| 2014/0355381 A1 | 12/2014 | Lal et al. | |
| 2015/0226699 A1 | 8/2015 | Li et al. | |
| 2017/0364726 A1 | 12/2017 | Buchan et al. | |
| 2021/0117756 A1 | 4/2021 | Lal et al. | |

OTHER PUBLICATIONS

Abdelmejeed, M. et al. "ALN GHz ultrasonic pulse diffraction based transmit-receive oscillator with 1 PPM stability," 2017 19th International Conference on Solid-State Sensors, Actuators and Microsystems (TRANSDUCERS), Kaohsiung, Taiwan, 2017, pp. 106-109.
Abdelmejeed, M. et al. "Diffraction Based Transmit-Receive Delay Element with Zero Temperature Coefficient" Solid-State Sensors, Actuators and Microsystems Workshop, Jun. 2016, pp. 102-105.
Abduljabar, A. "Real-Time Measurements of Size, Speed, and Dielectric Property of Liquid Segments Using a Microwave Microfluidic Sensor" Proc. IEEE MTT-S Int. Microw. Symp., Jun. 1-6, 2014, pp. 1-4.
Bourgeois, et al, "Design of resonators for the determination of the temperature coefficients of elastic constants of monocrystalline silicon," Frequency Control Symposium, 1997., Proceedings of the 1997 IEEE International, Orlando, FL, 1997, pp. 791.
Dorai, et al. Dynamic behavior analysis in compressed fingerprint videos. IEEE Transactions on Circuits and Systems for Video Technology, 14(1):58-73, Jan. 2004.
Emery, S. et al. "Soil mycorrhizal and nematode diversity vary in response to bioenergy crop identity and fertilization" GCB Bioenergy (2017) 9, 1644-1656.
Gao, Y. et al. "A global analysis of deforestation due to biofuel development" Working Paper 68, Center for International Forestry Research, 2011. 100 pages.
Gray, F. et al. "Biology and Management of the Sugar Beet Nematode" University of Wyoming, Agricultural Experiment Station, Department of Plant Sciences, College of Agriculture, Aug. 1997. B-975R. 7 pages.
Guerrini, F. "The Future of Agriculture? Smart Farming" Forbes, Feb. 18, 2015. Retrieved from https://www.forbes.com/sites/federicoguerrini/2015/02/18/the-future-of-agriculture-smart-farming/?sh=1 d7ed4a63c42.
Hafez, S. "Sugar Beet Nematodes in Idaho and Eastern Oregon" University of Idaho, College of Agriculture, Dec. 1998, 12 pages.
Hilnhutter, C. et al. "Use of imaging spectroscopy to discriminate symptoms caused by Heterodera schachtii and Rhizoctonia solani on sugar beet" Precision Agriculture, 2012, vol. 13, 17-32.
Hoople, J. et al, "Optimized response of AlN stack for chipscale GHz ultrasonics" 2015 IEEE International Ultrasonics Symposium (IUS) pp. 1-4 2015.
Hoople, J. et al. Chipscale GHz ultrasonic channels for fingerprint scanning. In 2015 IEEE International Ultrasonics Symposium (IUS), Oct. 21-24, 2015, p. 4 pp. , Piscataway, NJ, USA, 2015. IEEE.
Hoople, J. et al. Chip-scale reconfigurable phased-array sonic communication. In Ultrasonics Symposium (IUS), 2014 IEEE International, pp. 479-482, 2014.
Hoople, J. et al. Chip-scale sonic communication using AlN transducers. In Ultrasonics Symposium (IUS), 2013 IEEE International, pp. 1934-1937, 2013.
Jagdale, G. et al. "Sampling for Plant-Parasitic Nematodes Identification and Diagnosis" Department of Plant Pathology, University of Georgia (Revised Apr. 2011) 7 pages.
Joalland S. et al. "Aerial and Ground Based Sensing of Tolerance to Beet Cyst Nematode in Sugar Beet" Remote Sensing, 2018, vol. 10, No. 787, 21 pages.
Jones, F.G.W. "The soil as an environment for plant parasitic nematodes" Annals of Applied Biology, 1975, vol. 79, pp. 113-139.
Kim, R-H. et al. Flexible Electronics: Materials and Designs for Wirelessly Powered Implantable Light Emitting Systems, Small, 2012, vol. 8, No. 18, 2812-2818.
Kocar, G. et al. "An overview of biofuels from energy crops: Current status and future prospects" Renewable and Sustainable Energy Reviews, 28, (2013), 900-916.
Kuo J.C. et al. "64-Pixel solid state CMOS compatible ultrasonic fingerprint reader" 2017 IEEE 30th International Conference on MEMS pp. 9-12 2017.
Kuo, J. et al. Towards a CMOS compatible ultrasonic delay line memory. In 2015 IEEE International Ultrasonics Symposium (IUS), Oct. 21-24, 2015, p. 4 pp. , Piscataway, NJ, USA, 2015. IEEE.
Kuo, J. et al. Towards ultrasonic through-silicon vias (UTSV). In Ultrasonics Symposium (IUS), 2014 IEEE International, pp. 483-486, 2014.
Larmagnac, A. et al. "Stretchable electronics based on Ag-PDMS composites" Scientific Reports, 2014, 7 pages.
Leyssenne L. et al "Reconfigurable sensors for extraction of dielectric material and liquid properties," 2013 IEEE Radio Frequency Integrated Circuits Symposium (RFIC), Seattle, WA, 2013, pp. 393-396.
Lieberz, S. et al. "EU-27 Bio-Fuels Annual 2008" USDA Foreign Agricultural Service GAIN Report—E48063, May 30, 2008. 27 pages.
Mekete, T. et al. "Plant-Parasitic Nematodes Are Potential Pathogens of Miscanthus x giganteus and Panicum virgatum Used for Biofuels" Plant Disease, Apr. 2011, 413-418.
Melakeberhan, H. "Embracing the Emerging Precision Agriculture Technologies for Site-Specific Management of Yield-Limiting Factors," Journal of Nematology, 2002, vol. 34, No. 3, 185-188.
Olsson III, R. et al. Post-CMOS Compatible Aluminum Nitride MEMS Filters and Resonant Sensors. In 2007 IEEE International Frequency Control Symposium Joint with the 21st European Frequency and Time Forum, pp. 412-419. IEEE, May 2007.

(56) References Cited

OTHER PUBLICATIONS

Plant, R. "Site-specific management: the application of information technology to crop production" Computers and Electronics in Agriculture, 2001, vol. 30, 9-29.
Ruby, R. et al. Positioning FBAR technology in the frequency and timing domain. IEEE Transactions on Ultrasonics, Ferroelectrics and Frequency Control, 59(3):334-345, Mar. 2012.
Sosin, S. et al. Mesh Interconnects for Silicone Embedded Stretchable Silicon Electronics. In 2008 10th Electronics Packaging Technology Conference, pp. 230-235. IEEE, Dec. 2008.
Tang, S. et al. "Chapter 2: Basic Microfluidic and Soft Lithographic Techniques: 2-1 Introduction; 2-3 Materials for Fabricating Microfluidic Devices" Optofluidics: Fundamentals, Devices, and Applications; 2010; pp. 7-13.
Tylka, G. "Soybean Cyst Nematode" Iowa State University, Jan. 1994. Retrieved from: https://nematode.unl.edu/scn/scnisu.htm. 4 pages.
UC Davis, "Nematodes and Plant Damage" retrieved from http://nemaplex.ucdavis.edu/Plntpara/damage.htm [retrieved May 13, 2021]. 4 pages.
Ungar, E. et al. A New Approach to Defining Human Touch Temperature Standards. NASA, Jan. 2010. Retrieved from: https://ntrs.nasa.gov/citations/20100020960.
USDOE, "Corn Production and Portion Used for Fuel Ethanol" Alternative Fuels Data Center, May 2020. Retrieved from: https://afdc.energy.gov/data/10339. 1 page.
USDOE, "Monthly Biodeisel Production Report with data for Dec. 2020" Energy Information Administration, Feb. 2021. 10 pages.
UTCrops "How to take soil samples for nematode analysis from field crops" University of Tennessee Extention, Jan. 2021. Retrieved from https://utcrops.com/wp-content/uploads/2021/01/Nematode-Sampling-How-to-20121.pdf. 1 page.
Walker, G. "A guide to soil and crop sampling for nematodes" SARDI, retrieved from https://pir.sa.gov.au/_data/assets/pdf_file/0019/236233/sampling_for_nematodesA.pdf [Retrieved May 13, 2021] 3 pages.
Wang, W. et al, "Status assessment of polymeric materials in mineral oil under electro-thermal aging by frequency-domain dielectric spectroscopy," IEEE Trans. Dielectr. Electr. Insulator, vol. 22, No. 2, pp. 831-841, Apr. 2015.
Wrather, J. et al. "Estimates of Disease Effects on Soybean Yields in the United States 2003 to 2005" Journal of Nematology, Jun. 2006, vol. 28, No. 2, 173-180.
Zhang, N. et al. "Precision Agriculture—A Worldwide Overview" Computers and Electronics in Agriculture, 2002, vol. 36, 113-132.
ISA, International Search Report and Written Opinion for International Application No. PCT/US2019/016564, dated Jun. 18, 2019. 21 pages.
Abdelmejeed, M. et al. "Thermal Wavefront Imaging Using GHz Ultrasonics" 2017 IEEE International Ultrasonics Symposium.

\* cited by examiner

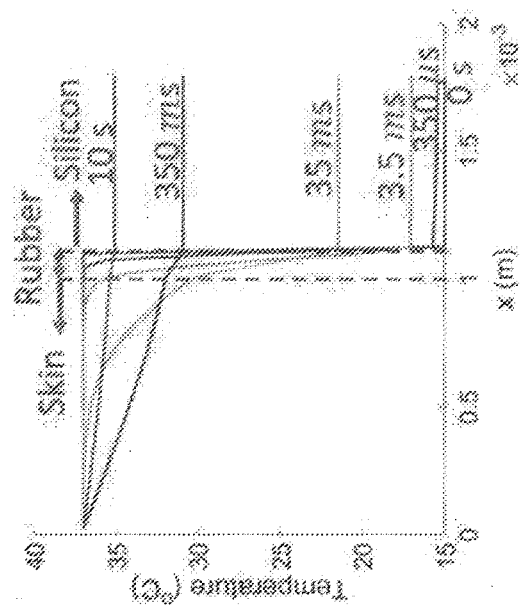
FIG. 10A
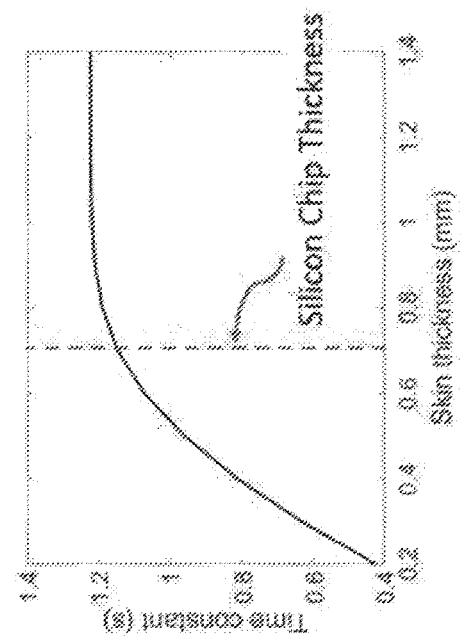
FIG. 10B
FIG. 10C
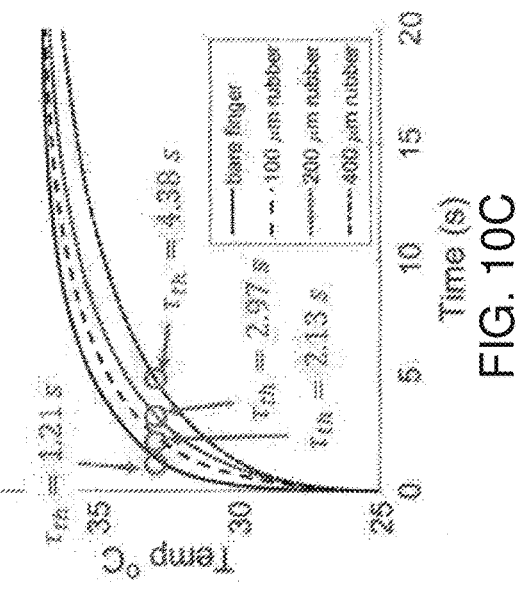
FIG. 10D

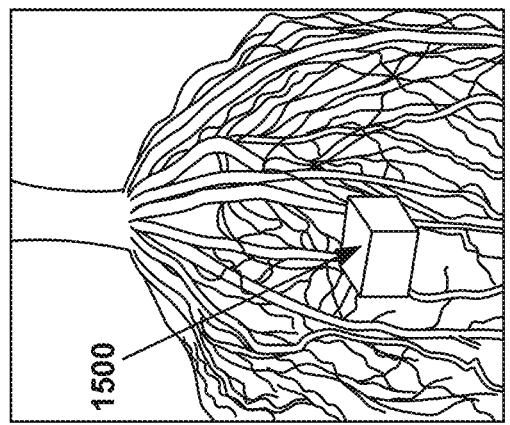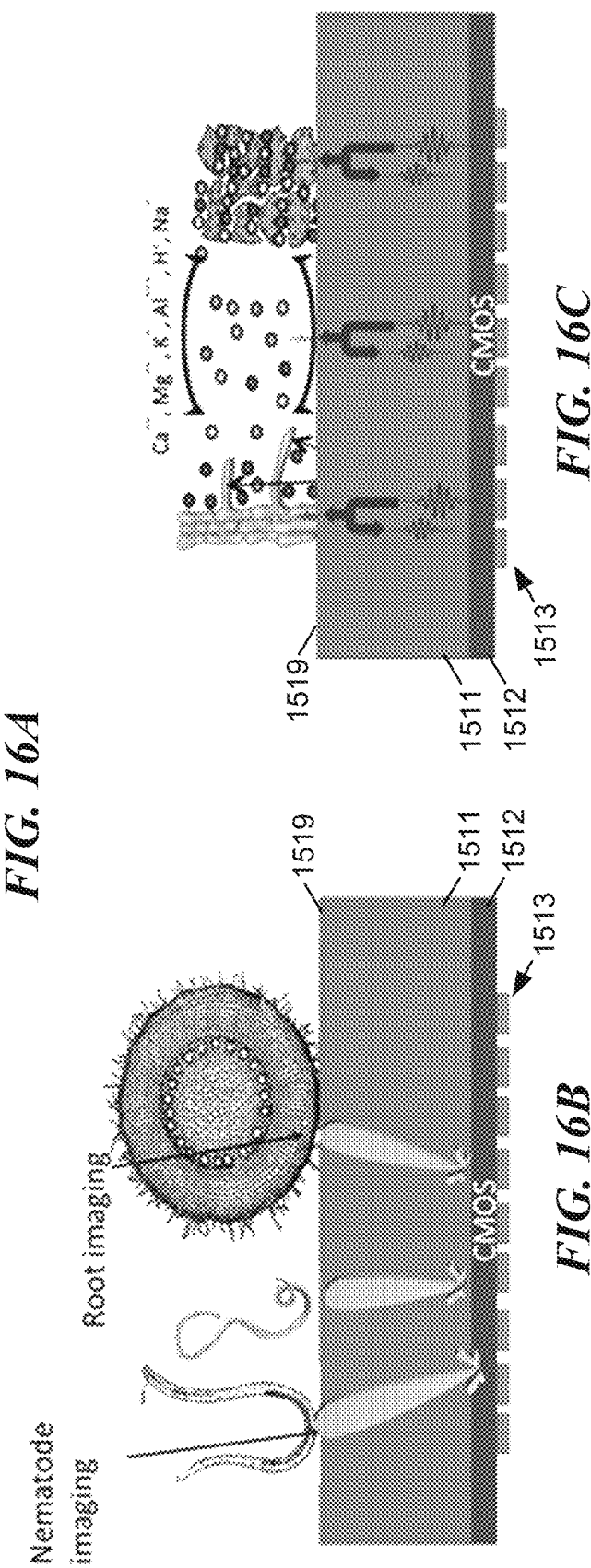
FIG. 16A
FIG. 16B
FIG. 16C

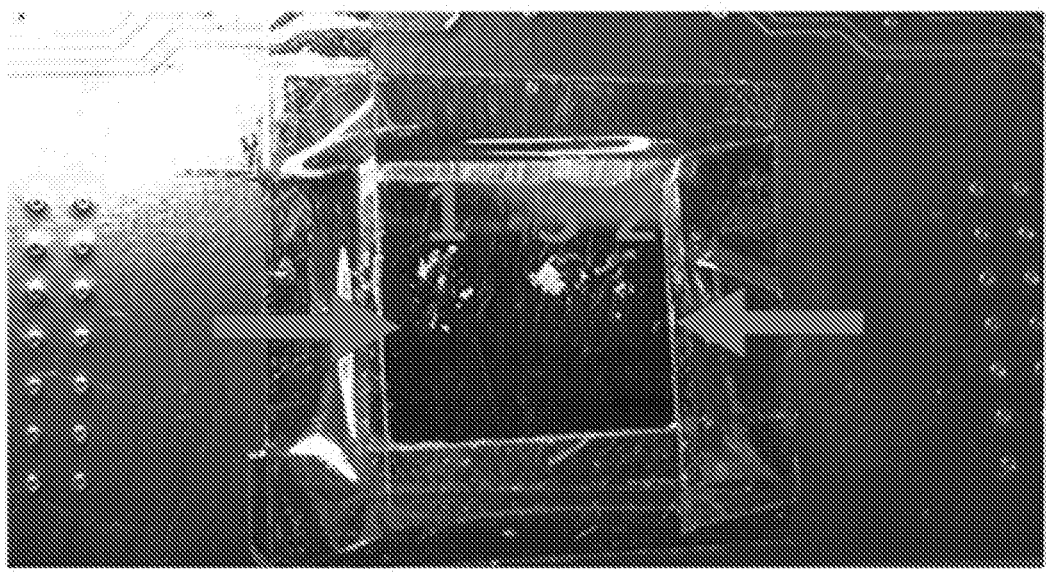
FIG. 19A
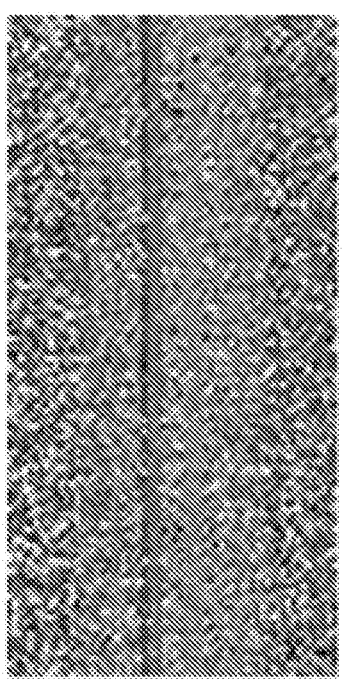 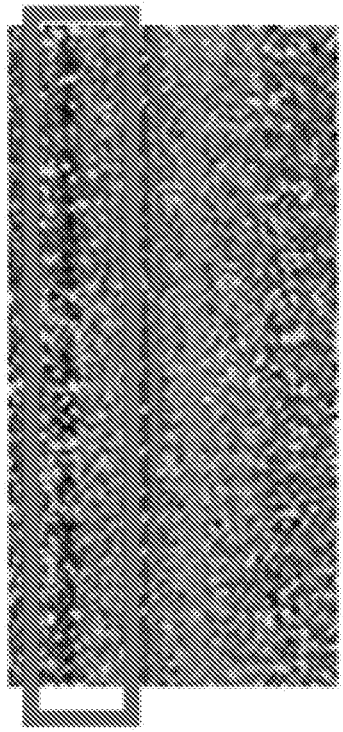 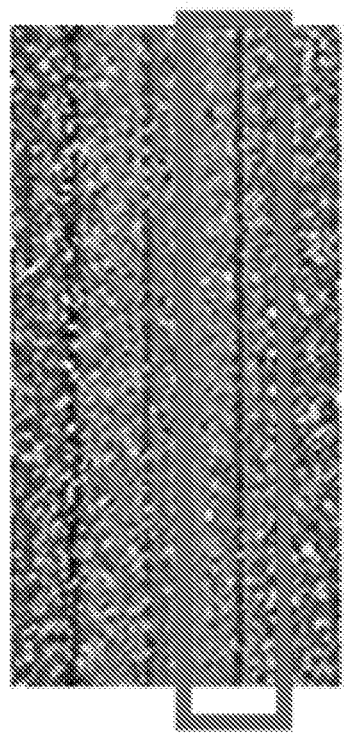
FIG. 19B      FIG. 19C      FIG. 19D

ACOUSTIC SENSING SYSTEMS, DEVICES AND METHODS

CROSS-REFERENCE TO RELATED APPLICATIONS

This patent document is a 371 National Phase Application of PCT Application No. PCT/US2019/016564 entitled "ACOUSTIC SENSING SYSTEMS, DEVICES AND METHODS" filed on Feb. 4, 2019 which claims priorities to and benefits of U.S. Provisional Patent Application No. 62/625,887, entitled "ACOUSTIC SENSING SYSTEMS, DEVICES AND METHODS" and filed on Feb. 2, 2018, and U.S. Provisional Patent Application No. 62/791,716, entitled "SOIL INTEGRATED GIGAHERTZ ULTRASONIC IMAGER DEVICES, SYSTEMS AND METHODS" and filed on Jan. 11, 2019. The entire contents of the aforementioned patent applications are incorporated by reference as part of the disclosure of this patent document.

TECHNICAL FIELD

This patent document relates to systems, devices and process for sensing surfaces and surface parameters using acoustic signals.

BACKGROUND

Any surface that has a topology can be sensed. One common example is for fingerprint sensing. Fingerprint sensing can be implemented by using different sensing technologies that capturing images of fingerprints, such as capacitive sensing of the valleys and ridges of a fingerprint, optical sensing based on optical imaging of the valleys and ridges of a fingerprint and ultrasound sensing based on different acoustic signals manifested by the valleys and ridges of a fingerprint.

SUMMARY

Disclosed are devices, systems and methods for touch, force and/or thermal sensing by an ultrasonic transceiver chip. In some aspects, the disclosed ultrasonic transceiver chip sensor device includes semiconductor integrated circuits having integrated in-chip acoustic communication links and nodes for a variety of uses including measuring surface properties of objects in contact with the device.

Also disclosed are soil integrated ultrasonic imager devices, systems and methods, which can be implemented for target water and pesticide delivery biomass production.

In some aspects, an ultrasonic transceiver sensor device includes a substrate including a semiconductor material; a CMOS layer attached to a first side of the substrate; an array of piezoelectric transducers coupled to the CMOS layer and operable to generate ultrasonic pulses having a frequency of at least 0.5 GHz; and a contact layer attached to a second side of the substrate opposite the first side to provide a surface for contact with an object, in which an ultrasonic pulse generated by a piezoelectric transducer of the array is directed to propagate through the substrate and the contact layer, such that when the object is in contact with the surface of the contact layer, a reflected ultrasonic pulse is produced and propagates through the contact layer and the substrate to be received at the array of piezoelectric transducers, in which CMOS elements of the CMOS layer in communication with the array of piezoelectric transducers are operable to receive and process outputs from the piezoelectric transducers produced in response to the received reflected ultrasonic pulses.

In some aspects, a sensing membrane for performing different sensing functions based on ultrasonic sensing includes a flexible base; an ultrasonic transceiver touch sensor coupled to the flexible base at a first location and configured to detect an object in contact with an exterior surface of the ultrasonic transceiver touch sensor based on transmitted ultrasonic signals at the surface and received reflected ultrasonic signals indicative of the object when the object is in contact to sense touch; an ultrasonic transceiver force sensor coupled to the flexible base at a second location and configured to detect a force applied by the object in contact with a ridge structure on an outer surface of the ultrasonic transceiver force sensor based on ultrasonic signals transmitted at the surface and returned ultrasonic signals received indicative of the applied force by the object to sense force; an ultrasonic transceiver temperature sensor coupled to the flexible base at a third location and configured to detect a thermal property of the object in contact with an external surface of the ultrasonic transceiver temperature sensor based on the relative time of flight of transmitted ultrasonic signals and received reflected ultrasonic signals from the surface when the object is in contact to sense temperature; and a bus in electrical communication with each of the ultrasonic transceiver touch sensor, ultrasonic transceiver force sensor, and ultrasonic transceiver temperature sensor, in which the sensing membrane is in communication with a data processing unit to regulate transmission of the ultrasonic signals of each respective ultrasonic transceiver sensor and process data associated with the transmitted and received ultrasonic signals by each respective ultrasonic transceiver sensor.

In some aspects, an ultrasonic sensor device for characterizing constituents in soil includes a housing including an opening; an ultrasonic transceiver sensor device contained in the housing, in which the ultrasonic transceiver sensor device includes a substrate including a semiconductor material, a CMOS layer attached to a first side of the substrate, an array of piezoelectric transducers coupled to the CMOS layer and operable to generate ultrasonic pulses having a frequency in a range of 0.5 GHz or less, and a contact layer attached to a second side of the substrate opposite the first side, in which the ultrasonic transceiver sensor device is contained in the housing to position the contact layer at the opening to provide an exposed surface of the contact layer for contacting with soil or an object in the soil, in which the ultrasonic transceiver sensor device is operable to generate an ultrasonic pulse by a piezoelectric transducer of the array that is directed to propagate through the substrate and the contact layer to the surface in contact with the soil or the object in the soil, such that a reflected ultrasonic pulse is produced at the surface that propagates through the contact layer and the substrate to be received at the array of piezoelectric transducers, in which CMOS elements of the CMOS layer in communication with the array of piezoelectric transducers are operable to receive and process outputs from the piezoelectric transducers produced in response to the received reflected ultrasonic pulses; and a data processing and communications unit including a signal processing circuit, a power unit, and a wireless transmitter and/or receiver unit.

Example implementations including one or more of the following features. In some implementations, the ultrasonic transceiver chip can measure temperature of an object in contact through thermal sensing by using different thermal impedance values due to the contact quality of the object. In some implementations, the ultrasonic transceiver chip includes a receive-transmit pixel array-based sensor that operates at GHz frequencies to image the surface of an object in contact with the chip, including force sensing and thermal sensing. For example, the force applied to the sensor leads to increase in sizes and density of features that can be used to quantify the force. The temperature profile of the bulk semiconductor material can be imaged by the change of speed of sound in the sensor chip via heat transfer across the surface into or out of the semiconductor bulk. For example, the rate of Time-Of-Flight (TOF) change and the TOF final values can be used to measure the thermal properties of the object being touched. Example applications of the ultrasonic transceiver chip can include use in medical devices for detection of heart rate, skin temperature, skin dryness, and surface thermal conductivity. Also, example applications of the ultrasonic transceiver chip can include use in robot human-machine interfaces, such as synthetic membrane for a target object, like a robot or a wearable device.

The subject matter described in this patent document can be implemented in specific ways that provide one or more of the following features.

BRIEF DESCRIPTION OF THE DRAWINGS

FIGS. 10A and 10B show data plots depicting the temperature profile across a distance at different times for bare finger and finger with rubber gloves, respectively.

FIG. 10C shows a data plot depicting the transient temperature of silicon across time.

FIG. 10D shows a data plot depicting thermal time constants for different skin thicknesses.

FIGS. 16A-16C show diagrams illustrating an example ultrasonic sensor that can be placed in soil and monitor plant growth and soil conditions.

FIGS. 19A-19D show images of the three samples of nematode globules on the sensing area of the example ultrasonic imager device and the ultrasonic images acquired.

DETAILED DESCRIPTION

Ultrasonic waves can be used for imaging and other sensing applications. The technology disclosed in this patent document can be used to apply ultrasonic sensing to new sensing devices, systems and applications, including using ultrasound for sensing a touch or touch force associated with the touch, or sensing of a temperature or a change in temperature of an object. In some implementations, the disclosed technology for ultrasonic sensing can be used to construct a sensing system with different ultrasound sensing modules to perform different types of sensing operations, e.g., as a robotic hand which may emulate certain sensing functions of a human hand.

There have been recent developments in the integration of ultrasonic capabilities with semiconductor devices. Silicon-based and other semiconductor integrated circuit (IC) chips typically use conductive wires for in-chip communication links, which can have several limitations in IC chip designs including spot heating, thermal cycling degradation of components, signal interference, among others. Ultrasonic transducers as communication transceivers can provide wireless ultrasonic communication interconnects between different circuit elements without hardwiring between circuit elements and as built-in circuit sensors for sensing circuit conditions, and thereby significantly reduce the metal interconnects between circuit elements.

FIGS. 1A-1D show diagrams of example GHz ultrasonic transducers made of thin-film piezoelectric aluminum nitride (AlN) material, which can be post-fabricated onto CMOS wafers to provide phased arrays of GHz sonic energy. As shown in the example, CMOS circuitry can be integrated with piezoelectric pixels that drive GHz acoustic signals for communicative purposes. The example device provides a high fT of CMOS. The wavelength of ultrasonic waves at 1 GHz is 9 µm, which can become progressively smaller at higher frequencies. Pulse trains of 10-1-5 wavelengths are ≈90 µm, which is smaller than the silicon wafer thickness, allowing pulse-packets to bounce from the backside of the silicon and scatter before the next packet arrives.

Examples of acoustic transmission in semiconductor integrated circuit (IC) chips are described in U.S. Patent Publication No. 2014/0355381A1, which is incorporated by reference as part of the disclosure of this patent document.

Figure 1A:
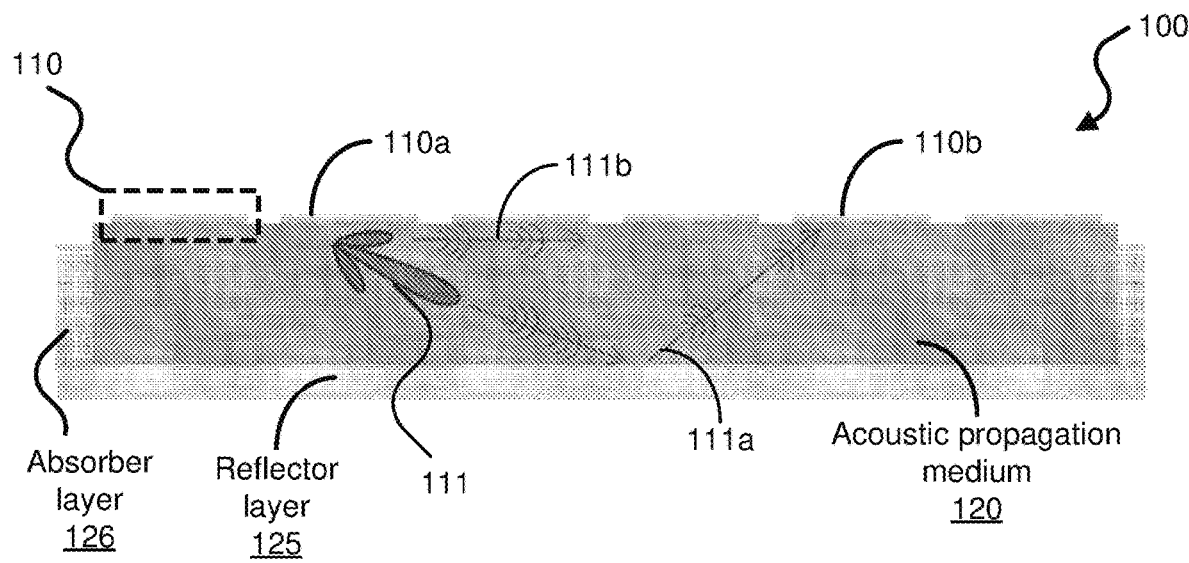
FIGS. 1A-1D show diagrams of example GHz ultrasonic transducer device integrated with CMOS circuitry.

FIG. 1A shows a schematic illustration of an example chip-scale wireless communications IC device 100 that includes an array of acoustic transceiver (sonar) modules 110 capable of transmitting and receiving acoustic communications signals. The device 100 is structured to include a substrate 120 to provide a base for the array of sonar modules 110 and formed of a solid state semiconductor material capable of propagating acoustic energy (e.g., ultrasound signal) within the device 100, e.g., including between sonar modules 110 of the array. In some examples, the sonar modules 110 can be configured as thin films of aluminum nitride (AlN) and/or lead zirconium titanate (PZT) on top of a metallization layer. In some examples, the acoustic propagation medium 120 can include silicon, e.g., such as the silicon material of a silicon die. Each or any of the sonar modules 110 can be structured to include a sub-array of individual piezoelectric transducer elements 130 (shown in FIG. 1B), e.g., sometimes referred to herein as pixel elements or pixels. The sub-array of individual piezoelectric transducer elements 130 is communicatively linked to underlying electronic control circuits (shown in FIG. 1B as control circuit layer 132). The electronic control circuits include driving circuits for providing the driving signals that the transducer elements 130 transduce to produce the acoustic communication signals and logic circuits to process received acoustic communication signals transduced by the transducer elements 130.

In the example shown in FIG. 1A, the device 100 further includes an acoustic reflector/mismatching layer 125 capable of reflecting or refracting the intra-device ultrasound signal, e.g., which can be used to steer the ultrasound communication signal from one or more sonar modules 110 to another one or more sonar modules 110. For example, the acoustic reflector layer 125 is configured under the acoustic propagation medium substrate 120, as shown in FIG. 1A, and/or be configured along one or more sides of the substrate 120. In the example shown in FIG. 1A, the device 100 further includes an acoustic absorber layer 126 to absorb the intra-device ultrasound signal, e.g., preventing the ultrasound communication signal from transmission beyond the device 100. In the example shown in FIG. 1A, the acoustic absorber layer 126 is configured along the sides of the acoustic propagation medium substrate 120.

Figure 1B:
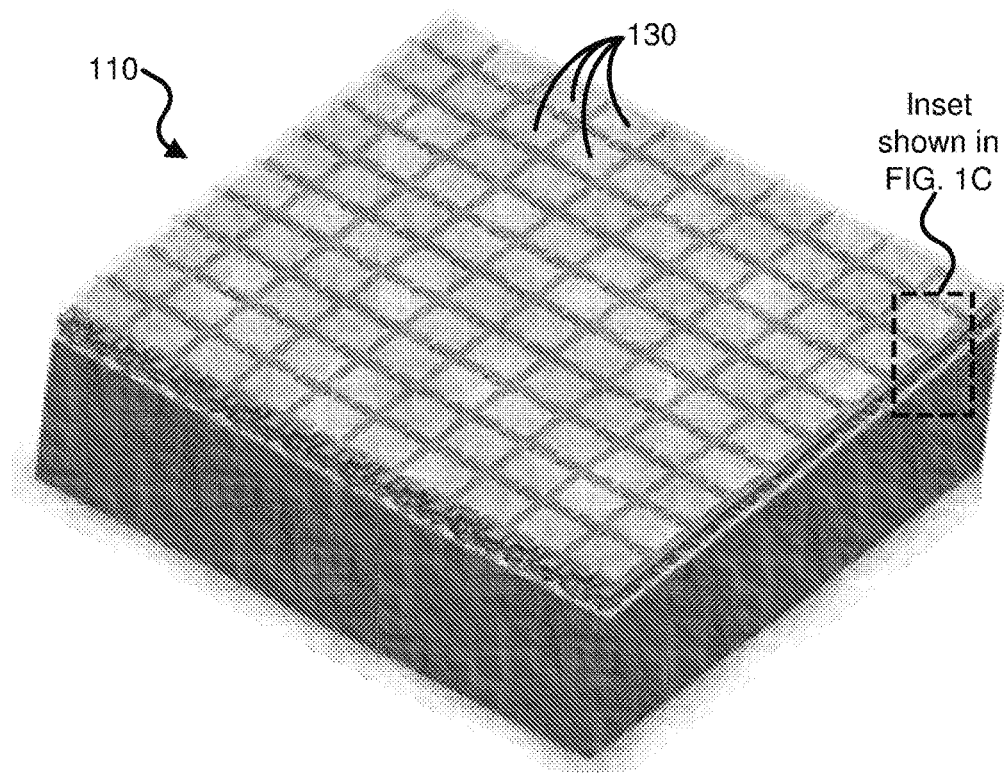

As shown in FIG. 1B, the piezoelectric transducer elements 130 of the sonar modules 110 can be configured with uniform or periodic spacing in the pixel array, e.g., including $\lambda/2$ spacing. For example, since each piezoelectric transducer element 130 of the sub-array (of a sonar module 110) is a fraction of a wavelength in lateral dimensions, relatively small phased arrays for sonar transmit and receive blocks can be implemented. In some embodiments of the device 100, for example, each sonar module 110 can include 10-20 pixels which are placed approximately one-half of an acoustic wave wavelength apart. In one example, each pixel can be configured to a size in a range of 3-10 µm, such that each sonar module 110 includes a planar size of ~100×100 µm, e.g., which is about the size of a contact pad on a CMOS chip. Also, for example, the acoustic propagation medium substrate 120 can be configured to a height of 750 µm (or 84λ in this example).

Figure 1C:
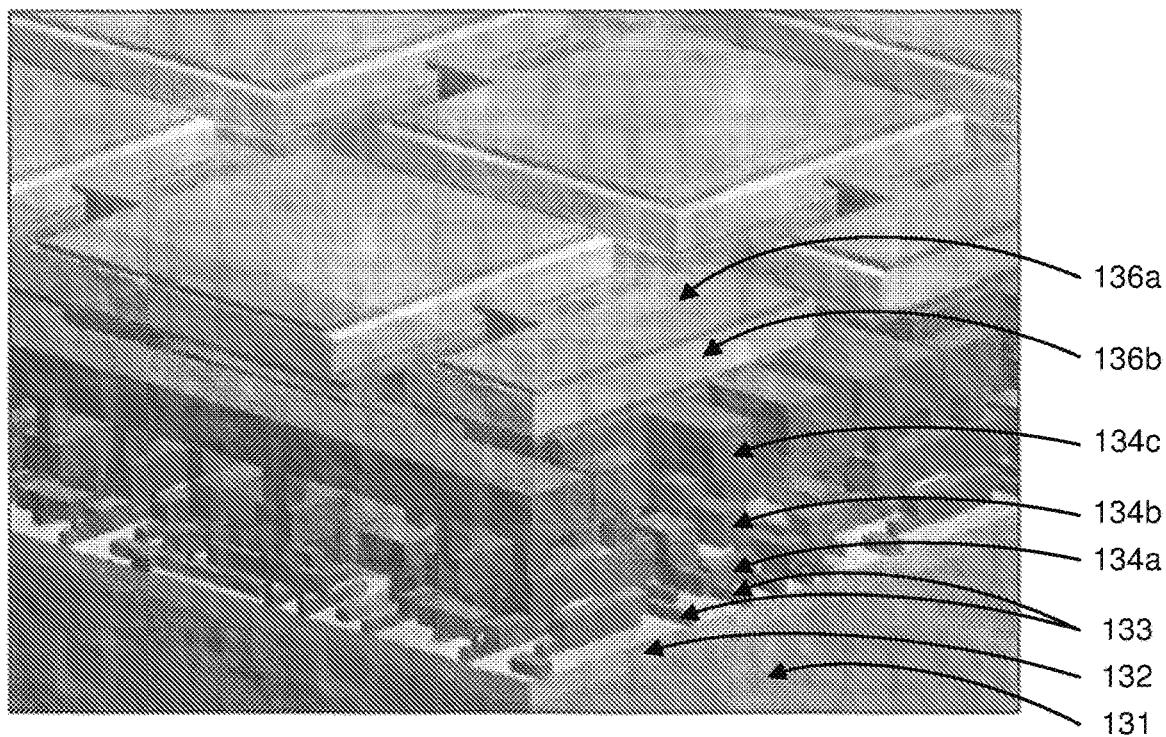
Figure 1D:
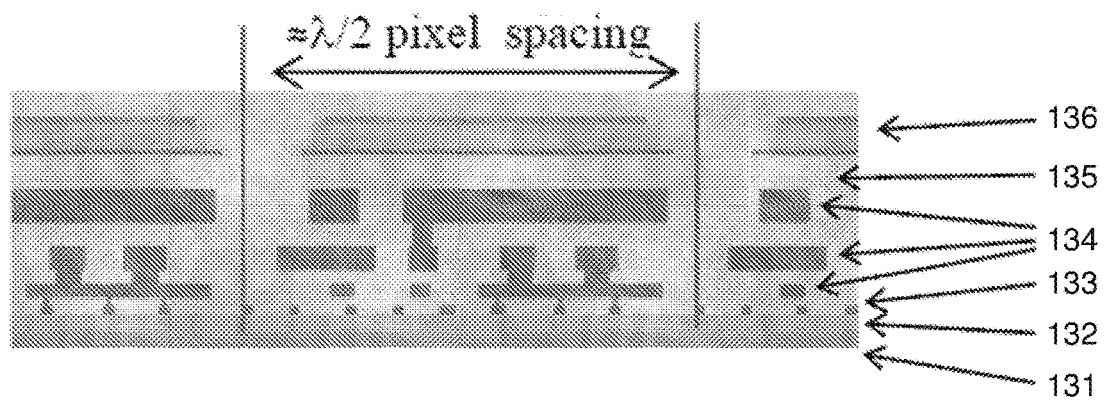

FIGS. 1C and 1D show inset schematics from FIG. 1B showing the piezoelectric transducer element 130 of the device 100 in a three-dimensional view and a cross-sectional view, respectively, over a control circuit layer 132 and the substrate 120. In the example, the acoustic propagation medium material of the substrate 120 includes a bulk material 131 (e.g., Silicon). In some examples, the control circuit layer 132 can include one or more CMOS active layers 132 that includes individual control circuit blocks corresponding to the individual piezoelectric transducer elements 130 of the sub-array, e.g. in which the control circuits can include one or more driving circuits, read circuits, and logic circuits including digital logic, analog logic and/or amplifiers, which are formed on the bulk Silicon layer 131. A first metal layer 133 can be formed over the one or more CMOS active layers 132. For example, the bulk Silicon substrate 131, the CMOS active layers 132, and the first metal layer 133 form a FEOL (front-end-of-line) region of the device 100. The transducer element 130 can include more metal layers, e.g., including a second, a third, and a fourth metal layers 134a, 134b, and 134c, respectively, as shown in FIGS. 1C and 1D. The transducer element 130 can include an electrode structure layer 136b, upon which, a piezoelectric material (e.g., AlN) layer 136a is formed. The transducer element 130 can include an intermetal dielectric material 135 that is formed between the metal layers 134a, 134b, and 134c, and over the FEOL region. For example, the metal layers 134a, 134b, and 134c, the electrode structure layer 136b, the intermetal dielectric material 135, and the piezoelectric material layer 136a form a BEOL (back-end-of-line) region of the device 100. For example, the metal layer structures 133, 134a, 134b, and/or 134c can function both as interconnect layer(s) for electronics and as custom designed acoustic wave guiding, channeling, or scattering structures.

Beam width of an ultrasonic pulse scales as the wavelength of ultrasound in the micron (m) range allowing focusing with phased array approaches. The wavelength allows an array of λ/2 pixel arrays to be formed in a small chip space. These arrays can be formed on CMOS wafers, e.g., owing to the low temperature processing. For example, AlN thin films can be used in many commercial devices including piezoelectric RF FBAR filters. Established foundries are able to produce CMOS with AlN transducers on the top-most layer.

In implementations, the CMOS compatible voltage typically includes the strain generated across a transducer is $\varepsilon = d_{33} V/t_{AlN}$, where $d_{33}$ is the piezoelectric coefficient. For example, the thickness of the AlN film is approximately equal to half wavelength $$\left(\frac{\lambda}{2} = \frac{c_{AlN}}{2f}\right)$$

at the center ultrasonic frequency. In the terms of the frequency f, one can represent the strain as $$\varepsilon = d_{33} \frac{V2f}{c_{AlN}}.$$

As is apparent from this expression, as frequency is increased, the voltage V can be reduced for keeping the excited strain the same across frequency. For example, 1 to 3 $V_{peak}$ can be used in acoustic communications, through silicon vias (TSV), and fingerprint imaging implementations using ultrasonic transducer devices like the example shown in FIGS. 1A-1D.

In some implementations, like that shown in FIG. 1D, the electronics that drive the transducers can be integrated within the pixel area, to realize a highly integrated transducer/electronics subsystem. As the transistor sizes shrink at advanced CMOS nodes decreasing circuit sizes quadratically, the GHz ultrasonic wavelength scales inversely with frequency. The transducer electronics can be placed within the same area as one pixel. For example, the silicon wafer itself has an ultralow loss of 0.01 dB/mm for nearly loss-less pulse-packet traversal. The top CMOS layer including the metal stack is typically 9-10 μm thick, which is on the same size scale as sonic wavelength. Since the transducers are intimately in contact with the top metal and transistor stack, any effect of diffraction due to metal and oxide fine structures due to the circuits placed on the top is averaged out in the far-field.

The framework for gigahertz (GHz) ultrasonics integrated with CMOS can be employed to produce various types of ultrasonic transducer devices. In one example, a 200 Mbit/s on-chip sonic communication can be implemented, e.g., including phasing of four pixels to communicate to one of the four other pixels. For example, ultrasonic through-silicon vias can be implemented, which can be used for bonded silicon chips, each with its own set of AlN pixels, and including data links up to 200 MBits/second across the two chips. Also, for example, ultrasonic delay line memory can be implemented, e.g., based on recirculating ultrasonic pulses being a stored bit. Furthermore, many transducers can be driven at different amplitude and phases to forms an ultrasonic beam in a programmable direction.

FIGS. 2A-2D show diagrams and plots of an example embodiment and implementations of an ultrasonic fingerprint sensor device, labeled 200. In this device, ultrasonic pulses are launched into an example substrate (e.g., silicon substrate). The pulses travel to the opposite side of the chip and reflect from the backside because of the large impedance mismatch between the silicon and the material of the object touching the silicon. The reflected signal is different depending on how much energy is lost into the touching material. This approach allows the transducer side to be electrically remote from the transducer side. The reflected signals come back to the top set of electrode to be transduced back into electrical signal that can be measured using electronic circuitry.

The ultrasonic fingerprint sensor device 200 represents one class or application of ultrasonic transducer devices. Implementations of the example ultrasonic fingerprint sensor 200 demonstrated less than 20 μm resolution in obtaining fingerprint patterns when touching the backside of the sensor chip. The example ultrasonic fingerprint sensor 200 used in the implementations included a 64-AlN pixel array, operating at 1.3 GHz to measure the reflected signal amplitude to identify ridges and valleys of a user's finger to produce a fingerprint image.

Figure 2A:
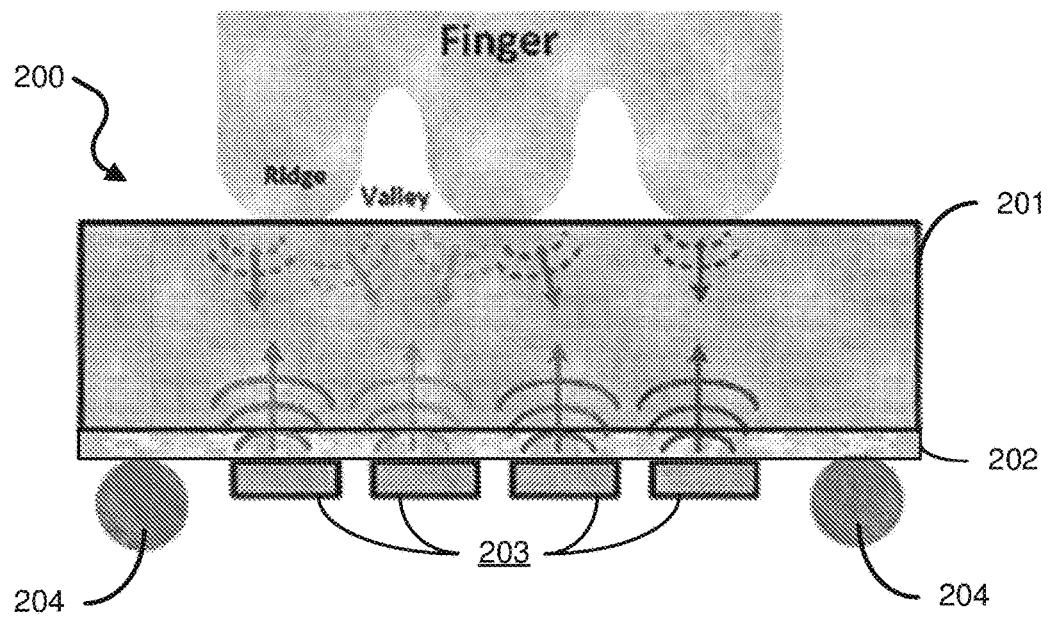
FIGS. 2A-2D show diagrams and plots of an example ultrasonic fingerprint sensor device.

FIG. 2A shows a diagram of the example ultrasonic fingerprint sensor 200, in which a finger having ridges and valleys are placed on the backside of the sensor chip. The ultrasonic fingerprint sensor device 200 includes a bulk semiconductor substrate 201, e.g., silicon coupled to a stack of CMOS layers 202 patterned to form circuit elements, which can include transistors. The device 200 includes an array of ultrasound transducers 203 (e.g., AlN transducer elements) coupled to the stack of CMOS layers 202. For example, the array of ultrasound transducers 203 can be coupled to an individual circuit element of the stack of CMOS layers 202 or to portions of the stack of CMOS layers 202 that include two or more circuit elements. In implementations, one or more ultrasound transducers 203 are configured to generate an ultrasound signal that contains information to communicate with one or more other ultrasound transducers 203 in the array and to receive ultrasound signals from one or more other ultrasound transducers 203. The one or more ultrasound transducers 203 act as communication nodes for the circuit element or block of circuit elements to acoustically communicate with other circuit elements or blocks of circuit elements in the device 200, thereby providing an ultrasound communication network of ultrasonic communication links without physical wiring between the circuit elements of the stack of CMOS layers 202. The ultrasonic fingerprint sensor device 200 includes electrical connections 204 coupled at regions of the CMOS stack 202 to send and receive data from the circuit elements and blocks of the stack of CMOS layers 202.

Figure 2B:
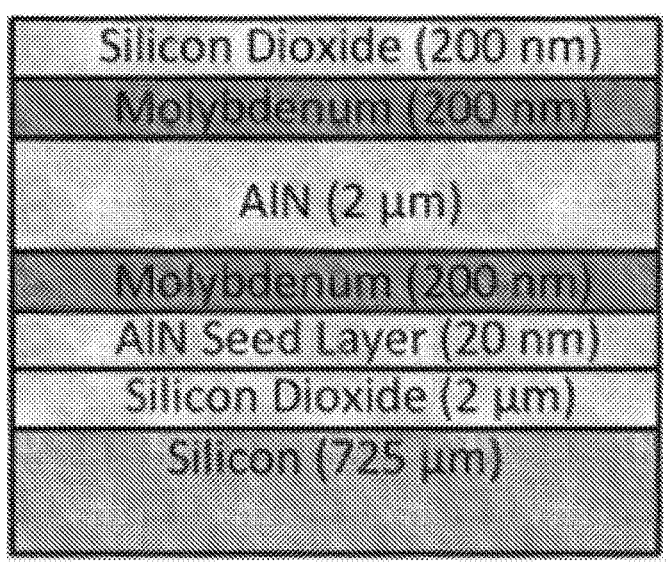
Figure 2B:
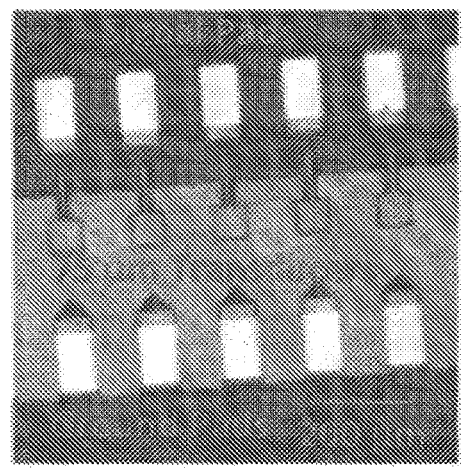

FIG. 2B shows diagrams depicting an example linear array of AlN transducers of the device 200 (right diagram) and an example thin film stack (left diagram) to produce the transducer elements, including electrodes and a piezoelectric material. In this example, the thin film stack includes piezoelectric material aluminum nitride formed between molybdenum and silicon dioxide layers, which is coupled to silicon on one side.

Figure 2C:
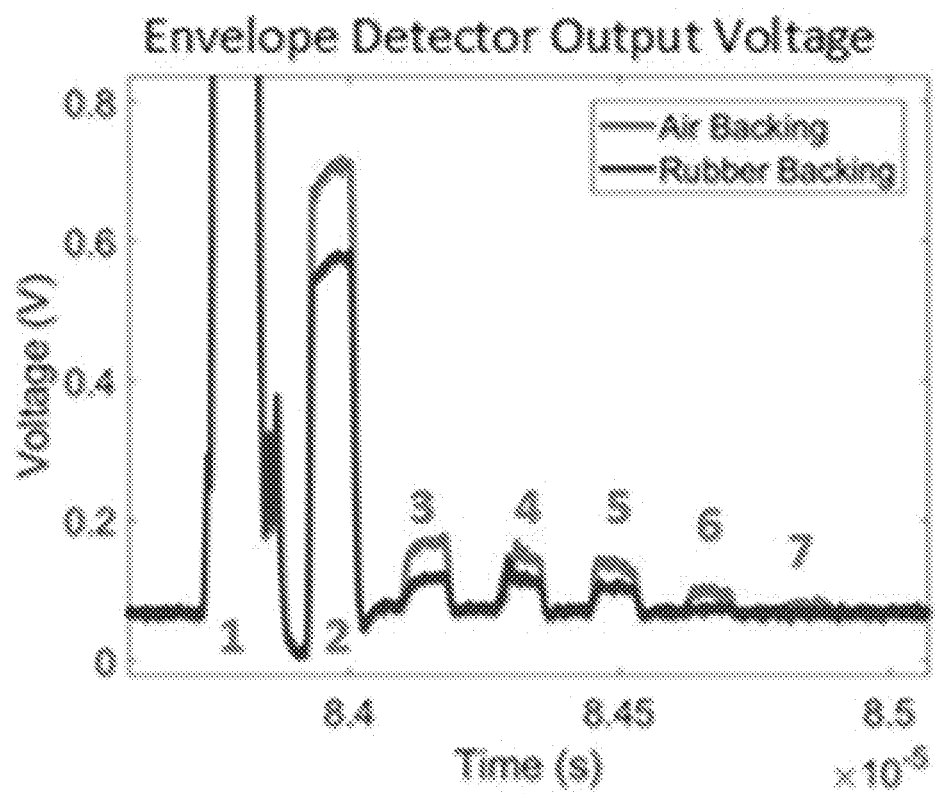

FIG. 2C shows a data plot depicting multiple reflections of pulses used to measure ridges and valleys, e.g., using two types of backing, i.e., air backing and rubber backing. The data shows that reflected signal is lower when a finger ridge is touching the backside, as compared to when only air is on the backside.

Figure 2D:
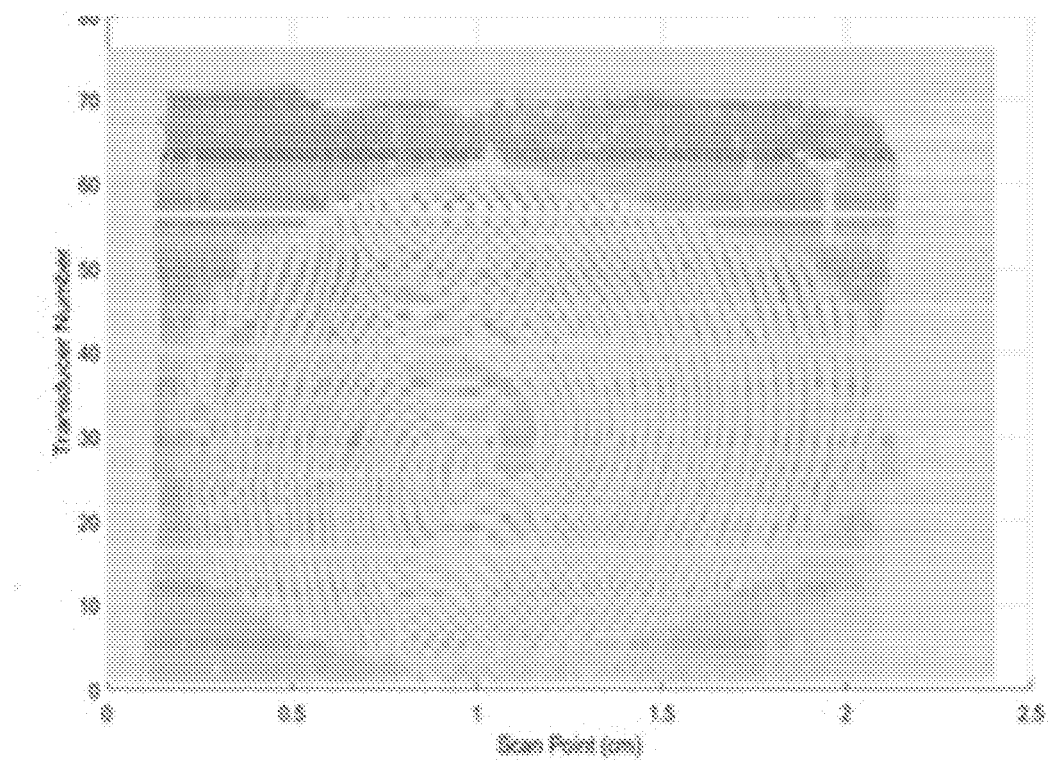

FIG. 2D shows an image of an example fingerprint imaged by the example ultrasonic fingerprint sensor of FIG. 2A. It is noted in this example image that a few pixels were not working.

Along with the advancements in fingerprint sensing by GHz ultrasonic transducer-based devices, new challenges become present. While the example ultrasonic fingerprint sensor 200 demonstrates the capability of detecting a fingerprint and reconstructing an image of the fingerprint (e.g., FIG. 2D), there are constraints on what further information may be obtained. For example, it would be advantageous to, in addition to detecting the presence of an object in contact with an ultrasonic transducer device, extract and characterize information about the contact with the object and the object itself—such as how much force or pressure the object is exerting on the ultrasonic transducer device, how hard or soft is the surface of the contacting object, and what temperature is the object in contact with the device?

Technical challenges to achieve touch sensors of force and temperature, like that of living skin, are objects of the disclosed systems, devices and methods, e.g., using the described GHz pixel transmit/receive function. For instance, in current designs of ultrasonic sensors, there are two variables that can be measured, the return amplitude at different receive pixels and the time of flight of different pulses. Using these variables, it can be challenging if not impossible to ascertain shear forces and normal forces applied on the device 200 used as a touch sensor.

In the context of robotic touch sensors, it is desirable to also know what the robot is touching and informative factors about the object being touched, beyond just that it is touching something. The return amplitude is a function of the acoustic impedance of what is being touched, but may not provide sufficient differentiation between two kinds of wood, for example. Hence, measurement of other variables, such as the thermal conductance of the material would provide additional axis of information to differentiate materials. In order to differentiate the material properties and temperature, some of the transducers have to be made to have a controlled temperature dependence.

Disclosed are devices, systems and methods for touch, force and/or thermal sensing by an ultrasonic transceiver chip. In some aspects, an ultrasonic transceiver chip sensor device includes semiconductor integrated circuits having integrated in-chip acoustic communication links and nodes for use measuring surface properties of objects in contact with the device analogous to touch, e.g., providing an artificial skin that can be integrated with other types of devices, such as robotic systems.

Figure 3A:
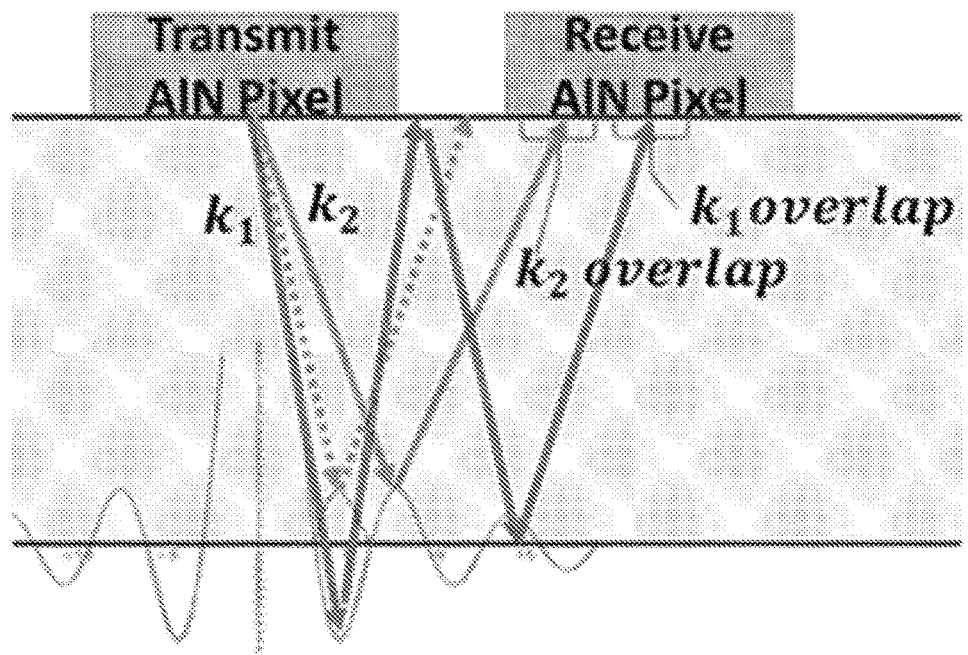
FIGS. 3A and 3B show a diagram and data plot depicting transmissions of example piezoelectric pixels of an array with a stable oscillator clock.
Figure 3B:
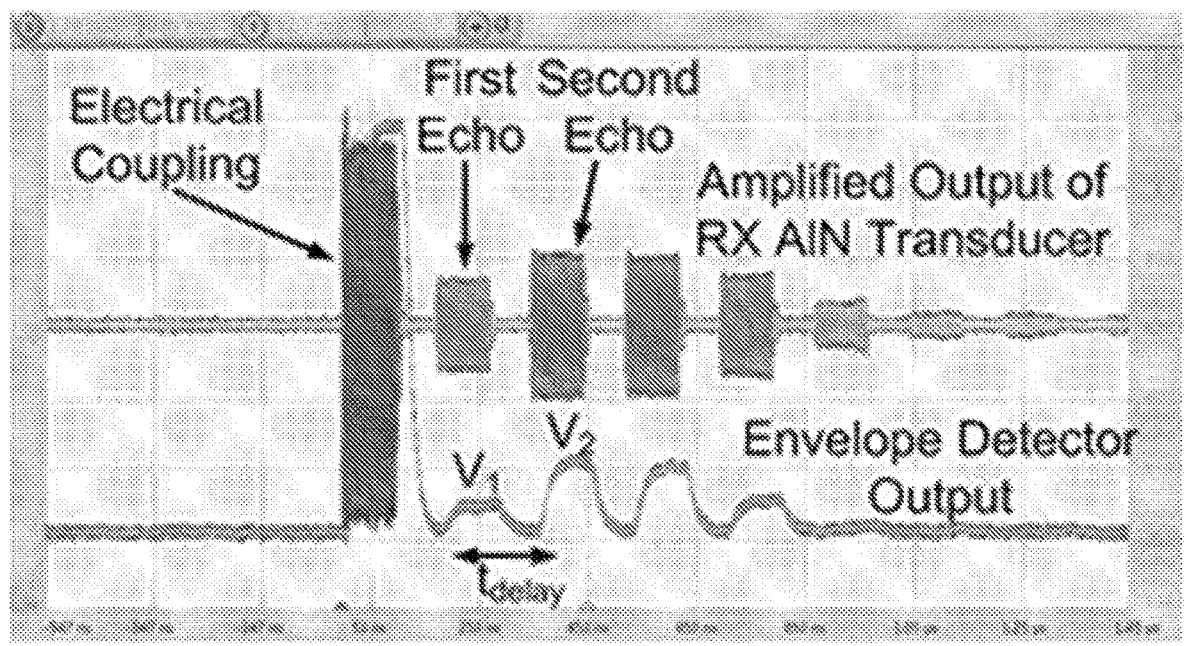

FIGS. 3A and 3B show a diagram and data plot depicting transmissions of example piezoelectric pixels of an array with a stable oscillator clock. In these example implementations, a stable oscillator clock (e.g., less than 5 ppm) integrated based on the delay of sonic pulses transmitted and received across the chip can be employed. FIG. 3A shows a diagram of example AlN pixels that transmit Gigahertz Ultrasonic Pulses (GUPs) that bounce off the back side of a device (e.g., silicon chip) to be received on the top. The time of flight of the pulse can be measured for multiple reflections received at multiple receivers. FIG. 3B shows a plot depicting multiple reflections that can be measured with 10-100 mV amplitudes.

As shown in FIG. 3A, the initial pulse released undergoes the process of diffraction such that multiple peaks in different directions with different angles emanate from the transducer. These different angles correspond to k-vectors k1 and k2, for example. As shown in FIG. 3B, the pulses with the smallest angle from the normal to the transducer can undergo multiple bounces before it is received at the receive pixel. The pulse with a larger angle reaches the receiver with one bounce arriving at the receiver earlier than the smaller angle pulse. Because the amplitude of the $2^{nd}$ order k-vector (k2) is lower and the first order k-vector (k1) is larger in amplitude, the first received pulse is lower in amplitude compared to the second received pulse. Other reflections, corresponding to the diffraction of the first return pulses normal to the transmit transducer, are also measured. The time of flight difference between the first and second received pulses can be very stable and used to form a stable delay to form oscillators.

Figure 3C:
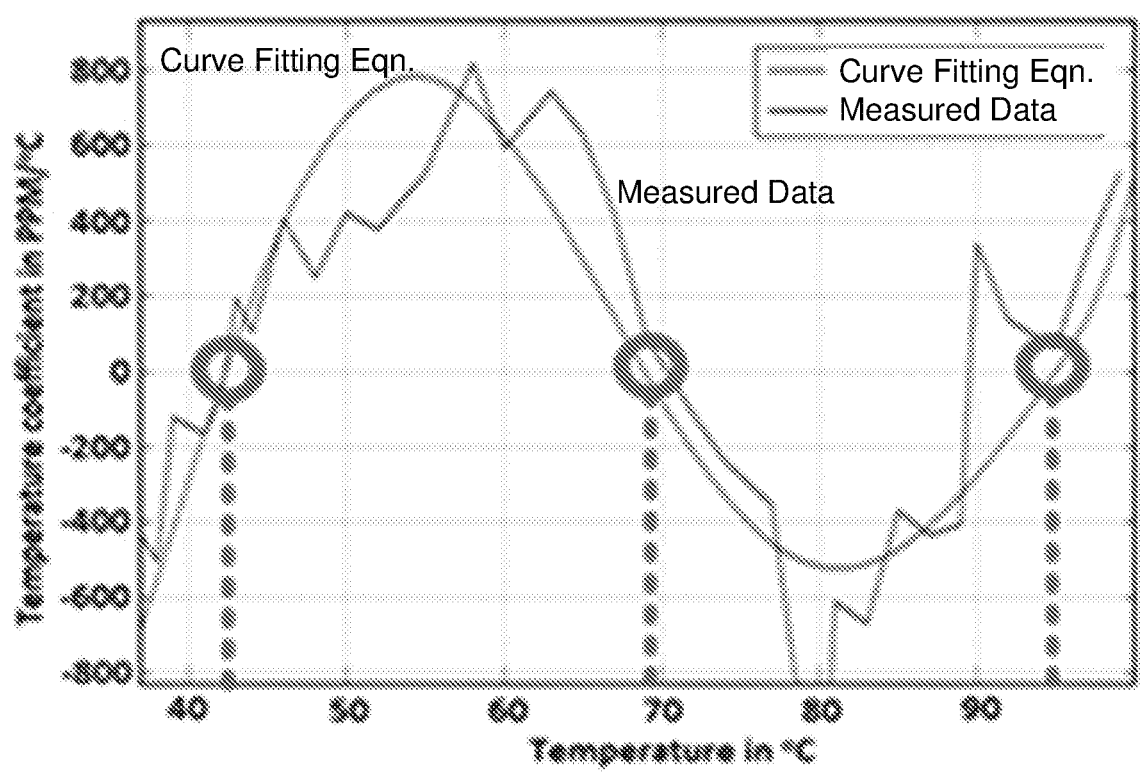
FIG. 3C shows a data plot depicting the temperature dependence of the time-of-flight delay for an ultrasonic transducer device.

FIG. 3C shows a data plot depicting the temperature dependence of the time-of-flight delay for an ultrasonic transducer device. FIG. 3C shows the temperature dependence of the time-of-flight delay, showing temperatures at which the measured temperature coefficient of the delay is zero. For example, this complex behavior of the delay temperature coefficient can be due to the combination of the slowing of the speed of sound in silicon, and effect on temperature on comparators used to trigger upon the arriving pulse. These effects can be tailored to quantify the temperature and thermal conductivity of the contacted surface.

Figure 4A:
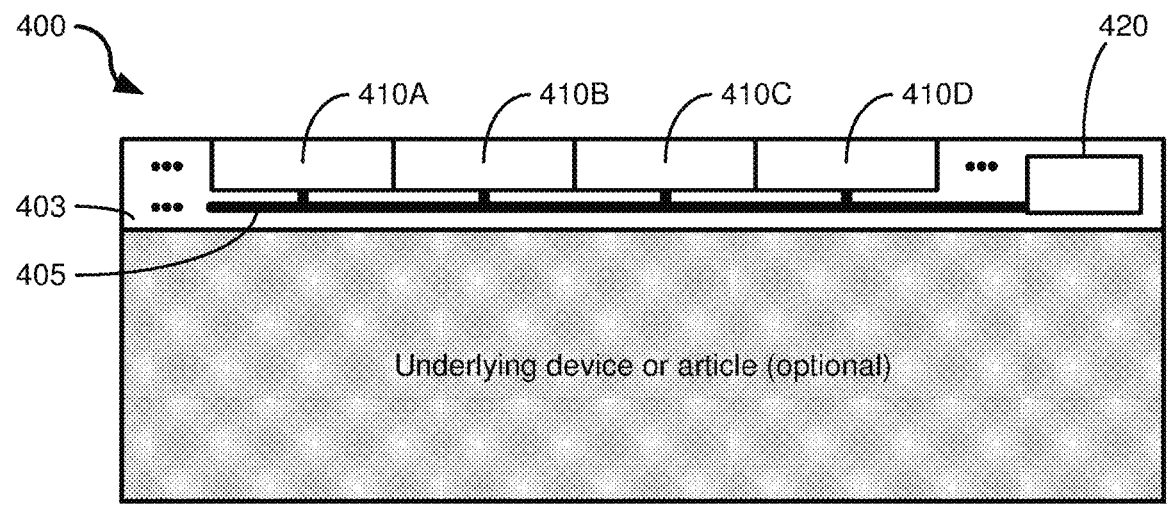
FIGS. 4A and 4B show diagrams of an example embodiment of a synthetic sensing membrane including an array of ultrasonic transceiver sensor devices in accordance with the present technology.
Figure 4B:
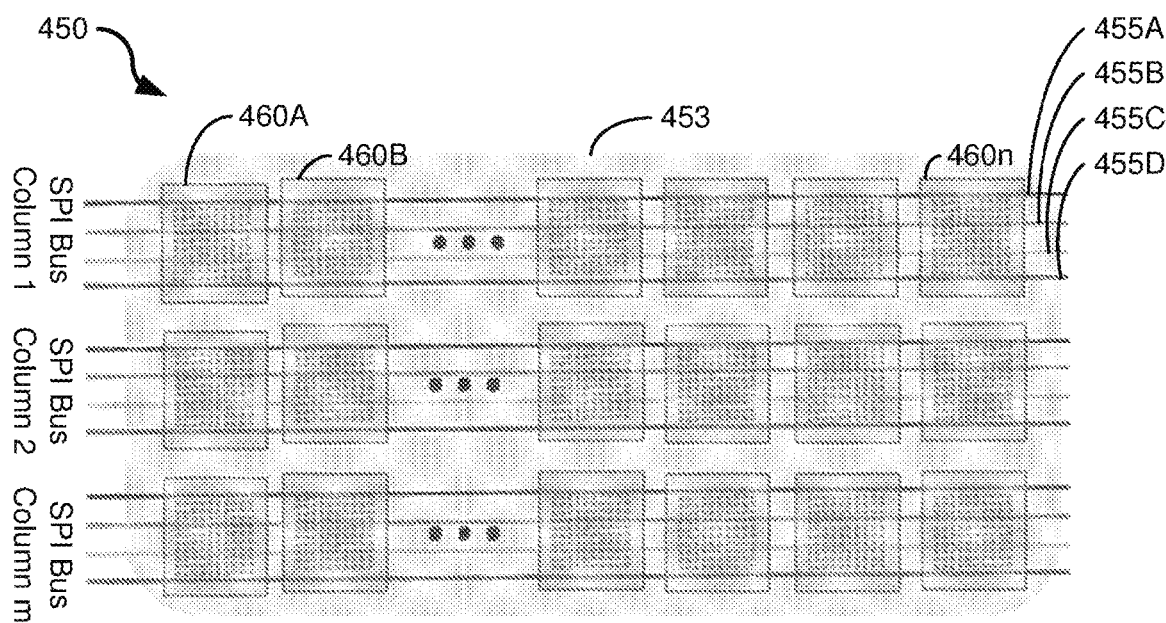

FIGS. 4A and 4B show diagrams of an example embodiment of a synthetic sensing membrane, such as 'robot skin', that includes the engineered ultrasonic touch sensors to detect contact and measure force and/or temperature of other objects, including inanimate and animate (living) objects. While a robot is described in the following examples for implementations the disclosed ultrasonic transceiver chip sensors, other devices or articles can be used, such as wearable devices like gloves, garments or other things worn by a user, tools, meters and the like.

As shown in FIG. 4A, the example synthetic sensing membrane 400 includes an array of ultrasonic transceiver sensor chips 410, e.g., shown as ultrasonic transceiver sensors 410A, 410B, etc., interfaced with a data communication line 405, e.g., such as a bus or array of buses, and structurally coupled in the synthetic sensing membrane 400 by a casing structure or material 403. In some examples, the casing structure or material 403 can include a flexible or soft polymer positioned between ultrasonic transceiver sensor chips 410 in the array, and/or an adhesive material to bind the ultrasonic transceiver sensor chips 410 to a base surface, such as the target object (e.g., the inanimate or animate object). The synthetic sensing membrane 400 is electrically connected, e.g., via the data communication line 405, to a data processing system 420, which can include signal processing circuitry and/or a data processing unit, and a power unit. As shown in the diagram, the synthetic sensing membrane 400 can interface, rest upon and/or attach to an underlying device or article, e.g., including but not limited to a wearable device, a tool, a meter, etc.

The synthetic sensing membrane 400 can include a variety of sensing modalities for the ultrasonic transceiver sensor chips 410 of the array. For example, in some embodiments, the array of ultrasonic transceiver sensor chips 410 can include a combination of an ultrasonic transceiver touch sensor to detect and image an object in contact with the sensor; an ultrasonic transceiver force sensor to measure force applied on the sensor by contact from the object; and/or an ultrasonic transceiver thermal sensor to measure temperature of the proximate region of the object in contact with the sensor. Various combinations of the ultrasonic transceiver touch sensor, force sensor and temperature sensor may be arranged in the array of the synthetic sensing membrane 400.

FIG. 4B shows a top view of an example synthetic sensing membrane, labeled 450, in accordance with the example embodiment of the synthetic sensing membrane 400. The example synthetic sensing membrane 450 includes multiple ultrasonic transceiver sensor chips 460A, 460B . . . 460n arranged on each bus column of an SPI bus. In some embodiments, the synthetic sensing membrane 450 includes 50 ultrasonic transceiver sensor chips 460 arranged on each bus column. In the example synthetic sensing membrane 450, there are four parallel SPI bus lines 455A, 455B, 455C, 455D (per column of the SPI bus) that can connect the ultrasonic transceiver sensor chips 460A-n to power, ground and inputs of signal processing circuitry, such as a differential amplifier. For example, SPI bus line 455A connects circuit elements of the ultrasonic transceiver sensor chips 460A-n to power; SPI bus line 455B connects circuit elements of the ultrasonic transceiver sensor chips 460A-n to ground; SPI bus line 455C connects circuit elements of the ultrasonic transceiver sensor chips 460A-n to a first input of the differential amplifier; and SPI bus line 455D connects circuit elements of the ultrasonic transceiver sensor chips 460A-n to a second input of the differential amplifier. In some embodiments, the synthetic sensing membrane 450 is electrically connected, e.g., via the bus, to a data processing system (e.g., like the data processing system 420 of FIG. 4A), which can include signal processing circuitry and/or a data processing unit, and a power unit.

In some examples of the data processing system 420, a data processing unit includes a processor to process data, a memory in communication with the processor to store data, and an input/output unit (I/O) to interface the processor and/or memory to other modules, units or devices of the synthetic sensing membrane 400 or external devices. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, and/or transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The I/O of the data processing unit can interface the data processing unit with a wired or wireless communications unit of the synthetic sensing membrane 400 to utilize various types of wired or wireless interfaces compatible with typical data communication standards, for example, which can be used in communications of the data processing unit with other devices, via a wireless transmitter/receiver (Tx/Rx) unit, e.g., including, but not limited to, Bluetooth, Bluetooth Low Energy (BLE), Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of the data processing system 420 or an external device.

In some embodiments, for example, the synthetic sensing membrane 400 can include a display unit configured to be in data communication with the data processing unit of the data processing system 420, e.g., via the I/O, to provide a visual display, an audio display, and/or other sensory display that produces a user interface (such as on a software application) for displaying data associated with the estimator. For example, the display unit can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

The synthetic sensing membrane 400 can quantitatively characterize through touch what typically is done by human qualitative assessment. For example, in one's day to day interactions, the sense of touch is often complemented by qualitative assessment such as "you are cold", "you are sweaty", "put more muscle into it", "you might have a fever", "you are dry", etc. Excessive dry skin can be an indication of diseases such as eczema. In some critical cases, one might want to move a robotic hand at a very fast speed away from an overly hot surface. Such assessments can be informative of the health of the person, but also bring two people together in a very human way. Such interactions require measurements of thermal and mechanical interface between the two hands.

Figure 4C:
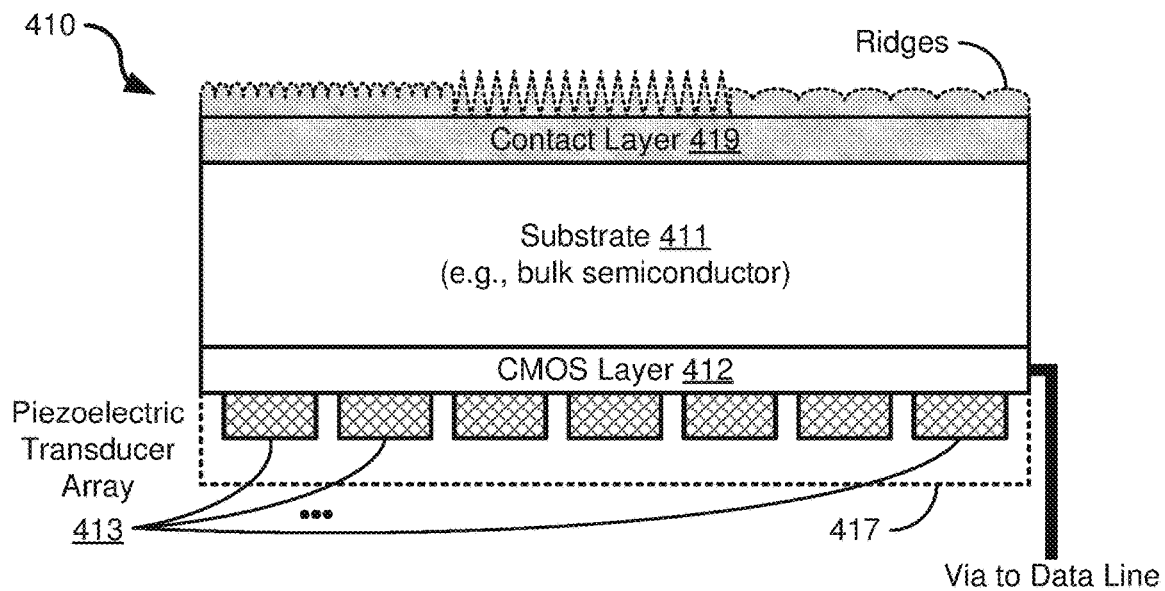
FIGS. 4C and 4D show diagrams of an example embodiment of an ultrasonic transceiver sensor device in accordance with the present technology.

FIG. 4C shows a diagram of an example embodiment of an ultrasonic transceiver sensor chip device 410 in accordance with the present technology. The ultrasonic transceiver sensor chip device 410 includes a substrate 411 (e.g., a bulk semiconductor material, such as silicon), to which a CMOS layer 412 is attached on a first side of the substrate 411 and a contact layer 419 attached to a second side of the substrate 412 (opposite the first side) to provide a surface for contact by the device 410 with an object. In some embodiments, the contact layer 419 includes a polymer material, such as polyvinylidene fluoride (PVDF), polydimethylsiloxane (PDMS) polymers, polyethylene, or parylene. In some implementations, the contact layer 419 can include a polymer material with embedded nanoparticles, e.g., gold nanoparticles, carbon nanoparticles, nickel nanoparticles, combinations thereof or the like, to affect the hardness and softness of the contact layer 419. In some embodiments, the contact layer 419 includes a combination of soft and hard materials. The ultrasonic transceiver sensor chip device 410 includes an array of piezoelectric transducers 413 that are coupled to the CMOS layer 412 to generate acoustic pulses, e.g., which can include acoustic pulses having a frequency of at least 0.5 GHz. In some embodiments, the array of piezoelectric transducers 413 are (optionally) encased in an electrically insulative material 417, e.g., silicon dioxide, silicon nitride or polymer materials, such as polydimethylsiloxane (PDMS) polymers, polyethylene, or parylene.

In implementations, the acoustic pulse generated by a piezoelectric transducer 413A of the array is directed to propagate through the substrate 411 and the contact layer 419, such that when the object is in contact with the surface of the contact layer 419, a reflected ultrasonic pulse is produced and propagates through the contact layer 419 and the substrate 411 to be received at the array of piezoelectric transducers 413. The CMOS elements of the CMOS layer 412 receive and process the transduced outputs from the piezoelectric transducers, which are produced in response to the received reflected ultrasonic pulses.

The contact layer 419 provides a region of the sensor device 410 that provides an ultrasonic signal pathway having different acoustic impedances that can increase signal-to-noise of the reflected acoustic signal from a target object, e.g., which enables the capability to extract data about the target, such as force, temperature and other information. For example, the contact layer 419 can be used to provide higher sensitivity to signals and objects facing the sensor device 410. In some embodiments, the contact layer 419 can include multiple layers such that the impedance of the semiconductor substrate 411 (e.g., silicon substrate) is matched to the contact layer material. In one example, the contact layer 419 can include an outer layer that provides the surface to contact the object and an intermediate layer intermediate layer to facilitate an impedance matching between the semiconductor material (of the substrate 411) and the outer layer of the multi-layered contact layer 419. For example, when the outer layer of the multi-layered contact layer 419 is a soft material, the intermediate layer is configured to couple as much energy to the outer layer of the contact layer 419, which may otherwise suffer loss (e.g., reflectance) at the interface of the substrate and soft materials. In addition to acoustic impedance matching, the contact layer 419 can include features that enable the measurement of desired variables, such as contact forces. In some implementations, the contact layer 419 can be structured to induce phenomena in the surrounding environment to the sensor device 410, such as create a hydrophilic or hydrophobic surface.

In some embodiments, the ultrasonic transceiver sensor chip device 410 includes a textured surface layer, also referred to as "ridges" or textured structures, formed on or as a part of the external surface of the contact layer 419. In implementations, the ridges provide a structure that affects the time and direction of the reflected ultrasonic pulses received at the piezoelectric transducers, which correspond to echo signals of different delays and magnitudes corresponding to the applied force. In some embodiments, the ridges are structured as a homogenous layer of the ultrasonic transceiver sensor chip device 410, in which the ridges have a substantially uniform or consistent material properties (e.g., hardness, elasticity, etc.) and topology (e.g., height, gap distance peak-to-peak, ridge shape, etc.). In some embodiments, the ridges are structured as a heterogenous layer of the ultrasonic transceiver sensor chip device 410, in which the ridges have varying material properties and/or topology among regions of the contact layer 419. In such embodiments, the heterogeneous regions can vary periodically, intermittently or randomly. The diagram of FIG. 4C illustrates an example of a heterogeneous textured surface layer on the contact layer 419 of the example ultrasonic transceiver sensor chip device 410.

The textured surface can facilitate increased resolution of differential between the transmit and returned acoustic signals to determine the types of forces, e.g., normal forces and/or shear forces, incident on the detection surface of the ultrasonic transceiver sensor chip device 410. For example, textured structures with a high aspect ratio of height to width (e.g., pillar ridges) can improve the signal-to-noise of the signal that allow analysis of the differential, as such high aspect ratio structures are more easily pulled or pushed to the side upon shear forces and can be more easily compressed upon normal forces. See FIG. 4E, as an example.

For example, a heterogeneous surface of ridges provides a spatial zoning of determinable acoustic properties based on the differences in material property and topology between the ridges in different regions (zones). These positioning and the diversity of the material properties and/or topology of the ridges in a heterogenous layer provides the ability of the ultrasonic sensor device to extract more information about the object in contact.

In some implementations, for example, the material properties and topology of the ridge structures in the heterogenous layer of ridges can be predetermined, such that the differential signal can be determined based on known parameters. Alternatively or additionally, in some implementations, for example, the material properties and topology of the ridge structures in the heterogenous layer of ridges can be determined based on machine learning techniques that analyze iterations of touching events by objects to determine a precise set of parameters used for subsequent determinations of force, temperature or other characteristics of objects that touch the ultrasonic sensor device.

In some embodiments, the ultrasonic transceiver sensor chip device 410 can include the textured structures etched into the external surface of the bulk semiconductor substrate 411. In such embodiments, the contact layer 419 may or may not include the textured surface. For example, in implementations, the etched features on the surface of the substrate 411 has cavities that affect the propagation of the ultrasound signals, which can be used as a standard in absence of an applied force. When contact is made by an object, the contact layer 419 can compress within the etched cavities of the substrate 411 and change the acoustic properties of the transmit-receive differential such that the device can determine characteristics of the touching object. Similarly, if the device is without the contact layer 419, the material of the touching object can occupy the etched cavities, thereby changing the acoustic properties that can be determined for characterizing the touching object and touching event.

In some embodiments, the ridges are configured to be soft to change in shape based on an applied force by the object. Whereas, in some implementations, the ridges are configured to be hard to withstand change in shape under an applied force by the object, but allow for the object's surface morphology to change within the gap regions formed by the ridges, e.g., thereby increasing actual surface area in contact between the ridges and the touching object. In some example embodiments using a hard contact layer 419, such hard materials can include layers of thin films that can be deposited using thin film deposition approaches. These can include silicon dioxide deposited using plasma-enhanced chemical vapor deposition (PECVD) processes, and silicon-nitride films that can be sputtered or deposited using low pressure chemical vapor deposition (LPCVD) processes. In some example embodiments using a hard contact layer 419, soft materials can include PDMS, silicone, or other rubber-like materials that can more readily change shape under normal physiological forces.

In some embodiments, the contact layer 419 includes a thickness of less than 10 μm, e.g., such as 5 μm or less. Whereas, in some embodiments, the contact layer 419 includes a thickness in the tens of microns. Whereas, in some embodiments, the contact layer 419 includes a thickness in the hundreds of microns or in the millimeter range. Generally, the thickness and material of the contact layer 419 is configured based on the type of sensing application the ultrasonic transceiver sensor chip device 410 is envisioned to be used for.

For example, the contact layer 419 should be formed of a thickness such that the maximum sensitivity to contact forces can be realized. In the case where the contact layer 419 includes soft materials, such as a soft polymer, the loss at high frequency ultrasound can be significant, e.g., where thicknesses in the tens of microns enough to reduce the amplitude of the wave to half of its incident ultrasonic pressure magnitude. In applications where the effect of the contact forces is to be measured at the contact surface above the contact layer 419, the waves have to propagate to the surface and return back. One such application is the imaging of the surface above the contact layer 419; and a more specific case, for example, includes imaging of an object (such as namatodes in soil, described later in this patent document), which would require the waves to go through and come back though the contact layer when a contact layer is employed in the sensor device. In this case, for example, the contact layer 419 can be on the order of tens of microns.

Yet, in some cases, for example, it may be sufficient to alter the interface ultrasonic impedance between the semiconductor substrate 411 and the contact layer 419 to measure the effect of the force on the compressive stress of the polymer at the interface. In this case the transmitted wave does not matter, and the thickness of the layer can be thicker than then absorption distance of the waves. Here, for example, the contact layer 419 can include adhesively attached soft layers that can be a few millimeters in thickness, or sprayed on thin films, or polymer layers that are attached to the substrate 411 adhesively. If the contact layer 419 is made of harder, lower ultrasonic loss materials, such as silicon nitride and silicon dioxide, the contact layer 419 can be thicker, although in most cases films of this kinds are thinner due to the deposition techniques available for them.

The contact layer topology can include features to induce the normal and/or shear stresses. The lateral sizes of the protrusions to induce normal and/or shear stresses typically will determine the aspect ratio which can affect the sensitivity to touch. In some embodiments, for example, the arrangement of protrusion structures can include the average width of the structures being on the order of half the thickness (height or depth of the protrusion) to create structures with 1:2 (width:height) ratio. For example, a coating of PDMS can be configured to be 200 μm thick, in which the example PDMS contact layer includes features having a width of 100 μm wide.

In some implementations of the ultrasonic transceiver sensor chip device 410 in a synthetic sensing membrane, such as the membrane 400 of FIG. 4A, the ultrasonic transceiver sensor chip device 410 can be configured on a flexible base (e.g., flexible casing structure or material 403) and arranged proximate to another ultrasonic transceiver sensor device, which are separated by a soft polymer material between the ultrasonic transceiver sensor devices.

Figure 4D:
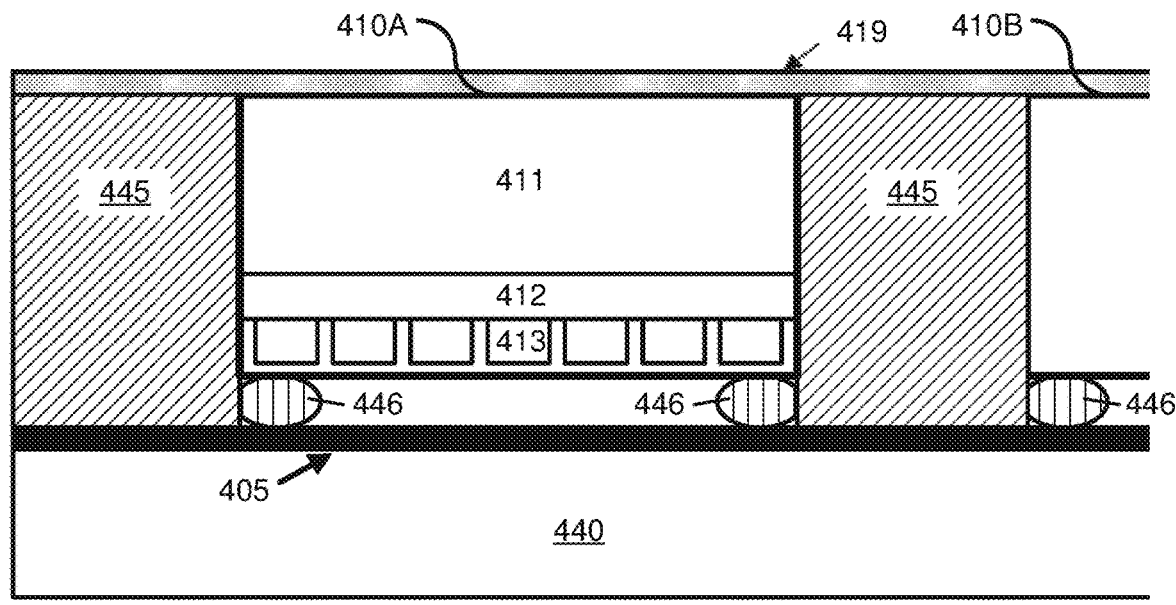

FIG. 4D shows a diagram depicting a cross-sectional view of an example embodiment of the ultrasonic transceiver sensor chip device 410 attached to a flexible substrate 440 (e.g., flex board), e.g., with a flexible wall 445 of a polymer material between multiple chips in an array, to provide flexibility of the array. In some implementations, for example, the transmitted ultrasonic signals, also referred to as "GHZ ultrasonic packets" (GUPs) or ultrasonic pulses, can be incident on the back side of the ultrasonic transceiver sensor chip device 410, where they can be transmitted through the contact layer 419 (e.g., hard polymer material layer, such as PVDF) to the surface of the contacting object, e.g., such as skin, and then reflected back from the surface. For example, the backsides of the ultrasonic transceiver sensor chips 410 interface with the contacting object via the contact layer 419.

The diagram of FIG. 4D depicts multiple ultrasonic transceiver sensor chips 410A and 410B that can be implemented in parallel, e.g., as the sensor chips can be placed on the flexible substrate 440 and interfaced along data communication and/or power lines 405, e.g., data buses. In some embodiments, the multiple ultrasonic transceiver sensor chips 410A and 410B include an electrical connection between the CMOS layer 412 and the data communication line 405. In the diagram of FIG. 4D, the electrical connection is shown as a conductive connection 446 (e.g., conductive adhesive). The array of piezoelectric transducers 413 are spaced apart from the data communication line 405. In some embodiments, the gaps between the adjacent ultrasonic transceiver sensor chips 410A, 410B, etc. are filled with a soft polymer to form the flexible wall 445, e.g., using 3D printing or other flow approaches. For example, the soft polymer can be filled to approximately to the level of the chip height. The gaps between chips filled with the soft polymers can be used to control the flexibility of the sensor membrane, for example. In some embodiments, the contact layer 419 can span across the multiple ultrasonic transceiver sensor chips 410A and 410B and can be a thin polymer coating, e.g., ~3-4 μm coating of electrosprayed PVDF like polymer. In some examples, the contact layer 419 includes a combination of soft and hard materials. The example polymer layer can include PVDF based on its ultrasonic impedance reasonably matched to tissue such that the ultrasonic pulses can easily be ported into skin and reflected from ridges or valleys of the skin.

Implementations of the synthetic sensor membrane 400 can utilize the acoustic signals transmitted by the array of piezoelectric transducer pixels of the ultrasonic transceiver sensor chips 410 to assess contact force and the time delay of the pulses for measuring the temperature of the contacting object, e.g., such as skin. In example applications of fingerprint sensing, for example, as a person's skin is pressed against the sensor membrane's surface, the ridges of the person's finger will get compressed, decreasing the width valley widths, and increasing the ridge widths obtained from the sensors. This creates a flow pattern of the edges that can be used to assess the direction and magnitude of the force. The force is measured by the effect of the force to compress the ridges due to normal forces, while a shear force would bend the ridges such that they are expanded on one side and compressed on one side. The result of compression and expansion will be to change the amplitude and the phase shift of the return signals for the two transducers.

In addition to sensing the deformation of hand and finger ridges, there may be locations of an object that does not have any ridges. In this case, compressible lines and patches of soft materials can be formed and patterned on top or within of the sensor chip, such as the ridges on or of the contact layer 419 for the example device 410, in which the ridges can become compressed when brought in touch with a surface. Sensor chips designed to sense natural ridges and ridges on the sensor itself can be classified as two kinds of touch sensors, just as our hands have different sensory receptors (e.g., hot or cold sensations of thermoreceptors, fine or course touch sensations of mechanoreceptors, etc.), each serving different purposes.

Figure 4E:
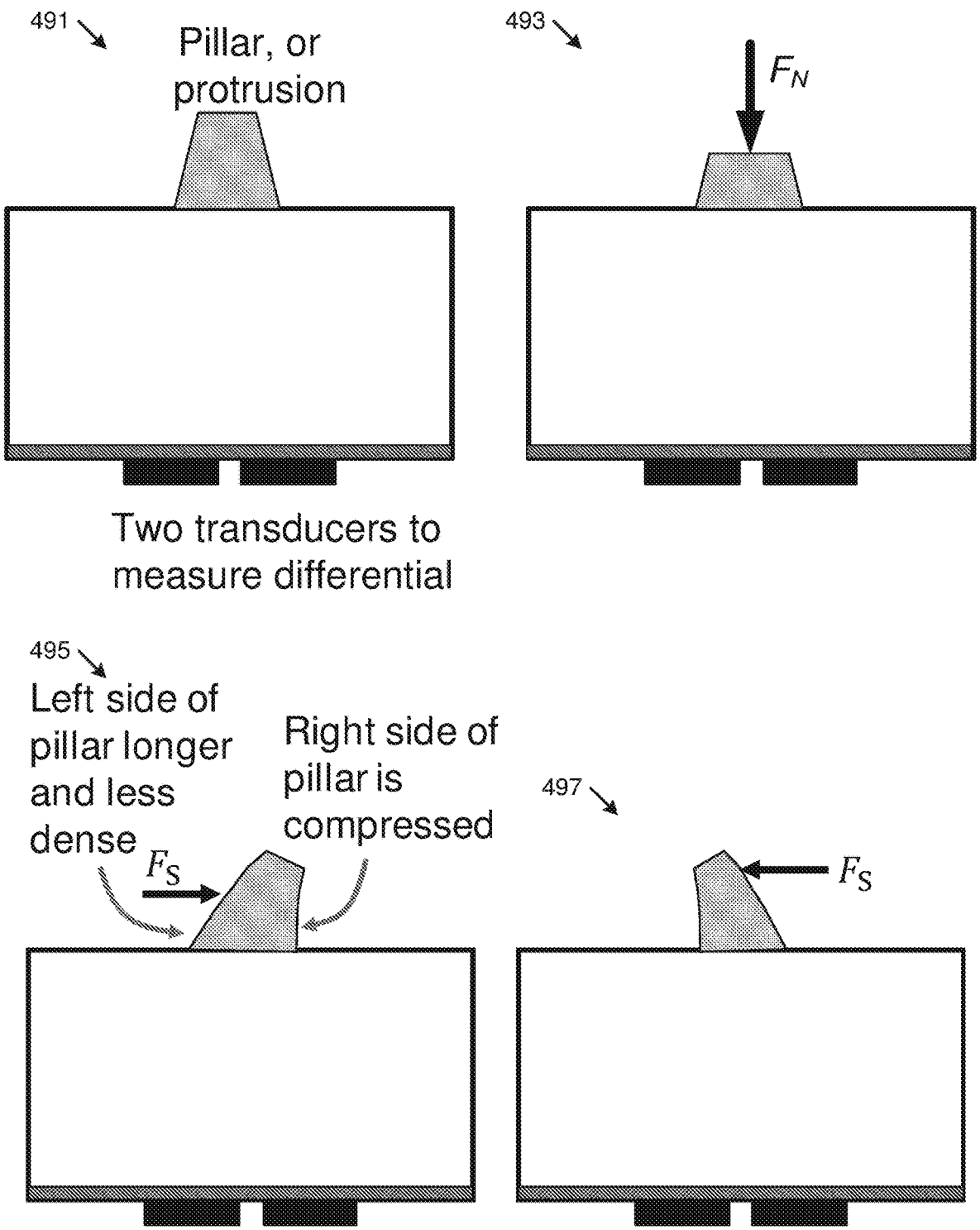
FIG. 4E shows diagrams illustrating a protrusion structure of a textured surface of the contact layer of an example embodiment of an ultrasonic transceiver sensor device in accordance with the present technology.

FIG. 4E shows diagrams illustrating a protrusion structure of a textured surface of the contact layer of an example ultrasonic transceiver sensor device that undergoes normal and shear forces. The diagram 491 shows the ultrasonic sensor device with two piezoelectric transducers configured to measure the differential parameters of a transmitted ultrasonic signal and a received echo signal that propagates through the bulk semiconductor material at a protrusion structure (e.g., pillar) of the contact layer on the bulk semiconductor portion of the device. There are no forces acting upon the device in diagram 491. The diagram 493 shows the morphological change (compression) of the protrusion structure caused by a normal force ($F_N$) acting on the device. The result of compression and expansion will be to change the amplitude and the phase shift of the return signals for the two transducers. The diagrams 495 and 497 show the effects of a shear force ($F_S$) acting upon the protrusion structure from the left side (diagram 495) and the right side (diagram 497), respectively. In the example of diagram 497, the left side of the protrusion structure becomes elongated and less dense, while the right side of the protrusion structure becomes compressed. The ultrasonic complex impedance, including the wave propagation and wave energy absorption, are functions of built in stress and strain determinable from the differential of the ultrasonic transmit signal and ultrasonic return echo, by properties of the protrusion structure can be discerned and used to characterize applied force and temperature of the object in contact. For example, polymer segments can be used to image with ultrasonic transducers effected by applied strains. The stress and strain effect the fundamental reflection coefficients, and the received amplitude, and phase, and time-of-flight are a function of the applied stress.

In an example embodiment, multiple 1×1 mm ultrasonic transceiver sensor chip that include a 10×10 array of 20 μm AlN transducer pixels are arranged on a flexible backing (e.g., flex board) spaced apart using the soft polymer material and coated by a hard polymer layer. Different sensor chips corresponding to the desired sensing modalities of the ultrasonic transceiver sensor chips, e.g., touch, force and temperature, can be arranged in an array of ultrasonic transceiver multi-modal sensing chips on the synthetic membrane. Across an active area of the array, approximately 8-12 naturally occurring ridges can be imaged and tracked. For example, in implementations, the pattern data can be recorded at different ultrasonic frequencies to assess the sonic impedance of the material being contacted. For example, this will help identification of the surface material type between metals, glass, plastic, cloth, skin, etc. Also, for example, using this array, a wealth of new data on ultrasonic absorption versus frequency for materials can be acquired as the material surface (e.g., even of the same material) ages due to surface absorption of materials. Multiple reflections from thin surface coatings can provide the ability to distinguish different coatings such surface painted or not due to multiple reflections from the chip.

Figure 4F:
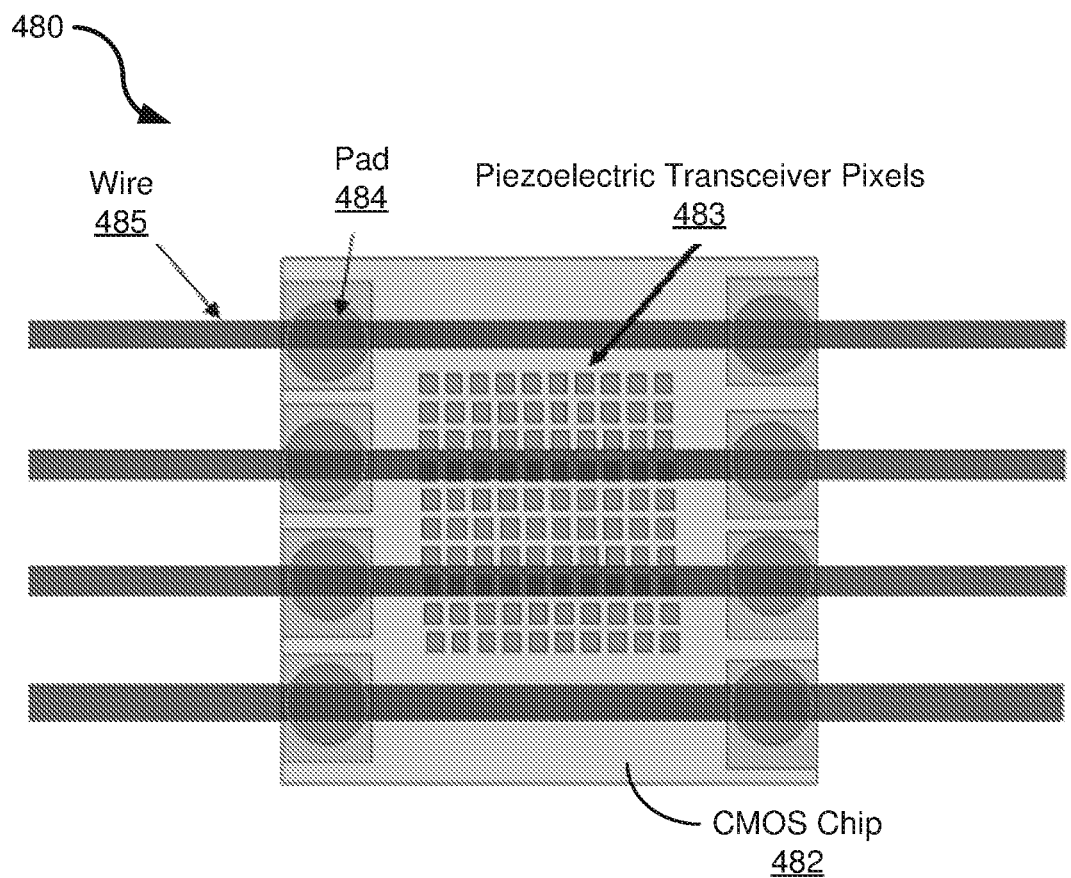
FIG. 4F show a diagram of an example embodiment of an ultrasonic transceiver sensor chip of the array in accordance with the present technology.

FIG. 4F shows a diagram of an example embodiment of an ultrasonic transceiver sensor chip, labeled 480, in accordance with the embodiment of the ultrasonic transceiver sensor chip device 410. In this example, the ultrasonic transceiver sensor chip 480 includes a single CMOS transducer chip 482, e.g., having a size in a range of ~200×200 μm to ~1000×1000 μm, and an array of piezoelectric (e.g., AlN) transceiver pixels 483 arranged in a 10×10 pixel array, e.g., each pixel having a size of ~20×~20 μm. In some embodiments, for example, the ultrasonic transceiver sensor chip 480 can be included on a chip or wafer scale array device. The example CMOS piezoelectric transducer chip 482 connects to a serial peripheral interface (SPI) bus, e.g., via contact pads 484. In some examples, such as where the CMOS chip 482 is ~1 mm×1 mm, the contact pads 484 include a 100 μm dimension (e.g., radius or length depending on the geometry) and are electrically coupled to the wires 485 of the SPI bus, e.g., 50 μm wire. In some embodiments, the ultrasonic transceiver sensor chip 480 also can include programmable fuses and memory elements to retain addresses.

Figure 5A:
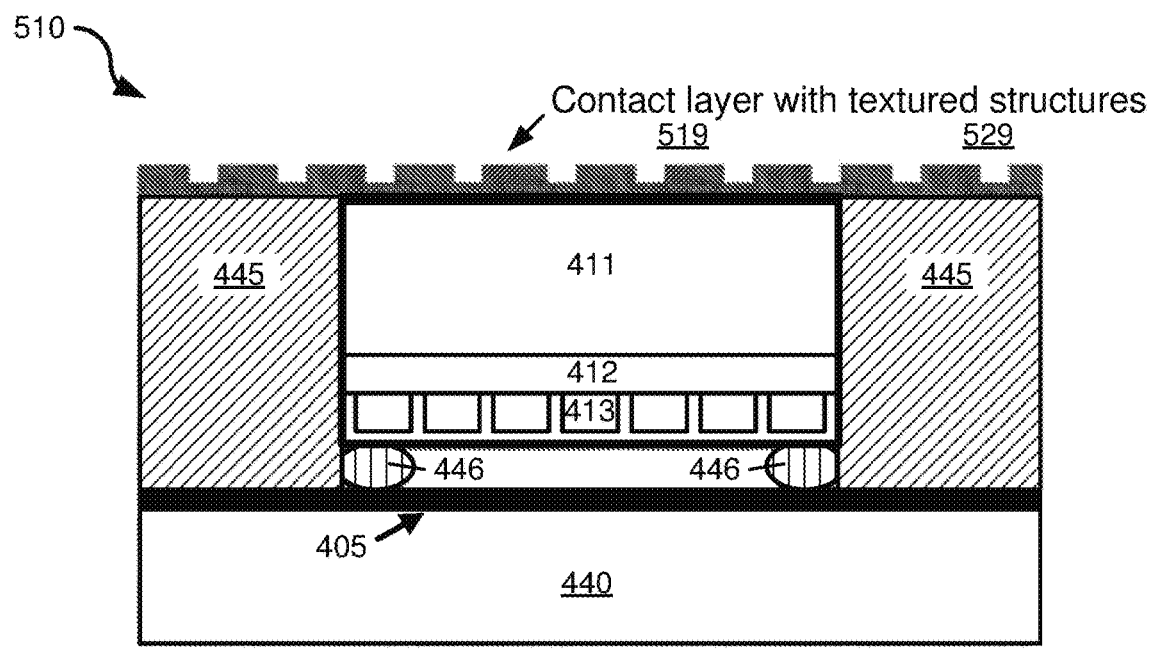
FIG. 5A shows a diagram of an example embodiment of an ultrasonic transceiver force sensor device in accordance with the present technology.

FIG. 5A shows a diagram of an example embodiment of an ultrasonic transceiver force sensor device 510 in accordance with the present technology. The ultrasonic transceiver force sensor device 510 includes features of the ultrasonic transceiver sensor device 410 and with a plurality of protruding and/or receding textured structures 529 patterned on or within the exposed surface of a contact layer 519 (e.g., hard polymer layer over the transceiver chip). The textured structures 529 are also referred to as "ridges." Each textured structure, such as each structure that protrudes and/or each portion that recedes, is patterned at a predetermined location with respect to the array of piezoelectric transducers. In some implementations, the ridges can be formed in the hard polymer layer to have a particular width, depth and geometry for each ridge. In some implementations, ridges can be formed on the hard polymer layer.

As shown in FIG. 5A, the ultrasonic transceiver force sensor device 510 includes the substrate 411 (e.g., silicon) in which the CMOS layer 412 is attached to one side of the substrate 411 and the array of piezoelectric transducers 413 are coupled to the CMOS layer 412. The ultrasonic transceiver force sensor device 510 includes the contact layer 519 (e.g., hard polymer layer) attached to the opposite side of the substrate 411, which includes textured structures 529 (e.g., ridges) formed on the surface of the contact layer 519, which includes forming the ridges within the layer and/or protruding out of the layer. The contact layer 519 provides a surface for contact with the external object.

In implementations of the ultrasonic transceiver force sensor device 510, for example, gigahertz ultrasonic pulse generated by the piezoelectric transducers 413 of the array are directed to propagate through the substrate 411 and the contact layer 519, such that when the object is in contact with the surface of the contact layer 519 and affects the morphology of the textured structures 529, reflected ultrasonic pulses are produced and propagate back through the contact layer 519 and the substrate 411 to be received at the array of piezoelectric transducers 423. CMOS elements of the CMOS layer 412, which are in communication with the array of piezoelectric transducers 423, process output signals received from the piezoelectric transducers that the piezoelectric transducers produce in response to the received reflected ultrasonic pulses. These reflected ultrasonic pulses received at the piezoelectric transducers include varying times with amplitudes associated with the ridges 519, which change in shape (e.g., expand, retract) based on the applied force from the object in contact with the textured structures, that correspond to echo signals of different delays and magnitudes to represent physical features of the object in contact with the ultrasonic transceiver force sensor device.

Figure 5B:
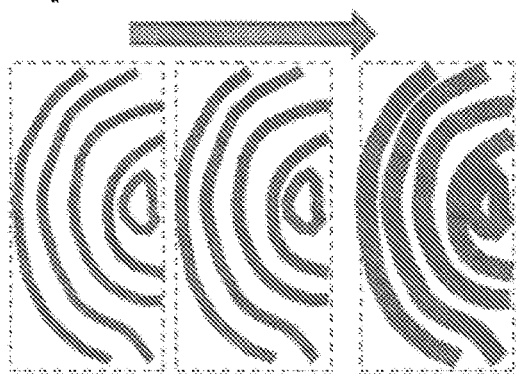
FIG. 5B shows a diagram of an example imaged surface topology depicting the ridge widths increase as a result of compression.

FIG. 5B shows a diagram of an imaged surface topology, e.g., fingerprint in this case, in which the ridge widths increase as a result of compression between the object's body and the sensor's surface. The textured layer, like that shown in FIG. 5B, provides structural features that change in accordance with applied force, and which the reflected GUPs signals are processed to image how they expand and retract, which can be used to determine the energy corresponding to the applied force.

Figure 5C:
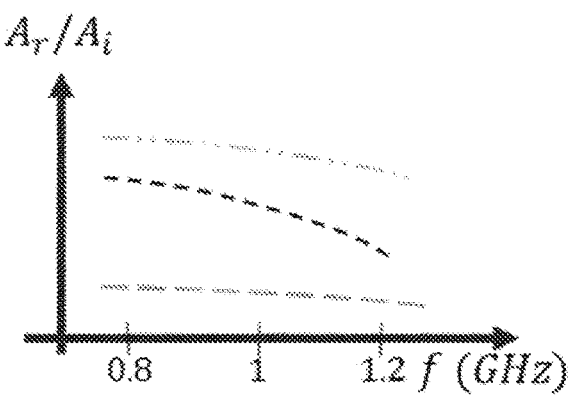
FIG. 5C shows a plot depicting the energy return along every ridge of an example ultrasonic transceiver force sensor.

FIG. 5C shows a plot depicting the energy return along every ridge, which can be a function of dispersion of ultra-sound into the material. Ultrasonic impedance and absorption is a function of frequency in many materials, an effect that leads to dispersion. Waves at different frequencies travel at different phase velocities. Each material has a specific dispersion which can be used to identify materials touching the surface. Each of the curves shown in FIG. 5C illustrates these differences for a different material.

Figure 6:
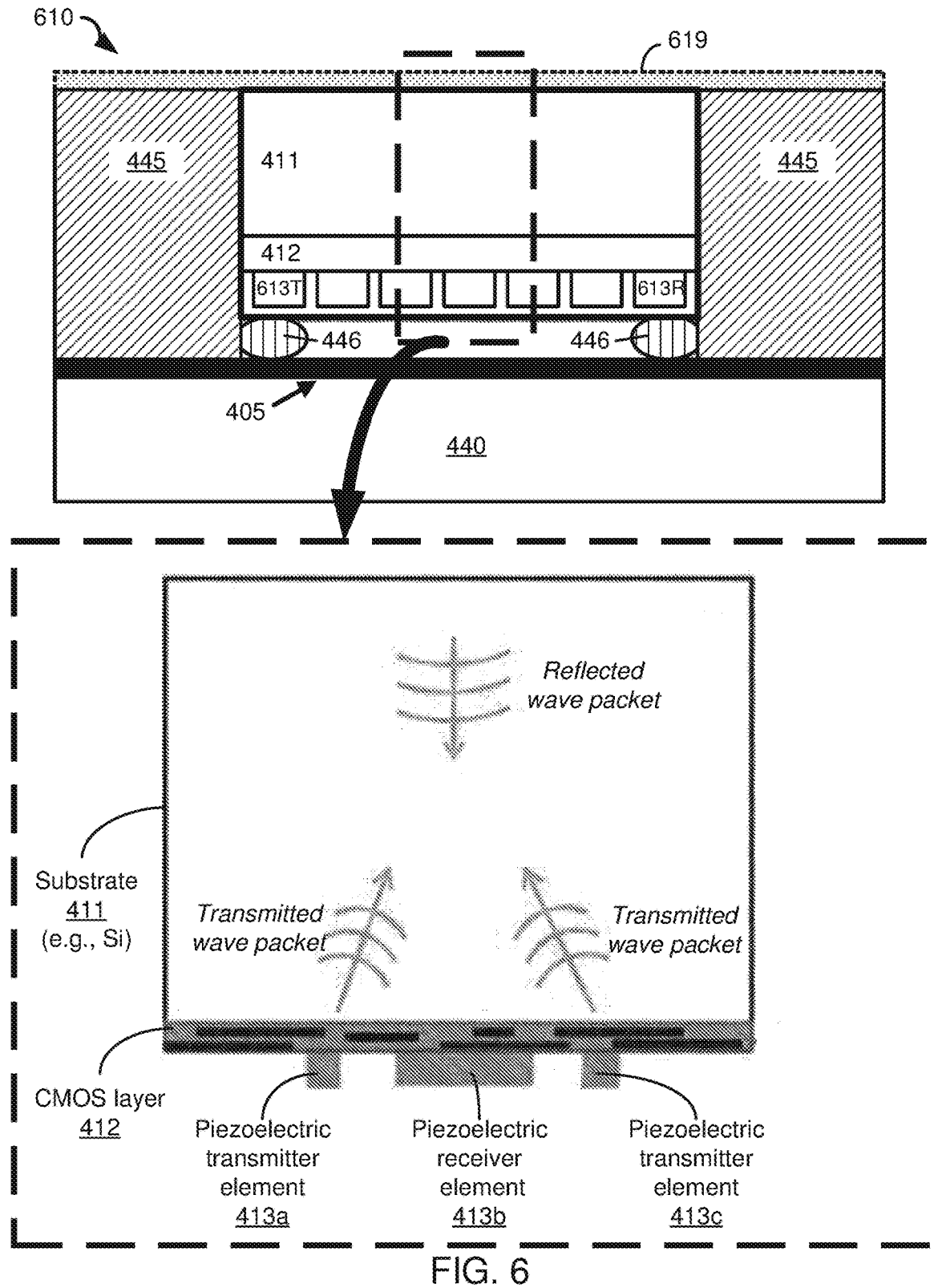
FIG. 6 shows a diagram of an example embodiment of an ultrasonic transceiver temperature sensor device in accordance with the present technology.

FIG. 6 shows a diagram of an example embodiment of an ultrasonic transceiver temperature sensor device 610 in accordance with the present technology. The ultrasonic transceiver temperature sensor device 610 includes features of the ultrasonic transceiver sensor device 410, in which the array of piezoelectric transducers includes one or more transmit transducers 613T and one or more receive transducers 613R, where a transmit transducer 613T are configured to transmit acoustic signals to returned from (e.g., reflect off) the interface of the device 610 and touching object and received as return echo signals at a receive transducer 613R. In some embodiments, the ultrasonic transceiver temperature sensor device 610 can include a contact layer 619. In some embodiments, the ultrasonic transceiver temperature sensor device 610 can include a plurality of protruding and/or receding textured structures (like the ridges shown in FIG. 4C or ridges 529 shown in FIG. 5A) patterned on or within the exposed surface of a contact layer 519 (e.g., hard polymer layer over the transceiver chip).

In an example embodiment, the ultrasonic transceiver temperature sensor device 610 includes a group of transmit piezoelectric transducers 613T and a group of received piezoelectric transducers 613R. For example, the ultrasonic transceiver temperature sensor device 610 includes the substrate 411 (e.g., silicon) in which the CMOS layer 412 attached to one side of the substrate and the array of piezoelectric transducers 613 are coupled to the CMOS layer. The opposite side of the example silicon substrate provides a surface for contact with the object. The group of transmit piezoelectric transducers generate a packet of gigahertz ultrasonic pulses directed to propagate through the substrate and the contact layer. When the object, such as a finger or inanimate object, is in contact with the surface of the contact layer, the reflected gigahertz ultrasonic pulses propagate back through the contact layer and the substrate to be received at the group of receive piezoelectric transducers. CMOS elements of the CMOS layer 412, which are in communication with the transmit and the receive groups of piezoelectric transducers 613T and 613R, respectively, process signals associated with the transmission of the wave packet by the transmit piezoelectric transducers and signals associated with the reflected wave packet received from the receive piezoelectric transducers.

To measure the temperature of the object on the ultrasonic transceiver temperature sensor 613, the ultrasonic pulse signal time-of-flights (TOFs) are quantified. For example, in some implementations, the CMOS layer 412 provides the data associated with the transmitted and reflected ultrasonic wave packets to a data processing unit via the data communication line 405 (e.g., bus), e.g., in which the CMOS layer 412 and the data line 405 are connected via conductive connection 446. In an example, the time for an ultrasonic pulse signal to propagate from a transducer pixel to a second transducer pixel can be 150 ns at room temperature (e.g., 22-25° C.). When the ultrasonic transceiver temperature sensor device 610 is coupled in a device with a clock (e.g., such as stable oscillator clock operating at 15 ns), then a typical time of flight of a pulse can be 10 clock cycles. When an object is in contact with the ultrasonic transceiver temperature sensor, the local temperature at the contact site changes (e.g., warmer), which alters the time of flight of subsequent pulses. This difference in time of flight can be used to determine the temperature of the object in contact.

For example, a returned ultrasonic pulse signal can also have an altered phase owing to the reflection coefficients effect on the phase. This phase can be measured by mixing the return signal with the VCO used to transmit the pulse, e.g., like radio receivers. The phase change is another variable that relates to the effects at the interface and the bulk on the transmitted pulses.

As an example, as the surface of a robot hand employing the synthetic sensing membrane 400 (that includes the device 610) touches a human hand, heat flow will start to change the temperature of the ultrasonic transceiver sensor device. As the temperature rises or falls, the speed of sound in the semiconductor substrate (e.g., silicon) will decrease or increase correspondingly. As the temperature of the chip changes, a temperature distribution T(x,y) will be established, modifying the pulse time-of-flight (TOF). After the surface has been in contact with the external surface for a long time, the TOF will reach a steady state value corresponding to the steady state temperature. The rate at which this equilibrium will be reached can be determined by the thermal conductivity of the object and silicon, and also the contact resistance between the two surfaces. For example, for most objects, the thermal conductivity will be much lower than that for silicon, and the rate of TOF change will be a function of the object thermal conductance. For example, the fastest time for equilibrium would be the thermal time constant of 0.5 mm thick silicon chip itself. This can be estimated to be ~0.3.1 ms (e.g., silicon thermal diffusivity=0.8 $cm^2$/s). Moreover, for example, since the nominal GUP TOF is 0.15-0.17 ms for the 0.5 mm thick wafer, the fastest possible time of 3-4 ms to reach steady state will be long enough to see transients of temperature encountered by the sensor.

Figure 7A:
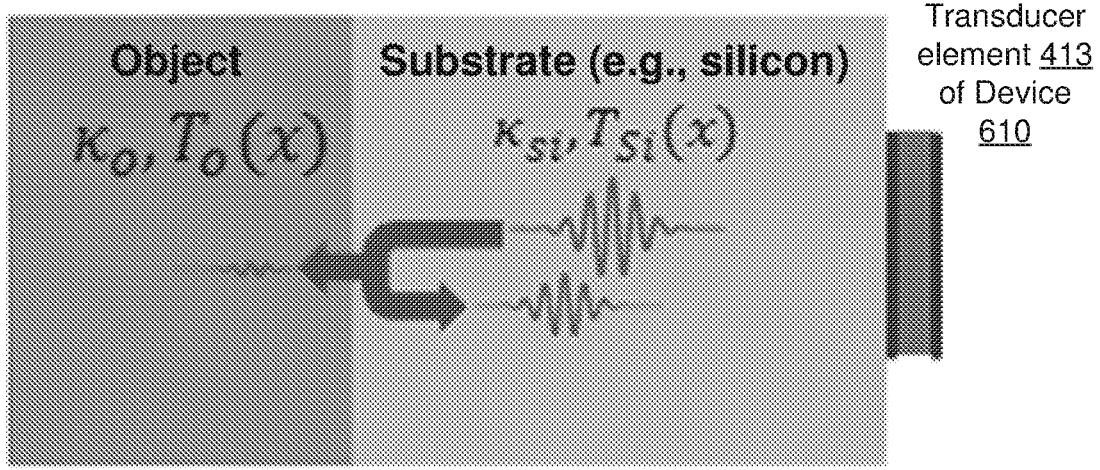
FIGS. 7A-7C show a model and data plots of a transducer touching a surface with different thermal conductivity and temperature.

With each contact, the chip is able to record and transmit the temporal record and metrics based on the temporal record to warn of events. This time frame is fast enough time scale to warn of contact with excessively low or high temperatures. As shown in the diagrams of FIGS. 3A, 6 and 7A, and exemplified in the data plots of FIGS. 3B, 3C, 7B and 7C, the TOF data can also be indicative of the surface being contacted—in the example case of insulating surface, the heat flux will be slower to enter the chip, and the TOF curve will change slowly. Hence the slope of TOF(x) versus x will be marker indicative of the thermal conductivity of the object. Furthermore, the steady state temperature in silicon can be measured by the measurement of the steady state TOF reached after the thermal diffusion time.

Figure 7B:
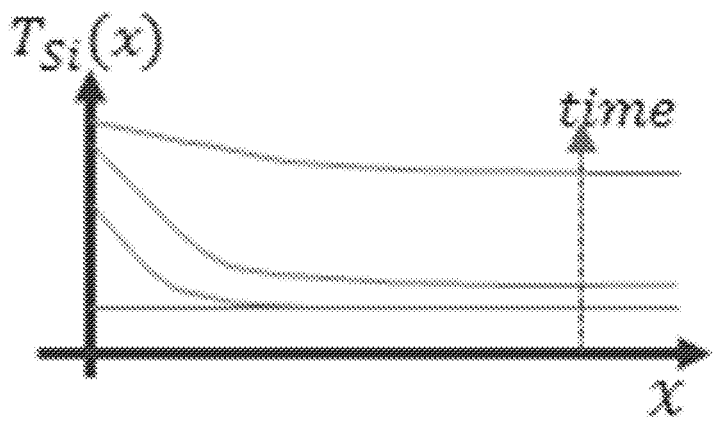
Figure 7C:
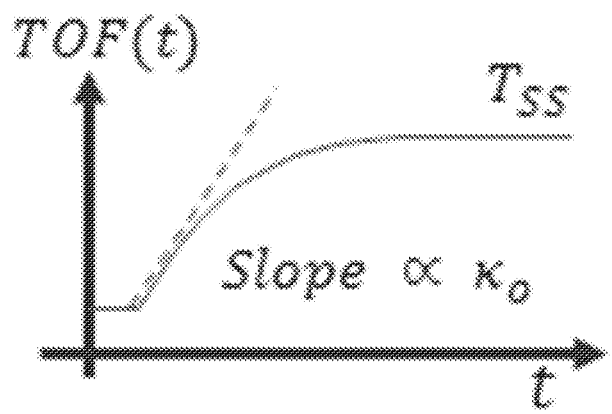

FIGS. 7A-7C show a model illustration and data plots of an example transducer of the ultrasonic transceiver temperature sensor device 610 touching a surface with different thermal conductivity and temperature. FIG. 7A shows an approximate 1-dimensional model of transducer touching a surface with different thermal conductivity and temperature. FIG. 7B shows a data plot of the temperature profile in silicon changes. FIG. 7C shows a data plot of an example time of flight measurement depicting the steady state temperature.

Figure 8:
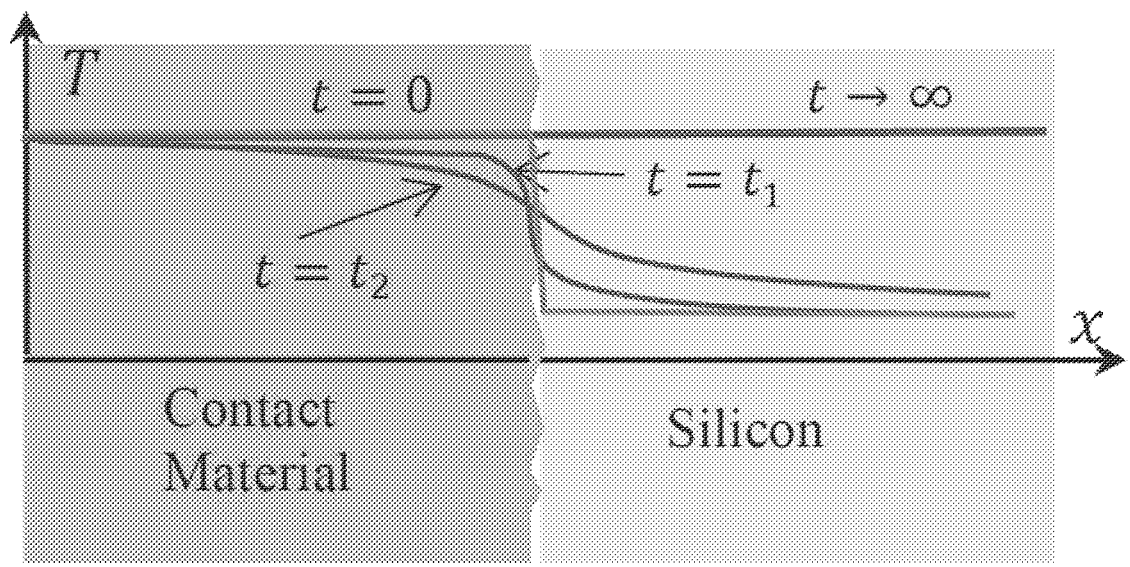
FIG. 8 shows a model depicting an object's surface touching silicon that will lead to heat conduction.

FIG. 8 shows an illustrative model showing that bringing a surface of contact material touching the silicon will lead to heat conduction through the interface for $t_2 > t_1$. As demonstrated by the model, the ultrasonic transceiver temperature sensor device 610 is able to sense the thermal properties of the material (object) through measuring the transient thermal time constant when the sensor comes into contact with the material. FIG. 8 shows two different materials at different temperatures coming into contact. At contact the temperature difference will lead to heat flux across the interface with a specific contact resistance which will be a function of roughness. This can occur for example when a sensor made of a semiconductor material, like silicon, placed at room temperature comes in contact with the human body at a higher temperature typically at 37° C.

The heat diffusion creates a temperature gradient in the silicon bulk as a function of time until the silicon slab is thermally equilibrated with the contact material. At the moment of contact, the thermal depth is less than the thickness of the materials. In this case, the two materials are considered semi-infinite solids and the temperature at the contact between the silicon and the material in contact follows the equation:

$$T_c = \frac{\sqrt{(k\rho C_p)_{cm}} T_{cm} + \sqrt{(k\rho C_p)_{Si}} T_{Si}}{\sqrt{(k\rho C_p)_{cm}} + \sqrt{(k\rho C_p)_{Si}}} \quad \text{(Eq. 1)}$$

where $T_c$ is the temperature at the interface right at the moment of contact. $T_{si}$ and $T_{cm}$ are the initial temperatures of silicon and contact material, respectively. k, p, and $C_p$ are the thermal conductivity, density, and specific heat, respectively. After contact, the thermal depth becomes comparable to the thickness of silicon and Equation (1) is no more valid.

In example implementations described below, an example embodiment of the device 610 that included AlN piezoelectric transducers on top of silicon substrate was used to generate GHz ultrasonic pulse packets. These pulses travel through the substrate, reflect from the bottom side of the substrate, travels back to the top and are received by another transducer which converts it to electrical signal to be measured. The delay between the transmitted and received pulses is measured. When a material at different temperature come into contact with the bottom of the silicon substrate, the silicon substrate temperature starts to change gradually and directly affects the delay between the transmitted and received signals through thermal coefficient of expansion and speed. The use of high frequency ultrasonic (e.g., 2.7 GHz) allows for narrower pulses to be transmitted which improves the time resolution of measurements.

The explicit form of the finite-difference method can be used to solve the transient conduction problem for two different materials coming into contact having different initial temperatures. A 1-D conduction problem in the direction perpendicular to the plane of contact (x-direction) is solved. For simplicity, conduction is assumed to be the dominant transfer mechanism as, in solids, convection is absent and radiation can be neglected.

For a one-dimensional system, under constant properties and no internal heat generation, the heat equation can be written as $$\frac{\rho C_p}{k} \frac{\partial T}{\partial t} = \frac{\partial^2 T}{\partial x^2} \quad \text{(Eq. 2)}$$

T is the temperature, t is time, and x is the direction of thermal diffusion. To obtain the finite difference form of this equation, the problem must be discretized in both space and time. Using m subscription to designate x-location of discrete nodal points and p subscription to indicate discrete points in time, the explicit form of the finite-difference equation can be written as $$\frac{\rho C_p}{k} \frac{T_m^{p+1} - T_m^p}{\Delta t} = \frac{T_{m+1}^p + T_{m-1}^p - 2T_m^p}{(\Delta x)^2} \quad \text{(Eq. 3)}$$

where $\Delta x$ and $\Delta y$ are the nodal points spacing and time interval, respectively.

Figure 9:
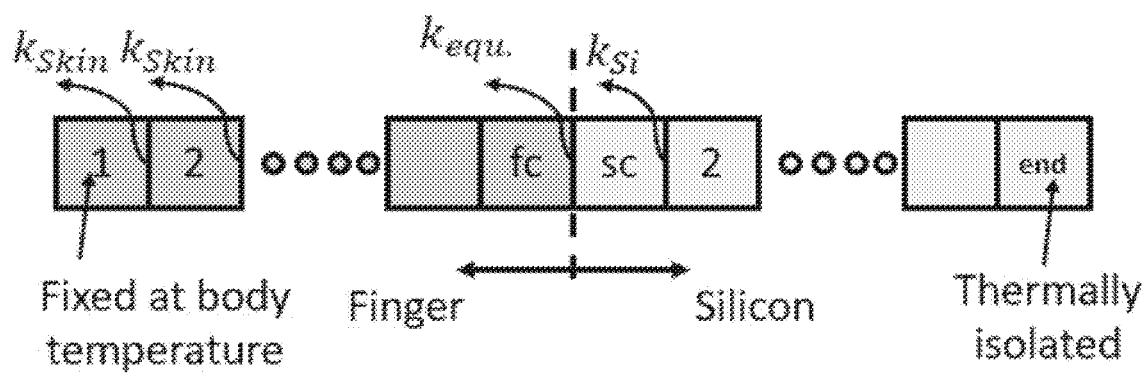
FIG. 9 shows a model for the 1-D geometry of a silicon substrate in contact with a finger demonstrating the equivalent thermal conductance between the finger and silicon.

FIG. 9 shows a model for the 1-D geometry of a silicon substrate in contact with a finger demonstrating the equivalent thermal conductance ($k_{equ}$) between the finger and silicon. Density and specific heat can be assigned to each node. Thermal conductivity, on the other hand, should be assigned to edges rather than nodes. As shown in FIG. 9, km represents the thermal conductivity at the right edge of node m and km−1 represents the conductivity at the left edge. Plugging this in Equation (3) and solving for the next temperature in the discrete time domain gives Equation (4):

$$T_m^{p+1} = T_m^p \left(1 - \frac{k_m}{(\rho C_p)_m \Delta x^2}\Delta t - \frac{k_{m-1}}{(\rho C_p)_m \Delta x^2}\Delta t\right) + \quad \text{(Eq. 4)}$$
$$\frac{\Delta t}{(\rho C_p)_m \Delta x^2}(k_m T_{m+1}^p + k_{m-1} T_{m+1}^p)$$

As shown in FIG. 9, the diagram shows an example substrate of silicon of length 675 μm (thickness of 6-inch wafer), for example, in contact with the material under test. To solve the finite difference equation, boundary and initial conditions should be specified. Initial temperature for silicon is 25° C. (room temperature) and for the material under test is 37° C. in case of human finger. The temperature at the human finger end is fixed at 37° C. and the silicon end is isolated. These conditions can be translated to the following equations.

$$T_{m=1 \to fc}^{p=1} = 37° C., \quad T_{m=sc \to end}^{p=1} = 25° C.$$

$$T_{m=1}^{all\,p} = 37° C., \quad T_{m=end}^{all\,p} = T_{m=end-1}^{all\,p} \quad \text{(Eqs. 5 and 6)}$$

FIGS. 10A and 10B show the temperature profile across x at different times for bare finger and finger with rubber gloves, respectively. Because silicon has higher thermal conductivity, temperature profile in silicon is approximately constant. As shown in FIG. 10C, as the rubber thickness increase, thermal time constant ($\tau_{th}$) increases. $\tau_{th}$ for bare hand is 1.21 s and for rubber thicknesses of 100 μm, 200 μm, and 400 μm, the values are 2.13 s, 2.97 s, and 4.38 s, respectively. FIG. 10D shows a data plot depicting the effect of skin thickness on time, showing the values of thermal time constants for different skin thicknesses. For a skin thickness higher than silicon thickness, $\tau_{th}$ is nearly constant.

Figure 11:
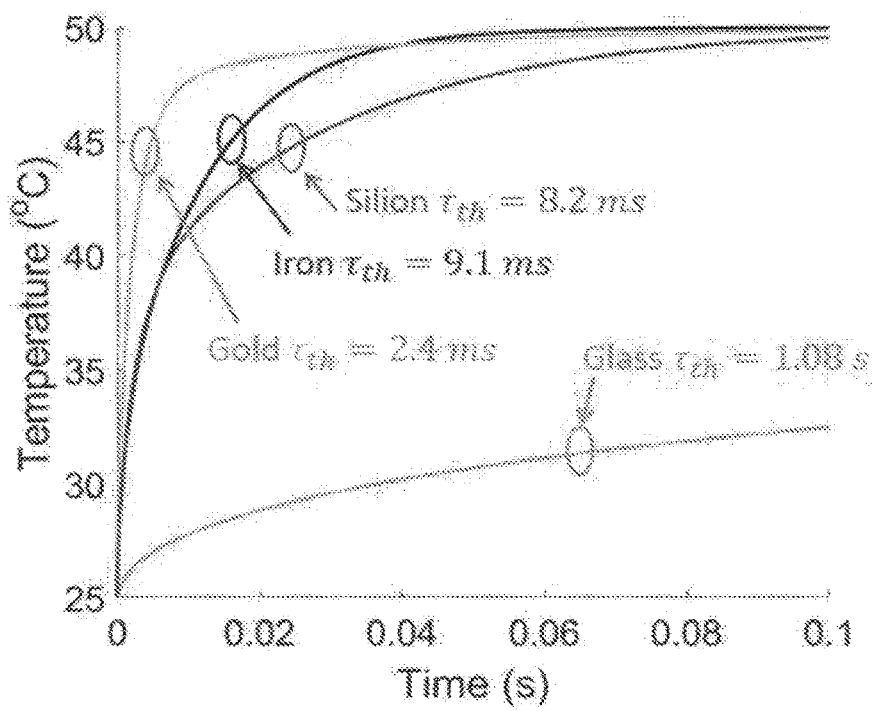
FIG. 11 shows a data plot depicting the transient heating of silicon for different materials at an initial temperature of 50° C.

FIG. 11 shows the transient heating of silicon for different materials at an initial temperature of 50° C. Thermal time constants for heat transfer in the sensor when it comes into contact with 1 mm of gold, iron, silicon, and glass are 2.4 ms, 9.1 ms, 8.2 ms, and 1.08 s, respectively.

Figure 12:
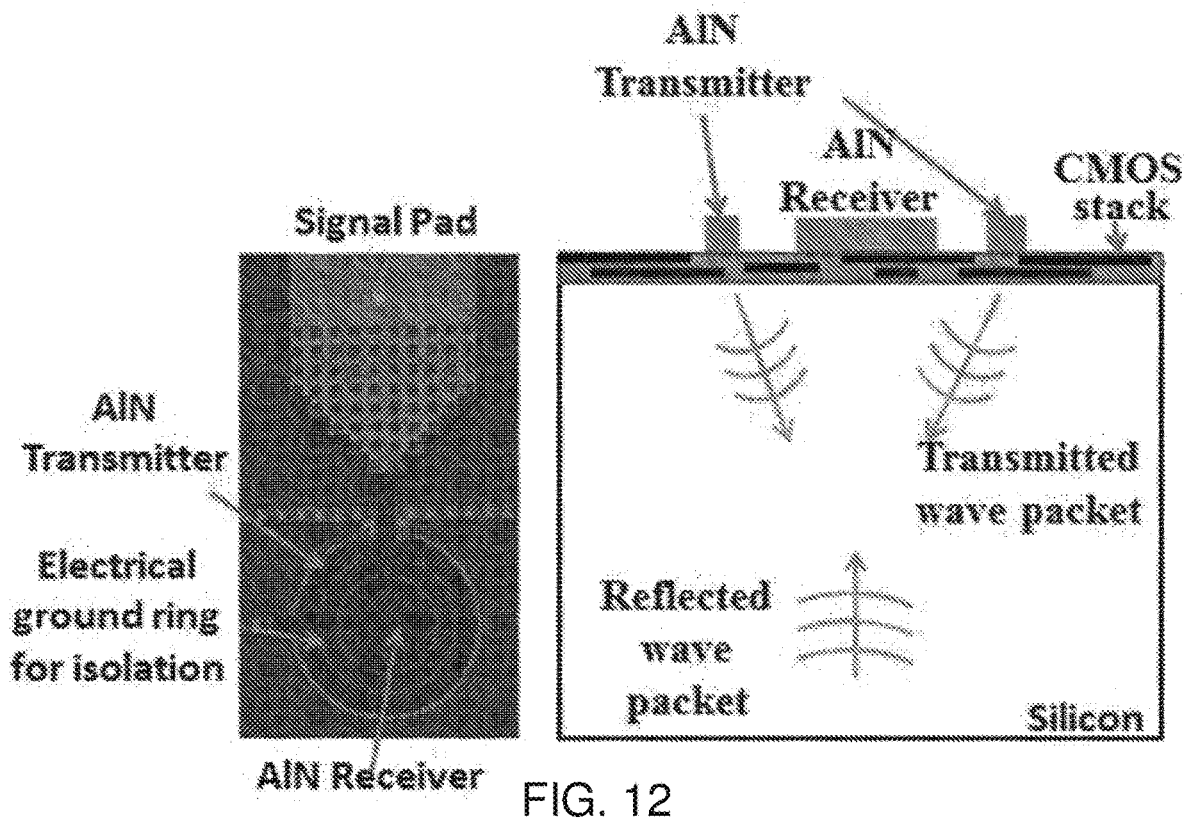
FIG. 12 shows optical image of the AlN transmit and receive transducers in an example embodiment of an ultrasonic transceiver temperature sensor device.

FIG. 12 shows optical image of the AlN transmit and receive transducers in an example ultrasonic transceiver temperature sensor device 610. The outer ring is used to transmit the RF wave packet through silicon wafer. The inner and outer radiuses of the transmitting ring are 73 µm and 93 µm, respectively. In this example, the receiver transducer is a circular transducer placed in the middle of the ring of radius 50 µm. An electrical ground ring is placed between the transmitter and the receiver to electrically isolate them from each other to minimize electrical RF coupling. Referring also to the diagram on the right of FIG. 12, the acoustic wave packet propagates through the semiconductor substrate 411 (e.g., silicon), reflects from the back side of the semiconductor substrate and is received by the circular transducer in the middle of the transmitting ring transducer.

Figure 13:
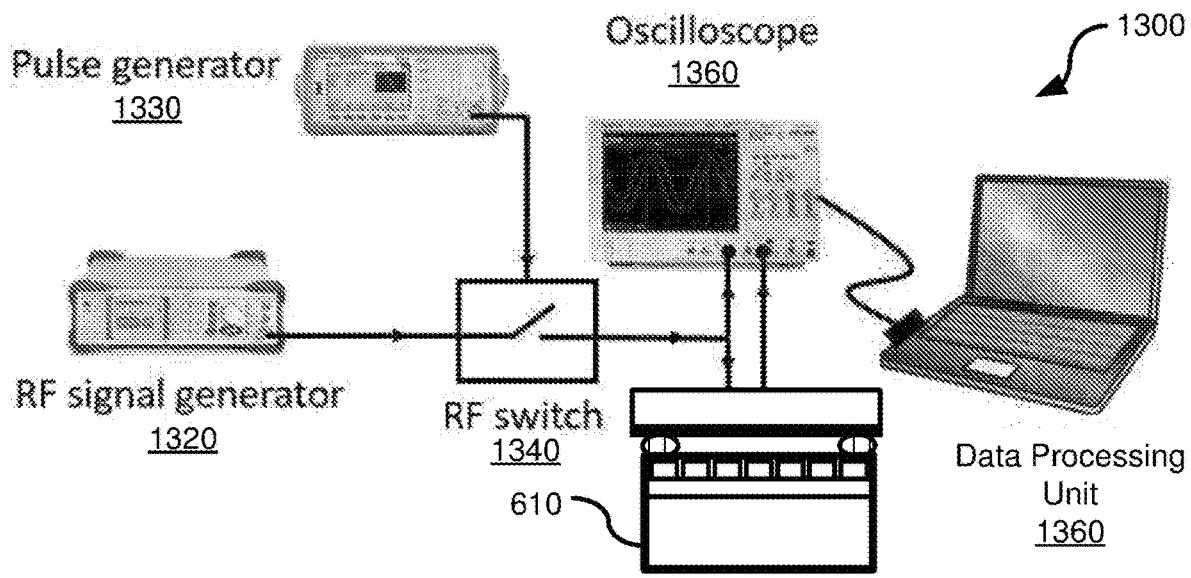
FIG. 13 shows a diagram of an example embodiment of a system used in the example implementations to test the example ultrasonic transceiver temperature sensor device.

FIG. 13 shows a diagram of an example embodiment of a system used in the example implementations to test the example ultrasonic transceiver temperature sensor device 610. The system, labeled 1300, comprises an RF signal generator 1320, a pulse generator 1330, an RF switch 1340, one or more ultrasonic transceiver temperature sensor devices 610, and an oscilloscope 1360 (e.g., 20 Gs/s oscilloscope). In implementations, for example, the RF switch 1340 is controlled by the pulse generator 1330 to create pulses modulated by the high frequency signal generated by the RF signal generator 1320. The pulse width was configured to be less than the time of flight of acoustic waves in silicon so that echoes do not overlap. In the example implementations, since the time of flight for a round trip in silicon was ~150 ns, the pulse width was chosen to be 110 ns. The RF electrical pulse was then used to actuate the transmitter AlN transducer ring. The generated acoustic pulse travels through the silicon substrate, reflects from the back side and is converted back to electrical signal through the receiver transducer. The oscilloscope measures both the transmitted and received pulses. The data processing unit included a computer with MATLAB, which was used to capture the data and measure the time of flight of the acoustic wave in silicon by measuring the delay between the transmitted and the received signal. Example results of the implementations using the system 1300 for temperature sensing using an example ultrasonic transceiver temperature sensor device 610 are shown in FIGS. 14A-14C.

Figure 14A:
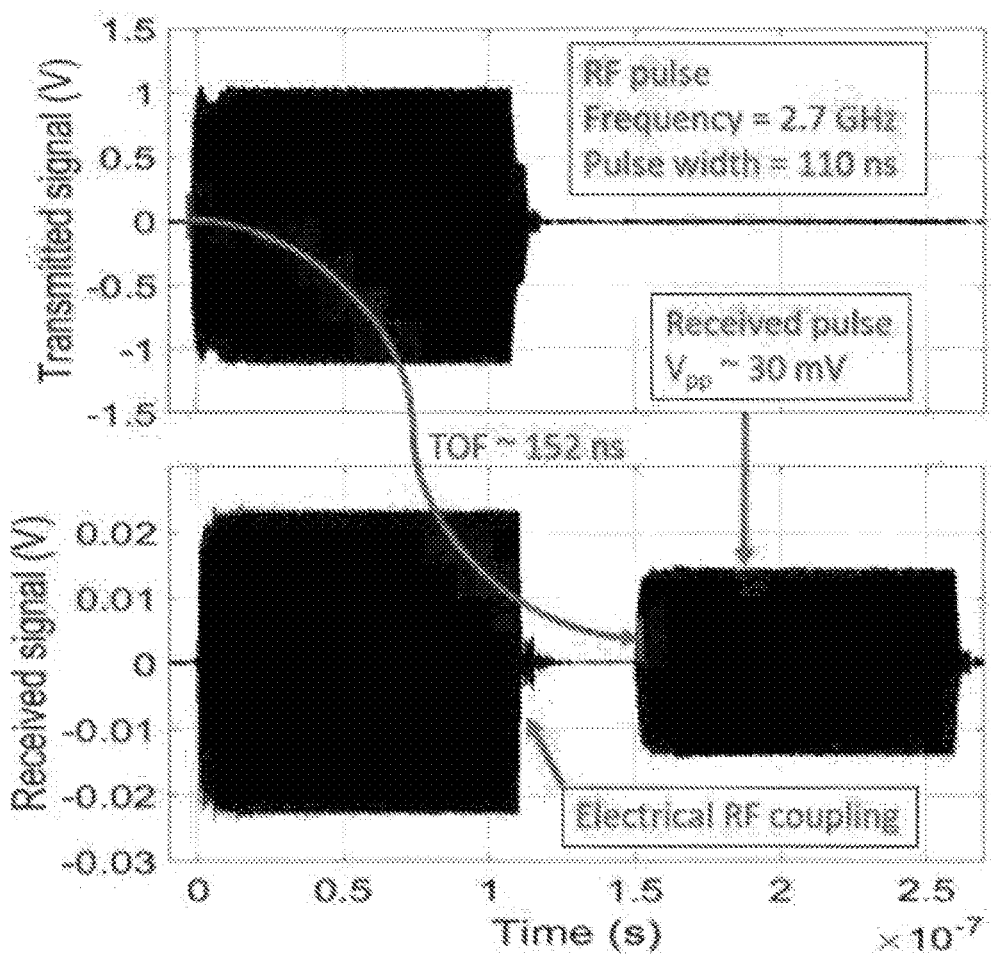
FIG. 14A shows data plots depicting the measured transmitted and received electrical signals using an example ultrasonic transceiver temperature sensor device.
Figure 14B:
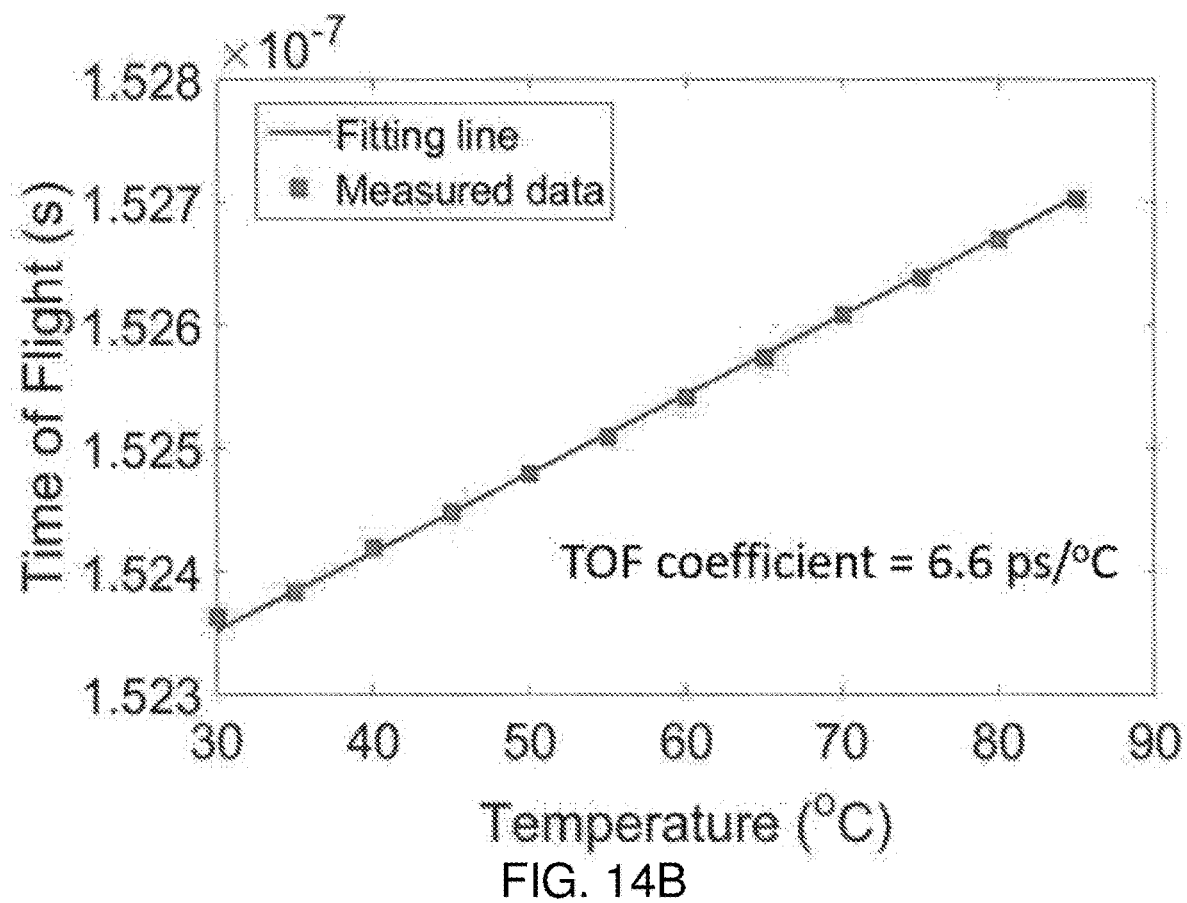
FIG. 14B shows data plots depicting the time of flight change versus temperature relationship using an example ultrasonic transceiver temperature sensor device.
Figure 14C:
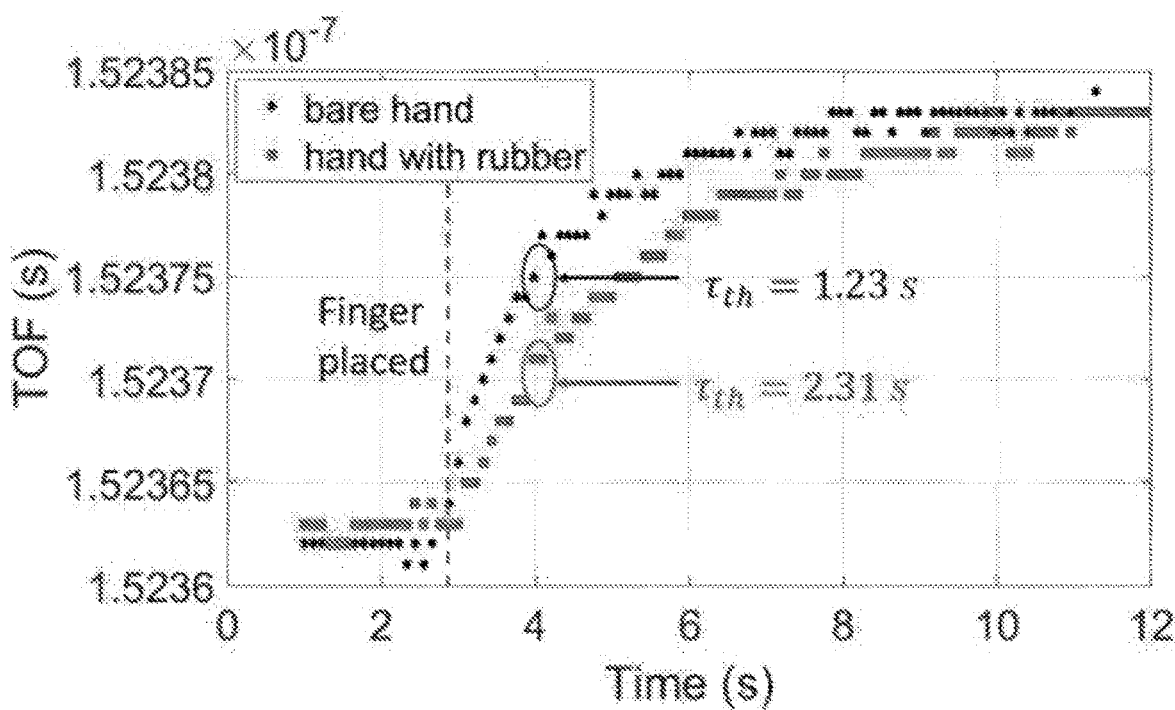
FIG. 14C shows data plots depicting the difference in thermal time constants between a bare hand and rubber gloves in contact with an example ultrasonic transceiver temperature sensor device.

FIG. 14A shows data plots depicting the measured transmitted and received electrical signals using the system 1300. The transmit transducer was excited by an RF pulse of amplitude=1 V. The first pulse in the received signal was due to electrical RF coupling between the transmitter and receiver pads. The second pulse is the received signal after one round trip through the silicon substrate. Attenuation is due to electromechanical coupling loss at both the transmitter and the receiver, diffraction, and electrical impedance mismatch between RF switch output and transducer input and between the transducer output and the oscilloscope input. Typical output received signal amplitude is 15 mV. TOF is measured between the transmitted pulse and the received pulse. At room temperature, TOF=152.3 ns.

The acoustic velocity is given by $$v = \sqrt{\frac{E}{\rho}},$$

where E is the stiffness of the material and $\rho$ is its density. For acoustic waves propagating perpendicular to the (100) Si wafer plane, the stiffness coefficient decreases linearly as temperature increases with a temperature coefficient of −78.8*10-6 Pa/° C. Hence, the temperature coefficient of speed in silicon is −39.44 ppm/° C. The thermal expansion coefficient of silicon is 2.6 ppm/° C. The TOF as a function of temperature is given by equation (7):

$$TOF = \frac{t_s(1 + \alpha\Delta T)}{C(1 - |\beta|\Delta T)} \qquad (Eq. 7)$$

where $\alpha$ is the thermal coefficient of expansion, $\beta$ is the thermal coefficient of speed, $t_s$ is the silicon thickness, and C is the speed of sound in silicon. According to equation (7), the TOF of the acoustic signal in silicon vary linearly with temperature with a thermal coefficient of 6.65 ps/° C. To verify this coefficient, the example device 610 was placed on a hot plate. The temperature of the hot plate is gradually elevated while measuring the change in the TOF. The result, shown in FIG. 14B, proves the linear dependence of TOF on temperature and the measured coefficient is 6.6 ps/° C. which agrees with the predicted value.

To test the ability to measure thermal properties of the contacted materials, comparison in the change in TOF of a bare finger in contact with the sensor versus a finger covered with a rubber glove is conducted. As shown in FIG. 14C, the time constant in case of bare hand contact is higher by 1.08 sec compared to the case with the rubber gloves (e.g., corresponding to model values in FIG. 10C). Similarly, the sensor can differentiate between different materials based on their different thermal conductivity and heat capacity.

These example results show that the ultrasonic transceiver temperature sensor device can distinguish between a bare hand and a hand with rubber gloves by measuring the thermal time constant. For example, the gloves act as a thermal isolator causing lower thermal conductivity and higher time constant. Analysis shows that the sensor can identify different materials like silicon and glass based on their thermal conductivity and heat capacity. These example results demonstrate that the sensor can be used in different applications, e.g., like in a robot hand to detect different materials, and in manufacturing to monitor material properties during the manufacture process.

In various embodiments in accordance with the present technology, the ultrasonic transceiver sensor devices can be configured with data transmission and processing capabilities. For example, in some embodiments, the synthetic sensing membrane 400 including an individual or a plurality of the ultrasonic transceiver sensor devices 410, 510, and/or 610 can be configured to include one or both of wired and wireless data transfer from the sensors. For example, the wired configuration can include a pathway to a processing unit, to process the signals demonstrating the sensor chip capabilities.

Example ultrasonic transceiver temperature sensor chips can collect pixel imaging data and TOF data. For example, with a 100-pixel array, with two 8-bit bytes per pixel for intensity and two 8-bit bytes for TOF, each "image" can include 400 bytes. Each chip can also have two or more address bytes to identify the chip. For example, with handshaking overhead, the data rate can be 500 bytes per frame. For example, assuming a wired data link over a low power serial data interface at 20-Mbit/s, it will take about 0.15-ms of time. If the sensor surface is to operate at least as fast as physiological rates, an entire surface may be read within tens of milliseconds. In other words, in this example, a membrane including 50 chips can be read during one response time. Multiple banks of 30 chips can be read by adding parallel data acquisition serial buses.

The power consumption in driving long wires over a flexible surface can be addressed using low-voltage differential sensing (LVDS). For example, LVDS receivers interfaced to micro-controllers can be used for communications. For example, both RF and wired interfaces can be implemented in CMOS designs, reducing parasitics, and fine tuning for specific sensor parasitics, to further increase bandwidth and reduce power. For the wired sensor interface, for example, the chips can be placed on a 3-wire interface to get this data. Within each chip, the power consumption can include ultrasonic transmit power, receiver power, digital circuits to interface the data.

Table 1 shows example applications of the synthetic sensing membrane 400 for various measurements, including in connection to robotics.

TABLE 1

| Measurement | Physical variable | Connection to Robotics |
| --- | --- | --- |
| Lines of protrusion | Surface topology | Material type |
| Imaged line expansion | Contact force versus time | Grip strength and speed |
| Return signal strength | Material sonic impedance | Contact material type |
| Return signal versus frequency | Ultrasonic loss dispersion | Contact material type |
| Time-of-Flight (TOF) | Speed of sound | Object Temperature |
| Time-of-Flight (TOF) versus time | Speed of sound | Object Thermal conductivity |

Implementations of the synthetic sensing membrane 400 including an individual or a plurality of the ultrasonic transceiver sensor devices 410, 510, and/or 610 can be used for the various applications to measure force, dispersion, temperature, and thermal conductivity of the touched object and/or generate an image of the object in contact.

In some implementations, an integrated circuit design of the ultrasonic transceiver sensor chips and synthetic sensing membrane can include a processing circuit including phase controller circuits, RF amplifiers, RF-Pads, RF T/R (transmit/receive) switches, high frequency TIA amplifiers for PAD capacitance limited AlN pixel measurement, RF-switches, digital delay elements, and many biasing circuits. In some implementations, the performance of the ultrasonic transceiver sensor chips and synthetic sensing membrane can be modeled using PZFlex and COMSOL simulation environment, which allows ultrasonic simulations, including special zero energy reflectance elements required for ultrasonic wave propagation simulations. In some implementations, for example, the package can be run on a server to handle 1-million plus element simulations, which can assist in design of sonar actuation and sensing timing requirements.

In some implementations, the hard polymer layer (e.g., PVDF) can be electro-sprayed using an electrospray system, e.g., SYBASE, and various recipes to electrospray polymers onto silicon micromachined surfaces, and silicon covered by photoresist. In some implementations, fabrication of the example ultrasonic transceiver sensors can use a laser cutter (e.g., LPKF Laser Cutter for PZT stages) to cut through silicon and PZT wafers, which can also be used to make PZT actuators and motion stages. In some examples, using a x-y-z stage, tweezers can be formed to manipulate and place the chiplets onto interposers.

Other techniques and equipment for producing and/or characterizing the ultrasonic transceiver sensor chips include a nanofabrication platform including, for example, e-beam lithography, 5 nm stepper lithography tools (e.g., for down to 100 nm exposure), multitudes of plasma and LPCV deposition tools for MEMS fabrication, and DRIE tools for through-wafer etching. Example AlN processing techniques can be used to develop the piezoelectric transceiver technology at chip-level can be characterized using SEMS, FIB, XRD tools, e.g., characterize piezoelectric AlN films before and after processing steps.

Various signal analysis techniques can be implemented. In some implementations, a spectrum analyzer can be used for signal analysis, e.g., such as a Polytec MSA-400 Micro System Analyzer, to characterize low frequency sonic measurements for cases where AlN structures with resonances up to 20 MHz. In some implementations, a Doppler interferometer that can operate up to 4 GHz owing to a 2 GHz electro-optical modulator (e.g., 4-GHz Doppler optical femtometer resolution interferometer) can be used for measuring femtometer displacements and allow measurements of ultrasonic surface ultrasonic amplitudes, e.g., to confirm modeling and analytical models of the example devices. In some implementations, sonar testing can be conducted using GHz Oscilloscopes and Function Generators (e.g., MSOV164A family 20 GHz scopes, and 3 GHz function generators, and customized RF filters and diagnostic equipment), including using an example Keysight M8195A 25 GHz arbitrary waveform generator to conduct pulse sequence testing on sonar elements.

Implementations of the disclosed technology can be used for a variety of applications. Some examples include applications requiring surface topology measurements, such as in robotic handling of objects, where it is important to measure the topology to determine the friction force during contact, and it is advantageous to know the material being handled to know the limits of forces applied to the object. Another example, is the requirement of measurement of surface roughness after fabrication of an object using numerous fabrication approaches such as 3D printing, or traditional machining.

Example Application: Soil Integrated Gigahertz Ultrasonic Imager Devices, Systems, and Methods As the need for energy needed by the world continues to increase, the need for biofuels continue to increase. Inefficiencies in biomass production can affect cost competitiveness with alternative energy sources, and require the use of additional precious natural lands, converting them into farms. Natural resources such as water are becoming even more scarce due increased consumption in farming. The leaching of pesticides into underground water tables has significant health risks for the general public.

One of the main criticisms of biofuels is that increasing demand for plant feedstocks for bioethanol or biodiesel is diverting valuable land and resources away from other purposes. As many biofuel feedstocks such as soybeans, corn, and palm oil also play an important role in the food supply, many critics are concerned that the diversion of some of these crops for biofuel will reduce the food supply and increase food costs. As an example of what could be more to come in the future, food riots that were partly linked to the reduction of food supply due to increased demand for biofuels erupted in Haiti in 2008.

In addition to concern about a reduction in food supply, there is also criticism that increasing need for biofuels may result in increasing deforestation, thereby negating the much-touted "carbon neutrality" benefit of biofuels. For example, there is increasing evidence that the increasing need for farmland to grow sugar cane in Brazil for bioethanol and palm oil in Malaysia and Indonesia for biodiesel has resulted in deforestation in those countries. Rapid deforestation has been known to cause rapid release of carbon dioxides stored in the soil, negating the positive attributes of biofuels reducing $CO_2$ emissions.

As such, to address these food supply and environmental concerns, it is important to reduce the amount of cropland or forests that are being diverted to grow biofuel feedstock crops, while simultaneously meeting the growing demand for biofuel. One approach to address this issue is to develop new technology to increase crop yields so that each parcel of farmland used for growing biofuel feedstocks can become much more productive and efficient. One way to increase crop yields and therefore farmland productivity is through the use of site specific crop management, also known as precision agriculture or "smart farming". Crop yields are prevented from reaching their full yield potential due to a variety of factors such as the availability of water and nutrients and the presence of pests and diseases.

Numerous types of crops may be used as biofuel feedstocks—these include corn, soybean, sorghum, sugarcane, canola, palm oil, wheat, sugar beets, and cassava. The vast majority of the U.S. bioethanol supply is derived from corn. In 2016, 5.28 billion bushels of corn, which amounts to 36% of U.S. corn production supply, was used for ethanol production. For biodiesel, on the other hand, soybean is the most important crop—in 2017, 6.23 billion pounds of soybean oil were used as biodiesel feedstock, along with 1.5 billion pounds of corn oil. While soybean and corn are the principal crops currently used for biofuel production in the United States, bioethanol production is primarily derived from sugar beets and wheat in the E.U., and from sugar cane in Brazil.

One pest that is of great economic importance to the biofuels market is the plant parasitic nematode, a family of microscopic worms that typically range in width from 5 μm to 150 μm, and in length from 300 μm to 6 cm. There are numerous species of nematodes that feed upon different crops. For example, the sugar beet nematode, *Heterodera schachtii*, parasitizes the roots of sugar beets thereby stunting plant growth, killing seedlings, and causing wilting or yellowing of plant leaves.

As can be seen from Table 2, all of the primary biofuel feedstock crops mentioned earlier are vulnerable to predation from nematodes, resulting in billions of dollars of economic loss each year.

Table 2 shows an estimated yield loss and monetary loss in the United States in 2008 from nematodes on biofuel feedstock crops.

TABLE 2

| Feedstock | Estimated Yield Loss in 2008 | Estimated Monetary loss in 2008 |
| --- | --- | --- |
| Corn | 10.20% | 14.85 Billion |
| Soybean | 10.60% | 2.02 Billion |
| Sugar beet | 10.90% | 1.26 Billion |
| Sugar cane | 15.30% | 8.46 Billion |

The soybean cyst nematode, in particular, is the number one cause of soybean yield losses. For farmers growing sugar beets, nematodes can cause yield losses from 10% to 80%. In addition, there is evidence that *Miscanthus* and switchgrass, which are being considered as "next-generation" biofuel feedstocks, are vulnerable to plant parasitic nematodes, although the exact economic impact is yet to be determined.

Damage from nematodes is often difficult to diagnose, because the symptoms that are visible from the above ground portion of a plant are not unique to nematode damage, and therefore are often mistakenly attributed to other sources, such as nutrient and moisture deficiencies. For soybean cyst nematodes, the only way to tell is to inspect the roots of a plant carefully for the presence of nematodes and small cysts on the plant roots. To determine whether or not to apply nematicides to control the nematode population, growers must take soil samples, typically after harvest, from the root zone of the soil, which is typically 20 cm deep, but may be up to 60 cm deep for some deep growing plants. The amount of samples to be taken is typically around 20 samples per 25 acres. The samples are then sent to a lab to determine nematode populations. As the nematode sampling process can be time and labor intensive, particularly for large farms, there have been on-going efforts to develop sensor systems to detect nematodes. There has been some success on identifying the presence of various symptoms associated with nematode damage on sugar beets by using image processing on camera images and spectroscopic measurement of leaf reflectance from sensors deployed on both the ground and on UAVs. However, the downside of this method is that damage to plants must already have occurred in order for the symptoms to be visible and detectable from above-ground sensors.

Therefore, in addition to above-ground imaging, what is desired is a sensor that can monitor nematode populations, and their effect on the roots, within the soil in real time such that a farmer would be able to determine whether or not to apply nematicides before any crop losses have been incurred. As nematodes have low mobility and their populations are concentrated in patches, such a sensor must be cheap enough and small enough such that large numbers of sensors can be deployed on a farm. Such a sensor can measure not only the nematode population, but also measure the rate at which roots, by imaging the root size and surface morphology, over time. State of art sensors that can measure root growth are still in the academic settings, and not commercially available. These methods include CT scanning, direct optical imaging, optical coherence tomographic methods, MRI imaging. Most of these methods have been used in the lab, limited largely by the fact that the sensors are too bulky and high power consuming to be able to operate below ground for long periods of time.

Disclosed are soil integrated ultrasonic imager devices, systems and methods, which can be implemented for target water and pesticide delivery biomass production.

The disclosed technology aims at reducing the use of water and pesticides, while providing pathways to improve biomass productivity. Implementations of the disclosed devices, systems and methods can provide an inexpensive multisensory sensor-node that can image water content, chemical properties of the soil, root growth, and nematode pests in soil near the surface of the sensor chip. This unprecedented degree of integration of sensing and imaging can provide a low-cost solution to precision sensor-based digital agriculture. The example subsurface imager system would provide valuable information on plant growth below the ground, complementing data being acquired by above-ground approaches such as aerial image collection. The sensor node can be recycled for future crops by removing it from the soil during harvesting, and the business model of providing sensors as a service can be economically viable while adding to the profitability of the biomass production value chain. Implementations of the disclosed technology can include CMOS-integrated ultrasonic wave pulse reflectometry from an array of ultrasonic transducers that can sense the water content, salinity, temperature changes, motion of pests such as nematodes, and slowly changing root growth around the sensor surface. The example sensor chip can include the sensors and an RF interface that can communicate to above-ground farm vehicles or robotics. By including ultrasonic imaging, energy harvesting, and low-power wake up receivers, the disclosed devices, systems and methods can address the energy challenge of increasing biofuel effectiveness.

Figure 15A:
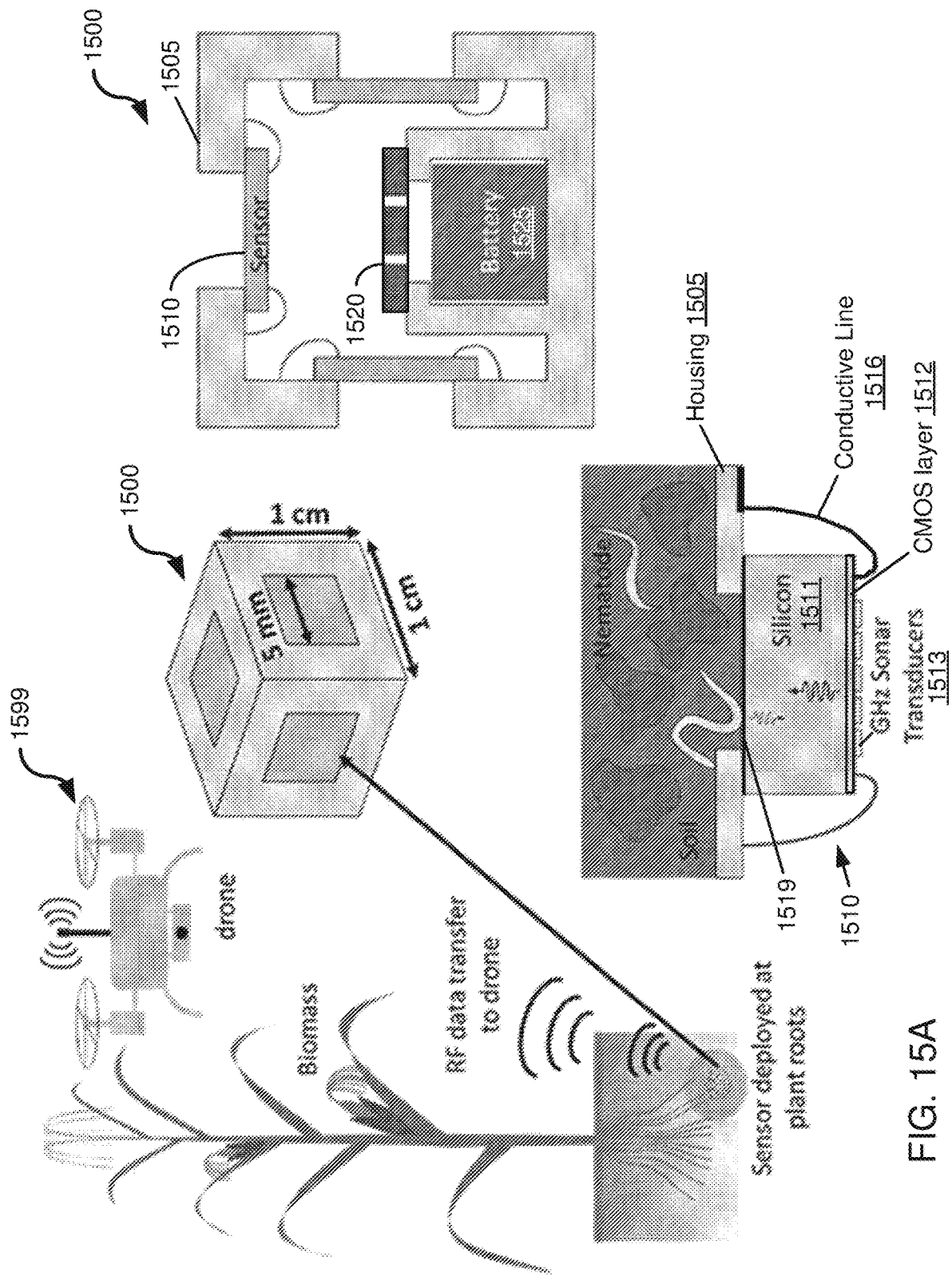
FIGS. 15A and 15B show example embodiments of an ultrasonic soil condition sensor device for assessing various conditions that can affect soil and plants growing therein.

FIG. 15A shows an example embodiment of an ultrasonic soil condition sensor device 1500, which includes ultrasonic sensing surfaces and powered to be deployable in the soil for assessing various conditions that can affect soil and plants growing therein. In this example, the ultrasonic soil condition sensor device 1500 is configured in a cubic shape, also referred to as the "sensor cube", but could also be configured in a variety of other shapes, including pyramidal, hexagonal, octagonal or other polygonal shapes. In some examples, the sensor device 1500 can include curved shapes, e.g., as the semiconductor substrate can be etched to accommodate curved surface interfaces with the soil. Similarly, the size of the ultrasonic soil condition sensor device 1500 can vary and be tailored for the particular application of the device. In implementations, for example, the ultrasonic soil condition sensor device 1500 includes an ultrasonic transceiver sensor device 1510 in accordance with the disclosed embodiments described herein (e.g., embodiments of the transceiver sensor chip device 410) in communication with a data processing and/or communications unit, e.g., like an RF transceiver. The ultrasonic transceiver sensor device 1510, also referred to as the ultrasonic imaging sensor device 1510 or ultrasonic imager device 1510, is operable to transmit and receive the acoustic signals at frequencies of at least 0.5 GHz within a bulk semiconductor substrate for detecting and imaging an object in contact with the sensing surface within the soil and/or changes in conditions of the soil proximate the sensing surface. The acoustic signals can be processed and transmitted from the ultrasonic soil condition sensor device 1500 through the soil via wireless communications, such as by radio frequency (RF) signals. The example shown in FIG. 15A is that of a 1×1×1 cm$^3$ cube with six sensor surfaces having (e.g., having 5×5 mm$^2$ surface area for detection. The ultrasonic soil condition sensor device 1500 is configured to communicate with an external receiver 1599 such as an unmanned aerial vehicle (UAV, or "drone"), base station, land vehicle or robot, etc., in order to transmit the collected ultrasonic data or processed ultrasonic images of roots and nematodes, and physical parameters.

The ultrasonic soil condition sensor device 1500 includes a housing 1505 that includes one or more openings into a hollow interior region, in which one or more ultrasonic imaging sensor devices 1510 is positioned in the housing 1505, such that the sensing surface of the sensor 1510 is outward facing from the opening and the sensor device 1510 is secured to a wall of the housing 1505. The ultrasonic imaging sensor device 1510 can include features of the example embodiments of the ultrasonic transceiver sensor device 410. As shown in FIG. 15A, the ultrasonic imaging sensor device 1510 includes a substrate 1511 (e.g., silicon) in which a CMOS layer 1512 is attached to one side of the substrate 1511 and an array of piezoelectric transducers 1513 are coupled to the CMOS layer 1512. The ultrasonic imaging sensor device 1510 includes a contact layer 1519 having a hydrophilic surface that is attached to the opposite side of the substrate 1511. The contact layer topology 1519 can also provide a hydrophilic/hydrophobic interface to attract biological subjects such as nematodes and roots, for example. In some embodiments, for example, the hydrophilic surface of the contact layer 1519 includes an array of protrusions (e.g., nanopillars of 10-20 nm of height). In implementations, many approaches can be used such as texturing the surface to create different hydrophilic or hydrophobic interfaces. An example includes a 10-20 µm thick PDMS layer, with patterned gold films. Another example includes the silicon substrate itself that is textured to produce the hydrophilic/hydrophobic interface, e.g., which can be textured using laser ablation approaches with the laser ablation parameters controlling the average aspect ratio of the roughened surface. The hydrophilic surface of the contact layer 1519 provides a surface for contact with the external object, and attracts moisture and living organisms in the soil for sensing applications.

In some embodiments, the device 1500 includes a conductive line 1516 that electrically connects the CMOS layer 1512 of the sensor 1510 to the data processing and/or communications unit 1520. For example, the conductive line 1516 can run on an interior surface or within the wall of the housing 1505 between the one or more ultrasonic imaging sensors 1510 and the data processing and/or communications unit 1520 of the device 1500.

As shown in FIG. 15A, the example sensor cube can be deployed in the soil in the root zone of a plant such that it is situated where nematode population is maximum. The example ultrasonic soil condition sensor device 1500 includes a plurality of sensor nodes, comprising the ultrasonic imaging sensor chip device 1510, arranged on faces of the device 1500 such that one or more sensor nodes can be placed near the roots of the plants. In the example of the sensor cube shown in FIG. 15A, on each side of the cube there is an example ultrasonic imaging sensor 1510. In some embodiments, the ultrasonic soil condition sensor device 1500 is self-powered (e.g., via battery or fuel cell) and includes a wireless transmitter and/or receiver (Tx, Rx, or Tx/Rx) unit able to communicate to an outside receiver, such as the example receiving unit 1599. In this manner, the device 1500 is able to be placed below the surface such that no wires are needed to come outside of the soil, and is battery powered, e.g., with battery lifetime of at least a year. In some implementations, the ultrasonic soil condition sensor devices 1500 can sense the surfaces of their surroundings to intermittently and/or continuously monitor soil parameters, possible parasites, and reactions with neighboring plant life, where the collected data is saved and/or transmitted once every hour to monitor the slow changing parameters around the sensor. In some implementations, for example, before plant harvest, the device 1500 can be removed for re-use in the next crop cycle.

In some implementations, the soil condition sensor device 1500 can include a low-power-consuming receiver (e.g., <1 microwatt) that waits for a wakeup signal from a RF radio. This radio can be situated on a UAV drone, for example, that patrols the farm periodically. When it comes close to the sensor device 1500, the example UAV can transmit a RF wakeup signal that will turn on the sensor unit so that it will transmit the sensor data. The data can then be transmitted to the cloud from the UAV. The UAV can then go to the next sensor device 1500 and repeat the process of data collection and relay. For example, the multiple sensor devices 1500 can be placed at spatial densities, e.g., on the order of 1-3 sensors/10 m². In some embodiments, the power unit of the ultrasonic soil condition sensor device 1500 can be wirelessly charged. During the interrogation, for example, the UAV can potentially also charge the battery through RF wireless power transfer. The RF communication through soil is favorable at lower frequencies, e.g., due to lower loss resulting in higher power requirement for communications. However, lower frequencies entail longer wavelengths, which can make antenna design impractical. Hence, a tradeoff between size and loss generally favors frequencies of the example RF transmitter/receiver unit in the 200-400 MHz range.

Figure 15B:
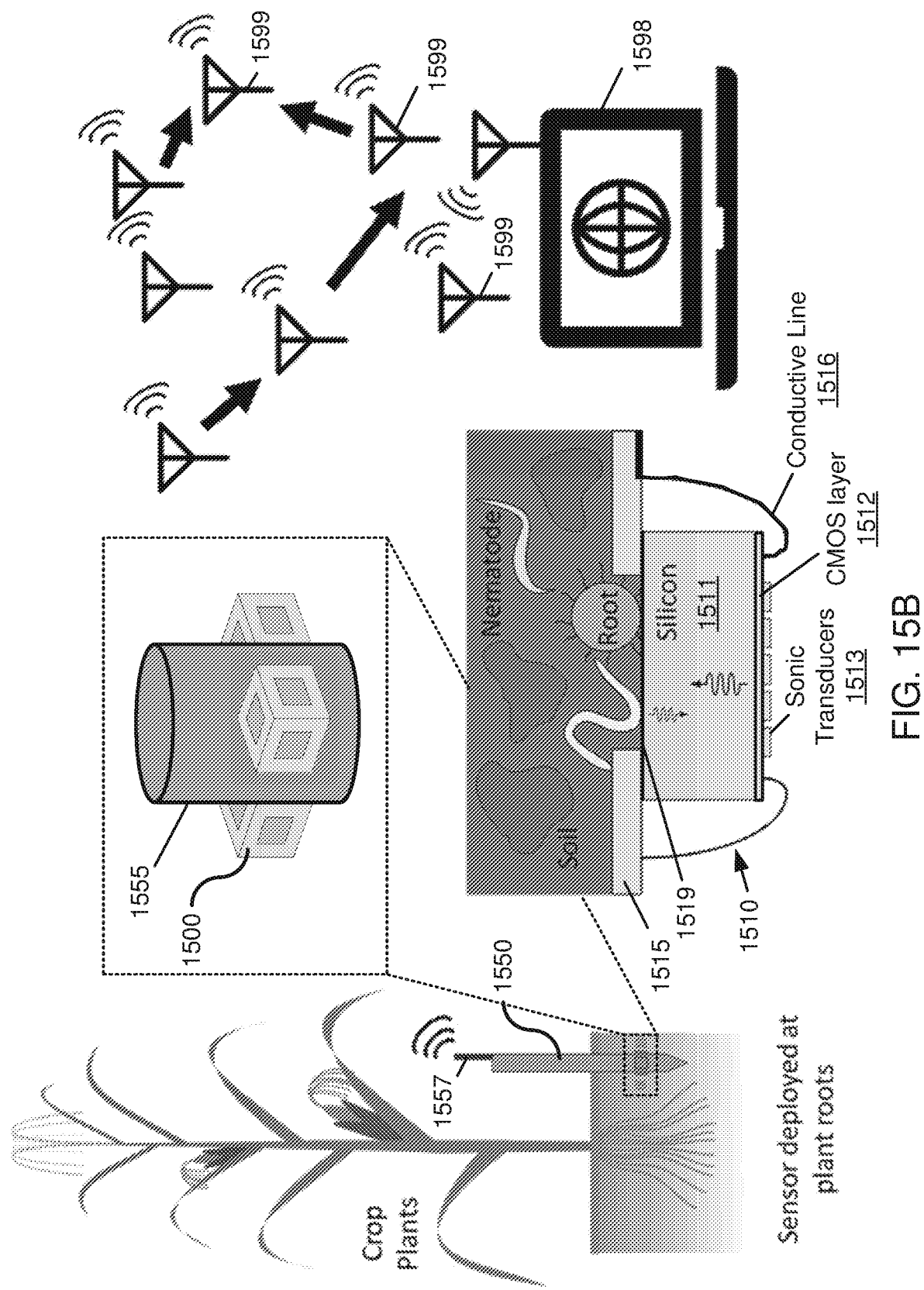

FIG. 15B shows an example embodiment of the ultrasonic soil condition sensor device 1500 attached to a wireless communication soil stick 1550. In this example, the wireless communication soil stick 1550 includes a shaft structure 1555 that facilitates attachment and/or integration of one or more ultrasonic soil condition sensor devices 1500 such that the sensing surface of the sensor 1510 is outward facing from the shaft structure 1555. For example, the shaft structure 1555 can be an elongated, rigid structure with a portion of the interior hollow to encase (e.g., fully or partially) the one or more ultrasonic transceiver sensor devices 1510 and data processing and communication unit 1520. The shaft structure 1555 can be configured in a variety of shapes, e.g., including cylindrical, conical, rectangular or other. In some embodiments, the one or more ultrasonic transceiver sensor devices 1510 can be positioned toward one end of the shaft structure 1555 configured to penetrate into the soil; whereas in some embodiments, a plurality of ultrasonic transceiver sensor devices 1510 can be arranged in multiple rows along the shaft structure 1555 to allow for measurements along varying depths within the soil. The wireless communication soil stick 1550 includes one or more antennas 1557 at an opposite end of the shaft structure 1550 from that which penetrates into the soil. The one or more antennas 1557 is connected to the transceiver of the data processing and communications unit 1520 of the ultrasonic soil condition sensor devices 1500. For example, in some embodiments, the data processing unit and communications unit 1520 includes a microcontroller which includes memory, calculation capabilities, conversion of analog to digital and digital to analog capability, and ability to communicate to other units though data busses, such as a SPI bus. A radio transceiver can be separate PC-board implementation using COTS transceiver chips that take in digital data to transmit and produce digital data read in from the RF antenna.

In some embodiments, the data processing and communication unit 1520 of the ultrasonic soil condition sensor device 1500 can be disposed within an interior cavity of the shaft structure 1555. For example, in some embodiments, the conductive lines 1516 from the ultrasonic soil condition sensor devices 1500 electrically connect to a centralized data processing and communication unit 1520. In some embodiments, the data processing and communication unit 1520 is decentralized for each ultrasonic soil condition sensor devices 1500 in the soil stick 1550.

As illustrated in FIG. 15B, the one or more ultrasonic soil condition sensor devices 1500 attached to the wireless communication soil stick 1550 can wirelessly communicate with the external receiver 1599 via the antenna 1557 to transmit the collected ultrasonic data or processed ultrasonic images of roots and nematodes, and physical parameters. For example, the external receivers 1599 and wireless communication soil stick devices 1550 can communicate with a central or main control computer 1598 by a network of external receivers 1599 placed along the land being monitored.

FIGS. 16A-16C shows a diagram illustrating an example ultrasonic sensor node that can be placed below the seeds and the plant will grow over the seed with roots covering the sensor. For example, GHz sonic imaging (e.g., 0.5 GHz or greater) can image moving nematodes and root growth rates. GHz ultrasonic sensing can also be used to measure temperature, thermal conductivity, ionic concentrations by ultrasonic pulse reflectometry.

FIG. 16A illustrates how an example ultrasonic imaging sensor device 1500 can be placed below seeds so that the plants grow over the sensor box, with the roots growing around it. For example, roots are likely to grow on the surface or in close proximity (e.g., <100 μm) to the sensor surface. The nematodes that feed on the roots are most likely to be near the roots and come near the surface of the sensor. The ultrasonic beams, formed by individual large transducers or a phased array of transducers send pulses at the surfaces (as illustrated in FIG. 16B) and measure spatial and temporal changes by the return signal indicative of the ultrasonic impedance (as illustrated in FIG. 16C). As shown in the diagrams of FIGS. 16B and 16C, the sonic phased arrays of transducers are coupled to CMOS electronics and a semiconductor substrate to transmit and receive ultrasonic signals for imaging of objects in contact with the sensor surface (e.g., with 1-5 μm resolution). The CMOS electronics arc operable to control the phased arrays of transducers and can be configured to perform complementary computations. Changes in the ultrasonic reflectance on the order of the travel time of nematodes can then indicate the presence of the pests, and time varying changes in the shape of roots can be indicative of root growth rates. This scanning of the surface can be done every few minutes, to hours, to one per day, to conserve energy. In some implementations, machine learning techniques to ascertain nematode population from many sensors across the farm can be used to determine the extent of nematode population and need for pesticides.

Table 3 shows a list of example variables that the GHz scanning (e.g., 0.5 GHz or greater) can be used to measure.

TABLE 3

| Biomass yield variable | Existing state-of-art (SOA) methods | Problems with SOA methods | Example proposed approaches | Advantage of proposed activity |
| --- | --- | --- | --- | --- |
| Root growth rate, root phenotyping | CT scanning, PET, OCT, optical imaging, MRI | Very high size, weight, and power, mostly for research | GHz ultrasonic imaging of surface of root over time | Low SWAP, all six direction imaging |
| Nematode population and phenotyping | Sampling of soil and counting nematodes under microscope | Time and labor intensive for entire farm measurement | GHz ultrasonic surface to visualize slow moving nematodes in close proximity to sensor unit | Continues tracking with time to infer types and mobility of pests in soil |

TABLE 3-continued

| Biomass yield variable | Existing state-of-art (SOA) methods | Problems with SOA methods | Example proposed approaches | Advantage of proposed activity |
|---|---|---|---|---|
| Soil moisture | RF or DC electrical impedance | Electric potential electrodes corrode over time | GHz ultrasound can measure sonic loss in soil, strong function of water content | Self-calibrating due to reflection from top surface |
| Temperature, thermal conductivity of sample | RTD, thermocouples, thermistors | Thermal conductivity is hard to measure | GHz ultrasonic time-of-flight can measure temperature gradients | Self-calibrating sensing and thermal conductivity measurement |
| Salinity, ionic concentrations | Ionic electrical conductance systems with RF and DC voltages | Signal function of local conductance | GHz loss due to ion concentrations by modulation RF field | Self-referencing of ion motion induced by local RF fields can be measured |

In some implementations, as illustrated in FIG. 16B, roots can be imaged by collecting data indicative of the change in root(s) coming in contact with the sensor surface and growing over time. The reflected signals from scanning US pulses will be a function of the absorption into the root versus soil, which have very different acoustic impedances and absorption. While there are challenges associated with the spatial extent of sensing being limited to the sensor surface, local variations of one volume of soil near the plant root system is likely to good indicators of the plant health. Greater amounts of information can be achieved by increasing the surface areas of the sensor units, for example, by making each sensor cube bigger or placing many sensor cubes per plant.

Similarly, in some implementations, as illustrated in FIG. 16B, the disclosed ultrasonic sensor devices can be used for imaging nematodes. Present techniques for imaging nematodes require collecting samples and quantifying under microscope. In contrast, the disclosed ultrasonic sensor devices and methods can yield continuous sampling of the same volume of soil, providing a time history that is not irreversibly destroyed by physical removal of the soil sample. The disclosed techniques allow identification of the type of nematodes based on changes in the ultrasonic impedance spectra over different carrier frequencies. After gathering data from many nematode signatures, maps of nematode populations can be studied (and population explosions can be identified, e.g., well before the symptoms showing on above ground images), which can enable precision delivery of very small amounts of pesticides, minimizing the need for blanket pesticide use. In some implementations, the sensor node itself can contain pesticides that can be released as needed.

In some implementations, the disclosed ultrasonic sensor devices can be used for soil moisture measurements. Soil moisture measurement is extremely important to prevent optimal plant growth, especially as a function of ambient temperature and humidity levels. The irrigation resources can be controlled to provide optimal watering levels, from developing a cloud computing model in which the moisture data can be combined with ambient and soil temperature data, and ambient humidity levels. Local variations in soil porosity can result in spatial moisture variations which can be identified by the areal distribution of the sensor nodes. Soil porosity can be determined by the changes in moisture levels over time post irrigation events, which the example ultrasonic sensor device can measure. For example, GHz pulses (e.g., of frequencies 0.5 GHz or greater) will undergo different absorption in soil as a function of moisture as the coupling and absorption of the pulses from the sensor chip will be a function of the soil moisture.

In some implementations, as illustrated in FIG. 16C, the disclosed ultrasonic sensor devices can be used for soil ionic concentration measurements. Soil ionic concentrations are important for plant growth, and today can be measured using DC and RF measurements of soil conductivity. Ionic concentrations are indicative of soil salinity, pH, and acidity, all can affect the plant growth in complex pathways. While current approaches are capable of obtaining some measurements, issues with electrode aging due to chemical reactions with soil can add variations in electrode performance which can confounded actual data on conductivity being measured. The example ultrasonic sensor devices can use RF voltages penetrating through the soil sample to modulate the ion populations using ionic mobility. The GHz sonic pulse absorption is a function of the ionic concentrations and can be seen to change as result of RF induced ion motion. This pump (RF modulation of ion species) and probe (measurement of ion induced sonic propagation parameters) allows for the common mode elimination of effects on ultrasonic pulses due to temperature and soil conditions.

Energy analysis of an example system. The disclosed devices, systems and methods can include very low power wakeup radios (e.g., 1 µW) based on pure CMOS and CMOS-MEMS solutions. The following describes some example system components that can be used in conjunction with the example ultrasonic soil condition sensor device.

For a 10×10 imaging array of 100 transducers, each with capacitance of 100 fF, the energy required to drive a transducer is dominated by the energy required to charge the capacitance of the transducers. A single 10 mW set of receive amplifiers is shared between all of the transducers. Assuming a 1 mm×1 mm area is to be scanned in 25 µm increments, 1600 measurements need to be made, resulting in a total scan energy of 80 microjoules. A 2 cm diameter CR2032 coin cell battery can be used. A 1 Mbps, 1 W RF transmitter is assumed in the calculation—the transmitter power does not need to be very large because the data will not be transmitted over large distances due to the use of a drone. As the drone will send a wakeup signal to the sensor node, the RF receiver for the node does not need to be on all the time—instead only a 1 μW wake-up switch needs to be on. For the microcontroller controlling the GHz ultrasonic scanning, 5 mW power consumption and 5 μW sleep leakage current are assumed, which are typical specs for low power MSP430 microcontrollers. From Table 5, it can be seen that this system can operate for over 1 year before the battery needs to be replaced, which is longer than a single growing season. Hence, a service-based business model where the devices are installed and removed by a service personnel can be possible. For example, UAVs to take data can be paid for by a service company.

Table 4 shows the power consumption of components of an example embodiment of the system in an example implementation.

TABLE 4

Single pulse generation energy

| | | |
|---|---|---|
| 10 × 10 array of AlN transducers | 100 | transducers |
| Total capacitance | 1E-11 | F |
| Volatage | 1 | V |
| Transducer energy | 5E-12 | Joules |
| Transmitter efficiency | 20% | |
| Transmitter energy | 2.5E-11 | Joules |
| (Rf and ADC) Receiver power | 10 | mWatt |
| Time of receiver on | 5.00E-06 | seconds |
| Receiver Energy | 5.00E-08 | Joules |
| Area to be scanned | 1 × 1 | mm |
| sample area size | 25 | um |
| Number of sample points | 1600 | |
| Total scan energy | 8.00E-05 | Joules |
| Coin CR2032 Battery capacity (3 V to 2 V) | 235 | mA-Hr |
| Battery voltage (nominal 3 V, assume 2.5 V) | 2.5 | V |
| Total Joules | 2115 | Joules |
| RF transmitter power | 1.00E+00 | Watt |
| Bits per sample area | 16 | |
| Bits for all 6 sides (80% bit efficiency) | 4.61E+06 | bits |
| Data rate | 1 | Mbit/s |
| Time of transmission (receiver and transmitter) | 4.608 | seconds |
| Energy per transmission | 4.61E+00 | Joules |
| RF Receiver power | 10 | mW |
| Wakeup radio power | 1000 | nW |
| Microcontroller power | 5 | mW |
| Time of one scan | 8.00E-03 | seconds |
| Number of scans one per day | 24 | |
| Number of surfaces | 6 | |
| Leakage power for uC | 5.00E-06 | Watts |
| Leakage energy per day | 4.32E-01 | Joules |
| Energy of scans | 1.73E-02 | Joules |
| Total energy per day (Transmission + Sensing + leakage + wakeup radio) | 5.24E+00 | Joules |
| Number of days | 4.04E+02 | days |
| Number of years | 1.11E+00 | years |

Example implementations were performed for GHz sonic imaging using example embodiments of the disclosed methods, systems, and devices, like that shown in FIGS. 15A and 15B, for demonstrating that the disclosed technology can provide a comprehensive solution to characterize subsurface environment of plant growth. The GHz sonic technology can lead to better understanding between the under-soil activities correlation to plant health monitors that can be seen above ground. These correlations might lead to new models to be used in ongoing revolution in precision agriculture. In some applications, the disclosed technology could be integrated with existing technologies to further help facilitate the usefulness in the context of improving biofuel plant yields. In some implementations, data obtained by the example device and system can be used to predict the plant growth based on the variables measured.

Example implementations of an example GHz soil-condition ultrasonic imager device, also referred to as the "sensor" device or "ultrasonic sensor" device, are described for various technology development stages. Although a GHz ultrasonic imager was used in the example implementations, lower frequencies can also be utilized by the soil condition ultrasonic imager device 1500.

In an example first stage, example GHz ultrasonic sensor devices can be modified to collect data under soil with plants growing on top of the sensors. In example experimental implementations, this data can be conducted in a controlled environment, with the capability to control nematode populations, moisture, root sizes, moisture, temperature, and salinity and pH. The example sensors can be characterized and optimized to increase sensor SNR, decrease power consumption, and increase specificity. Example AlN transducers can be fabricated at CNF, and PC-Board level electronics can be developed and utilized for the example implementations. In parallel, AlN drivers can be implemented using custom CMOS circuits, e.g., including 180 nm CMOS.

In an example second stage, the example sensing system can be modified to miniaturize so that it can get to ~1 cc volume. In such embodiments, example COTS microcontrollers, CMOS drivers for the AlN tools, and forming the RF data transmission capabilities, with low power wakeup RF wakeup radios can be used. In experiments, the example miniaturized devices can be used to collect data from the sensors from farms. The data can be transmitted to the web and incorporated and correlated with aerial imagery of the plants being imaged.

Preliminary Imaging of Plant Roots. Initial experiments were performed to determine whether or not the acoustic impedance of plant roots and nematodes were detectable by the GHz sonar transducers. In the implementations, an example linear array ultrasonic transducer imager device with features like that shown in FIGS. 15A and 15B was used. The example ultrasonic transducer imager device used in these implementations included a 64-element linear transducer array comprised of 75 μm×75 μm square transducers. Images were formed by transmitting and receiving from each transducer in the 64-element transducer array.

Figure 17A:
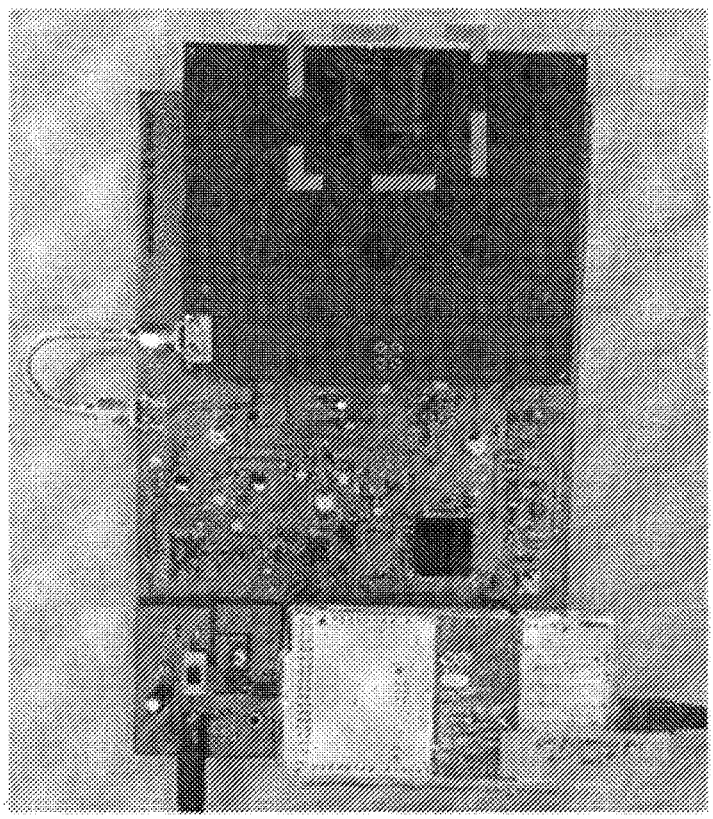
FIGS. 17A-17C show images of the example ultrasonic linear transducer array and imager circuit board used in example implementations for imaging of plant roots.

FIG. 17A shows an image of the example GHz ultrasonic linear array imager circuit board used in the preliminary imaging of plant roots. The silicon backside sensing surface of the example linear array ultrasonic transducer imager is shown in the dotted red box of FIG. 17A. The example circuit board setup used in these example implementations to acquire the images of plant roots was approximately 8.5 inches×5.5 inches in dimension. This example ultrasonic imager device was used for initial soil and nematode testing experiments.

Figure 17B:
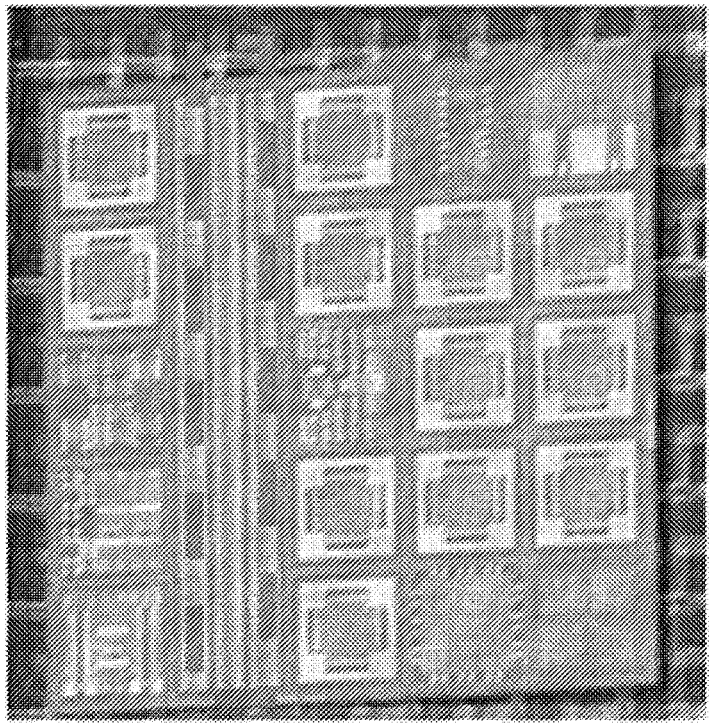

FIG. 17B shows a photo of the 1.8 cm×1.8 cm AlN die used for the imager device shown in FIG. 17A. The location of the linear array of the 64 ultrasonic transducer elements is shown in the red box of FIG. 17B.

Figure 17C:
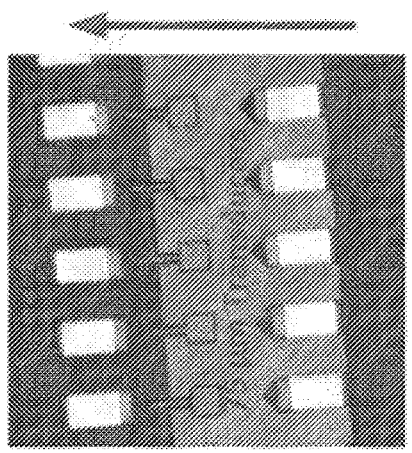

FIG. 17C shows a microscope image of a portion of the linear array, showing individual transducers. In this example, the sensor was configured as a linear array, on which the sample is swiped along the sensor in the direction indicated in FIG. 17C. In soil, the sensor cannot be readily scanned, and instead as the root grows over time, the different line scans will be indicative of the root growth rate and root cross-sections over time. For example, a two-dimensional imager, with transducers in 2D, can be used to scan in 2D to obtain larger images.

Figures 18A, 18B, 18C, 18D:
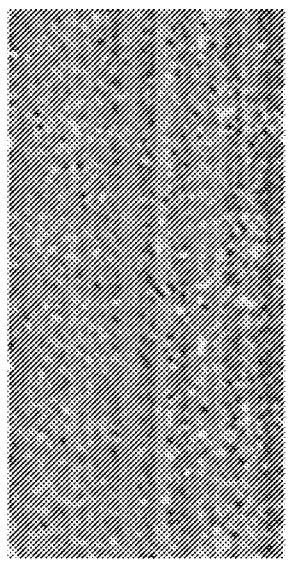
FIGS. 18A-18D show images of the plant root produced by implementation of an example ultrasonic imager device.

For the preliminary plant root imaging, a plant root shown in FIG. 18C was swiped across the example sensor. Two sections of the plant root were used—a section containing the taproot of the plant and another section where the taproot bifurcates into two smaller roots. A glass slide was used to press the root in contact with the silicon sensing surface. In the example data, the resolution of the sensing array is limited by the 200 µm pitch between the transducers.

FIGS. 18A-18D show images of the plant root produced by implementation of an example GHz ultrasonic imager device. FIG. 18A shows an image depicting an air-backed GHz ultrasound sensor image, which depicts that no objects are placed on the sensor. FIG. 18B shows an image produced by the example GHz ultrasonic imager device depicting the taproot of the plant. FIG. 18C shows a photograph of the root of the plant showing the two sections that were imaged by swiping along the sensor. FIG. 18D shows an image produced by the example GHz ultrasonic imager device depicting the portion of plant where the taproot is bifurcating into two roots. As shown by FIG. 18D, the left side of the image is where the root system still has a single taproot, and the right side of the image is where the root system has branched into two roots.

Example preliminary imaging of nematodes. Another set of example implementations of the example ultrasonic imager device was performed to test the performance of the sensor to nematodes. In these implementations, a commercially available sample of beneficial Steinernema feltiae nematodes was acquired. While these are not the same species as the plant parasitic nematodes discussed above, the acoustic properties of the different species are expected to be similar. Three globules of the nematodes, each containing large masses of hundreds to thousands of nematodes, were deposited on the example ultrasonic imager device at different times, as shown in FIG. 19A, with the globule labeled "1" deposited first, globule labeled "2" deposited next, and the globule labeled "3: deposited last. Notably, in this experiment, as the back side of the silicon was not marked, it was difficult to ascertain exactly where the linear array was located on the opposite side of the silicon and therefore globule 3 was not deposited on top of the sensing array.

FIGS. 19A-19D show images of the three samples of nematode globules on the sensing area of the example ultrasonic imager device and the GHz ultrasonic images acquired by the device. FIG. 19A shows an image showing a sensing surface of the silicon with the three globules of nematodes labeled. The sensing array lies along the two arrows. FIG. 19B shows an image depicting an air-backed GHz ultrasonic sensor image with no object on the sensor. FIG. 19C shows an image depicting the sensor image with the pixels changed by the presence of globule 1 shown in the red box. FIG. 19D shows an image depicting the sensor image with the pixels changed by the presence of globule 2 shown in the red box. As can be seen in FIGS. 19C and 19D, the image intensity changes as result of the presence of the nematode globules. As the sensing resolution of the sensor is limited along the length of the array by the transducer pitch of 200 µm, only a single array element is affected by part of globule 2.

Moisture testing. Example implementations were performed to demonstrate the use of the ultrasonic imager device as a moisture sensor. In the experimental setup shown in FIG. 20A, the sensor was used to measure the moisture content of a cleanroom wipe.

Figure 20A:
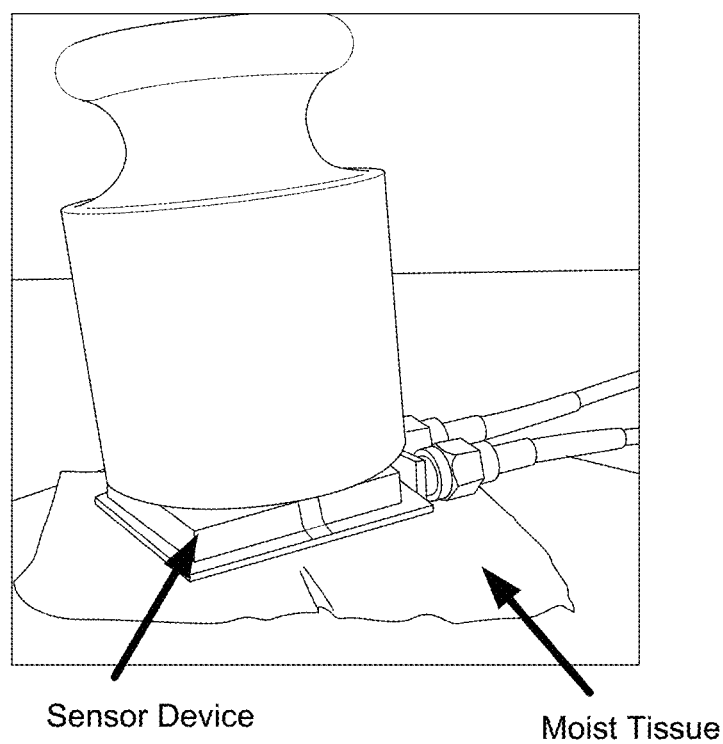
FIGS. 20A and 20B show an image and data plot, respectively, of an example ultrasonic imager device demonstrating the acoustic signals reflecting back from a tissue paper with moisture that changes over time due to evaporation.
Figure 20B:
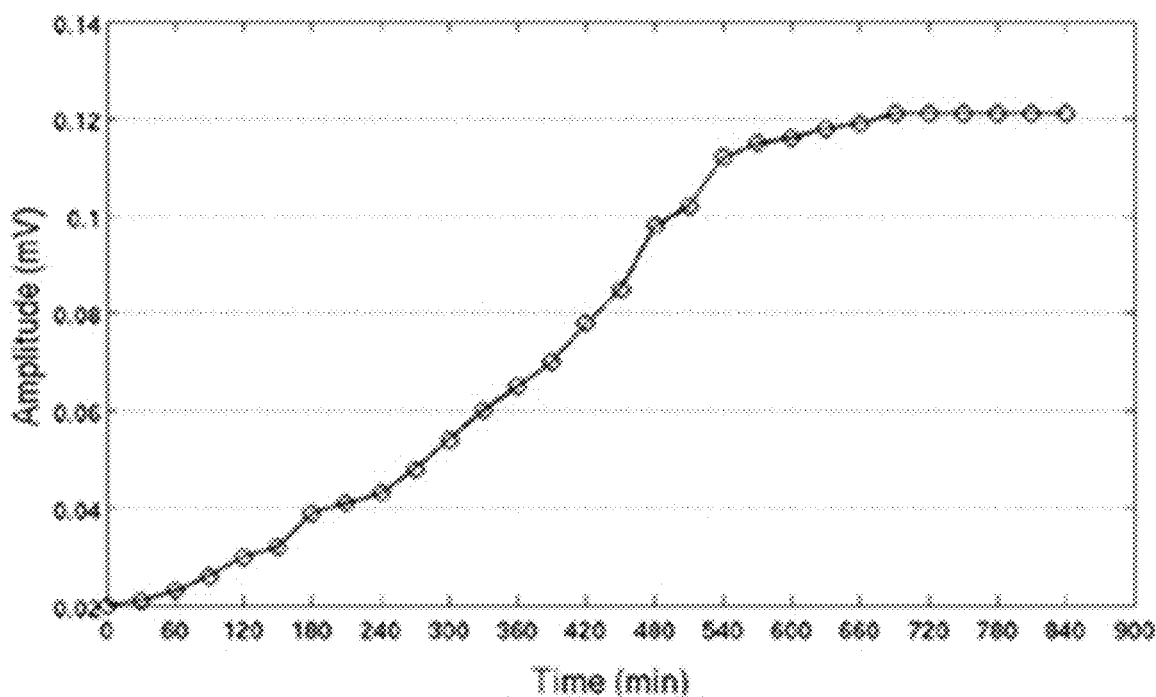

FIGS. 20A and 20B show an image and data plot, respectively, of an example GHz ultrasonic imager device demonstrating the acoustic signals reflecting hack from a tissue paper with moisture that changes over time due to evaporation. Notably, as shown in the data, the return signal increases with reduced moisture. Due to the higher acoustic impedance of water, compared to air, the receive signal is lower when the wipe is very wet, as more of the acoustic energy is transmitted into the wipe, as opposed to reflecting back into the silicon. As the wipe dries out, the received voltage signal increases because the acoustic impedance of the wipe is reduced as the water content evaporates off.

Temperature and thermal conductivity measurements. The speed of sound changes with temperature and can be used a basis to measure the temperature of the soil touching the ultrasonic soil condition sensor device. The time-of-flight (TOF) of the pulses can be measured to determine the temperature of an object in contact with the sensor. This ability to measure thermal conductivity can be used in conjunction with temperature to characterize the soil properties, providing yet another parameter to help classify plant health. For example, in soil, temperature disruptions can be made by heating the silicon chip itself with integrated heaters and then measuring the transients in the TOF versus time.

In some implementations, the disclosed techniques can produce acoustic impedance maps that identify where the roots and nematodes are. The impedance data in root and nematode areas can be used to identify the health of root and type of nematodes. In the soil areas, the reference TOF and soil TOF can be used to extract the TOF versus a pulsed thermal heater response to extract thermal conductivity. Differential measurements of the time-of-flight (TOF), which depends on the medium elasticity, density, loss mechanisms, and temperature, can be used to extract different parameters. Then the TOF and impedance data in soil areas can be used to assess moisture levels and ionic levels, as the TOF and impedance are functions of the ionic-concentration based loss mechanisms. The impedance and TOF measurements can be conducted at a series of carrier frequencies do assess the dispersion properties, giving additional physical parameters to map and identify physical variables. The example preliminary results on dispersions have yielded ability to sense different silicone rubber types. Given that the sensor can use RF frequencies for GHz ultrasonic measurements, direct RF measurements of the soil can be employed for soil electrical impedance providing additional data to differentiate. This measurement can be combined with the ultrasonic measurement to decouple soil moisture content and salinity, as it is known that soil permittivity is dependent on soil moisture and salinity levels. This multimodal measurements, combined with regression and AI approaches matched to measured data are envisioned to lead to a sensor system that provides useful answers to farmers for actions.

Figure 21A:
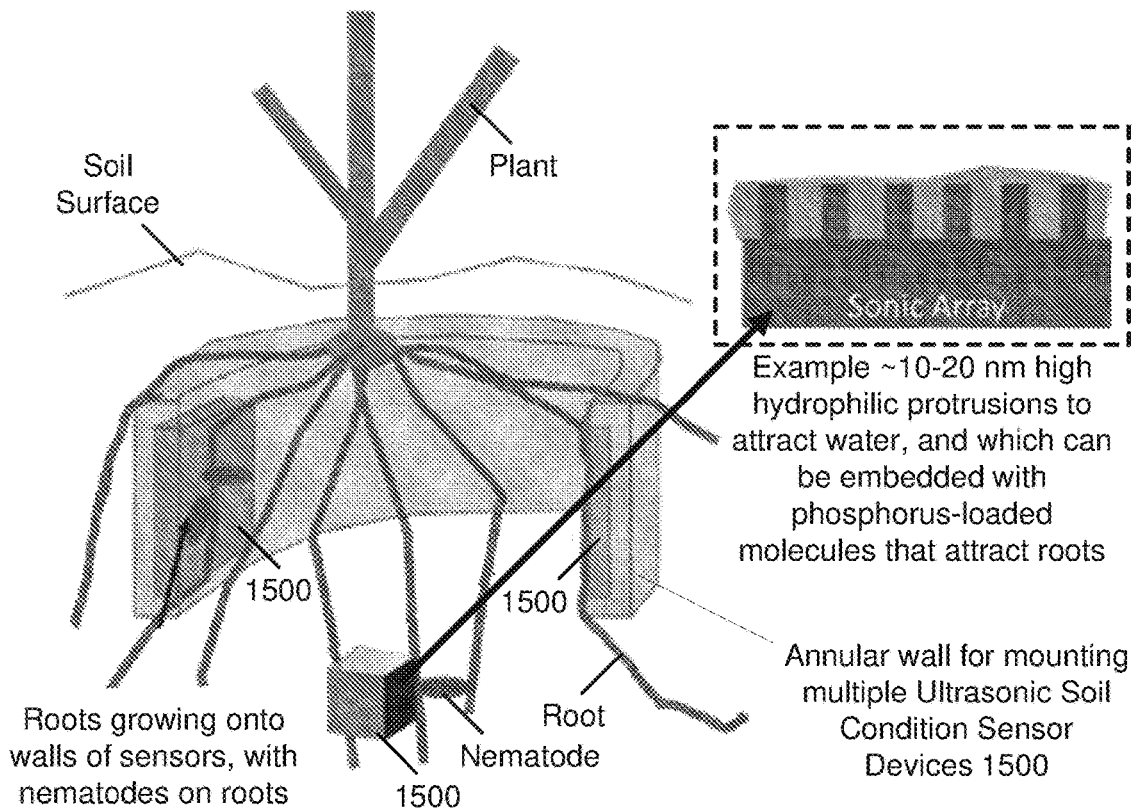
FIGS. 21A and 21B show diagrams of example ultrasonic sensor devices for imaging plant sub-soil parasites and monitoring root growth rates, temperature, thermal conductivity, ionic concentrations by ultrasonic pulse reflectometry.
Figure 21B:
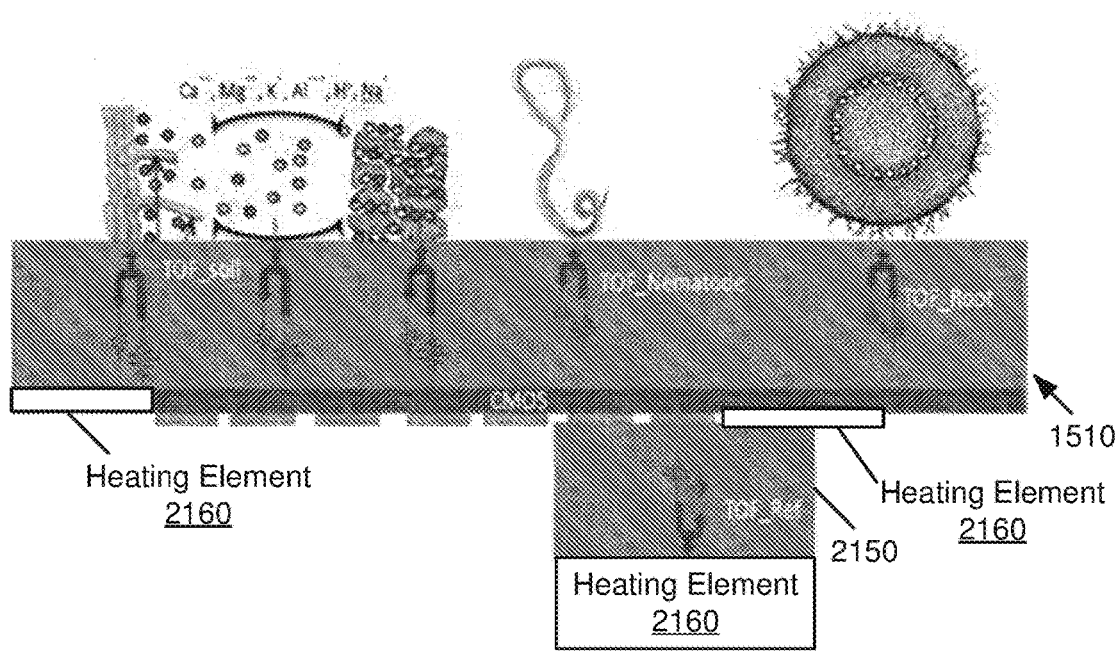

FIGS. 21A and 21B show diagrams of example ultrasonic sensor devices 1500 that can be placed below the seeds and the plant will grow over the seed with roots covering the sensor, in which GHz sonic imaging can image moving nematodes and root growth rates and GHz ultrasonic sensing can also be used to measure temperature, thermal conductivity, ionic concentrations by ultrasonic pulse reflectometry.

As shown in FIG. 21A, a circular annular cylinder lined with a few GHz sonic imager chips can run in the root growth pathway, bend their growth along the chip as occurs naturally. The ultrasonic chip surface can include hydrophilic surfaces to hold water in access of surrounding soil, attracting roots to grow. The surface can also include slow diffusing nutrients to attract roots.

As shown in FIG. 21B, the ultrasonic transceiver sensor device 1510 is operable to detect ion concentration changes in the soil at the sensing surface (e.g., contact layer 1519) of the sensor by employing the disclosed TOF sensing techniques using the GHz ultrasonic signals (e.g., 0.5 GHz or greater). As illustrated in the diagram, the ultrasonic soil condition sensor device 1500 can include a reference substrate 2150 (e.g., silicon) coupled to the ultrasonic transceiver sensor device 1510 on the side of the transducer elements 1513 opposite the CMOS layer 1512 and substrate 1511. For example, the reference block is not affected by the soil, and hence provides a TOF that is a reference compared to rest of transducers facing the soil. The transient heating of the substrate and the soil leads to heat diffusion away from the substrate and the soil and the heat flow effect on TOF can be used to characterize the thermal conductance of the soil at the surface.

In some embodiments, the device 1500 can include a heating element 2160 coupled to the reference substrate 2150 or the main (sensing) substrate 1511 to create a controlled heat (temperature) of the reference substrate 2150 and the soil. For example, the heater 2160 can be integrated within the CMOS circuitry controlling the transducers in the main substrate 1511. In this manner, the ultrasonic transceiver sensor device 1510 can implement the TOF technique through both the substrate 1511 (interfaced by the contact layer 1519 with the soil, roots, and/or organisms in soil) and the reference substrate 2150 for self-calibration based on a set of knowable thermal conductivity values from measurements of the reference substrate 2150. Other soil components, such as viruses and bacteria, may also be measured by the combination of measurement of TOF, impedance, and thermal conductance characterization.

Figure 21C:
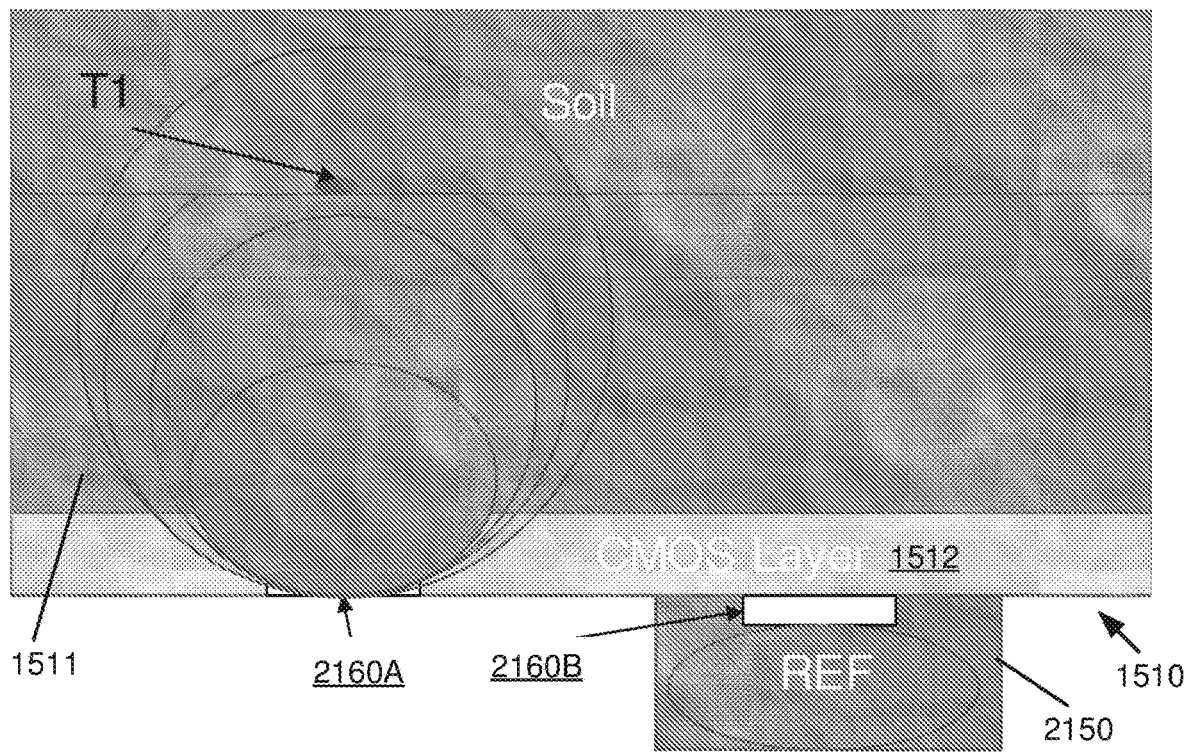
FIGS. 21C and 21D show a diagram and data plot, respectively, illustrating a heat flow effect on time-of-flight measurements by an example ultrasonic transceiver sensor device.
Figure 21D:
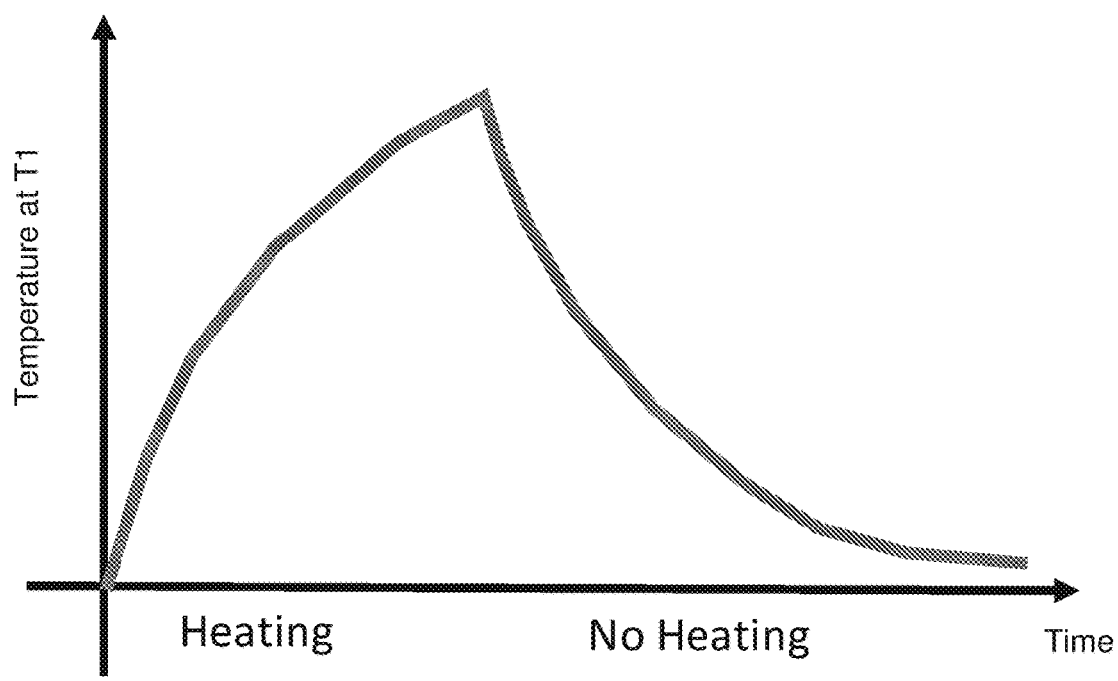

FIGS. 21C and 21D show a diagram and data plot illustrating the measurable heat flow effect on TOF that the ultrasonic transceiver sensor device 1510 of the device 1500 can use to characterize the thermal conductance and determine temperature of a target in the soil (e.g., nematode, roots, or soil itself) on the contact layer 1519 of the sensor device 1510. In the example of FIG. 21C, two heating elements 2160 are shown, but it is understood that one heating element 2160 can be used in implementations. In the example, the heating element 2160A is coupled to the main (sensing) substrate 1511 to create a controlled heat (temperature) of the substrate 1511 and the soil. Similarly, the heating element 2160B is coupled to the reference substrate 2150 to create a controlled heat (temperature) of the reference substrate 2150 that can be used in comparative analysis with TOF measurements of the soil. As shown by the data plot of FIG. 21D, the x-axis represents time and the y-axis represents temperature at the point (or object) T1 shown in the diagram of FIG. 21A, depicting heating and no heating over time.

Figure 22A:
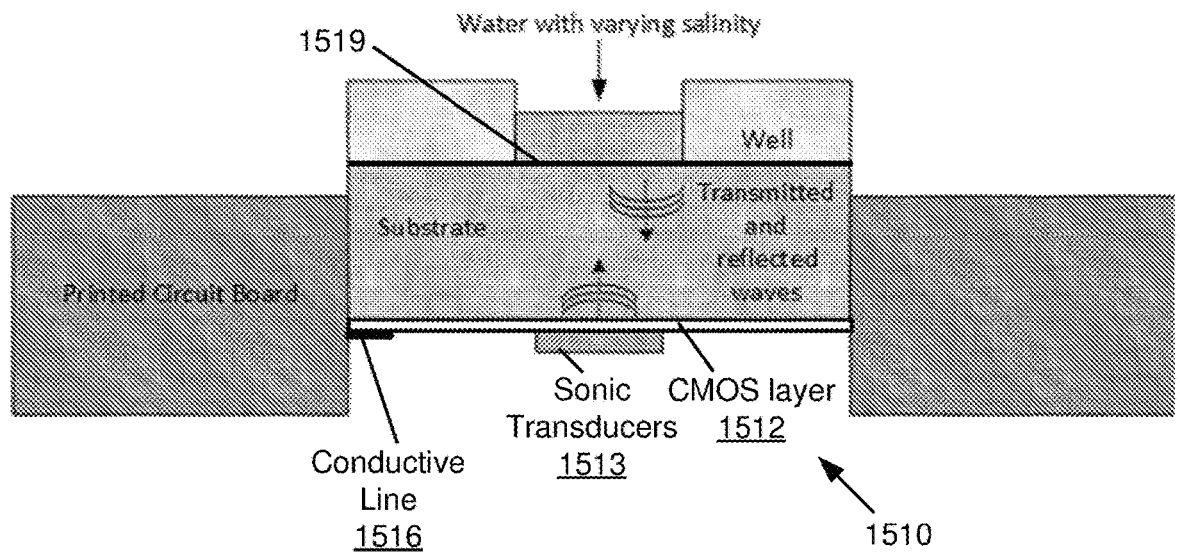
FIG. 22A shows a diagram of an example ultrasonic soil condition sensor device for examining properties of a fluid in contact with the sensing surface.
Figure 22B:
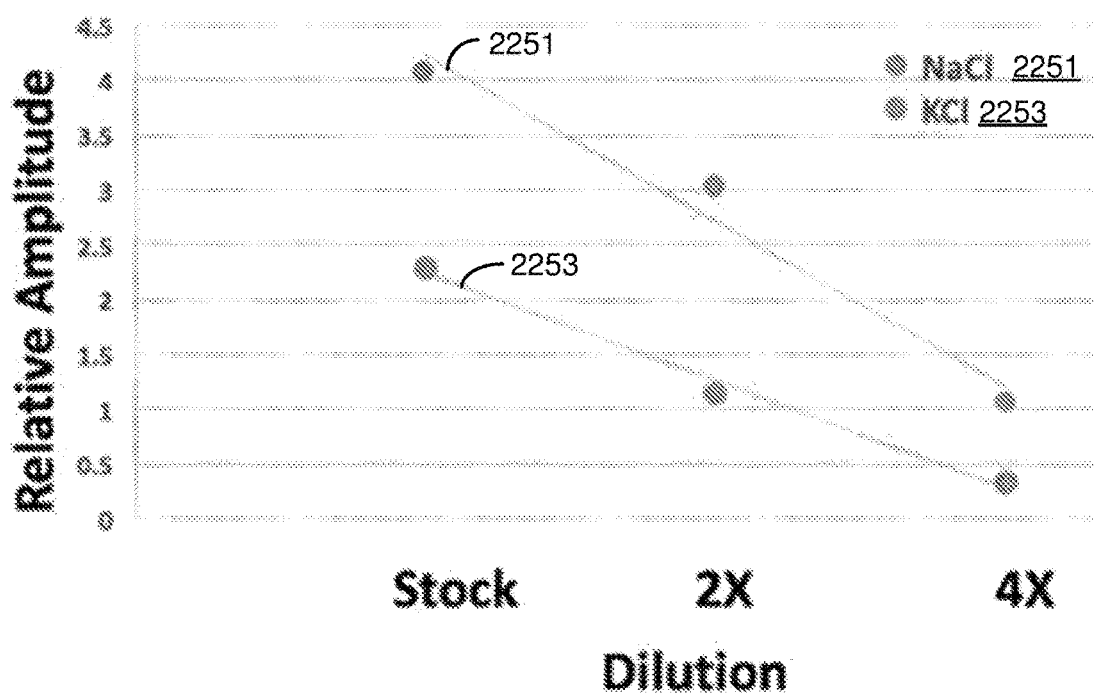
FIG. 22B shows a data plot depicting the results of salinity measurements using an example ultrasonic soil condition sensor device.

FIGS. 22A and 22B show a diagram of an example ultrasonic soil condition sensor device 1500 and data plot illustrating the transmit/receive pulse response versus ion concentration of KCl and NaCl. In this example shown in FIG. 22A, a fluid well (e.g., PDMS) is attached to the sensing surface of the device 1500, which contains a fluid with varying salinity within the well. As illustrated by the diagram, the return signal decreases with reduced ionic concentrations. The resolution of measurement can be estimated to be around 3-mMolar.

FIG. 22B shows a data plot depicting the results of salinity measurements using the example ultrasonic soil condition sensor device 1500 as shown in FIG. 22A. As shown in FIG. 22B, the ultrasonic impedance is a function of ionic concertation in liquids due to the ion motion due to sonic creates an electrostatic drag force on the liquid. The dependence on KCl and NaCl solutions reflectance is shown by the data 2253 and 2251, respectively, in FIG. 22B.

Example implementations of the disclosed devices, like that in FIGS. 15A and 15B, demonstrated the capability to make sufficient contact with nematodes for effective monitoring applications. For example, the ultrasonic absorption in soil is indeed high and hence close proximity to the sensor surface, within 100 µm is necessary to image. Instead of imaging the entire plumage, the example devices can acquire important health aspects such as water content, surface roughness, and nematodes that might be feeding on the roots in close proximity to the sensor. Example data sets from example sensors like that shown in FIGS. 4A-4D, 5A-5C, 6, and 15A and 15B, for example, demonstrate the ability to image and characterize the ultrasonic impedance of roots. Moreover, the integrated sensors can achieve 10-20 times higher SNR for higher resolution images.

One common method to image the roots now is shovelomics—washing the roots of a plant removed from soil, and then optically imaging the roots. "Shovelomics" gives the root plumage, but is destructive, costly, and does not provide the microscopic growth or nematode data. Yet, to date, no known technologies exist that are capable of obtaining microscopic long-duration root images, which would offer new insights into plant growth above and below ground. To increase sampled volume, the example ultrasonic imaging sensors can be deployed at different depths in the soil near a plant to help track of roots near the earth surface and deeper in soil. To ensure that the roots grow on the sensor surface, the disclosed techniques can include placement of a larger surface with sensors such that, as roots grow, the plant's roots will encounter the sensor surface and grow around the surface forming roots on the surface; and placement of micro-textured surfaces that can trap water due to surface tension, attracting water-seeking root tips. In some embodiments, the protrusions from the contact layer of the soil condition sensor devices can contain organic potassium rich coatings. The root tips during growth are attracted to potassium carrying volumes in soil.

Figure 23:
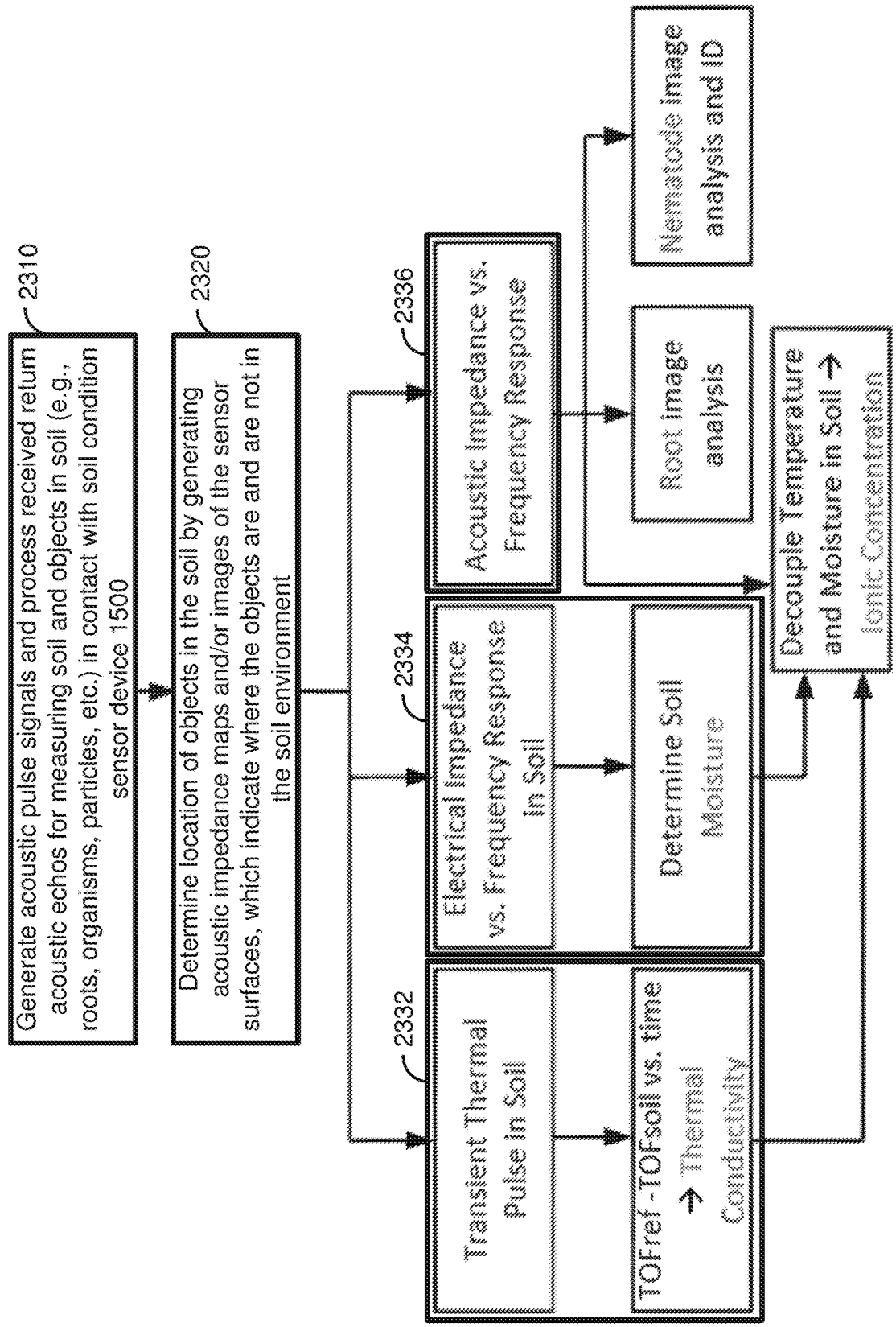
FIG. 23 shows a flow chart of an example method for ultrasonic imaging and sensing of multiple conditions in soil including target parasites like nematode in soil proximate roots of a plant.

FIG. 23 shows a flow chart of an example method for ultrasonic imaging and sensing of target parasites like nematode in soil proximate roots of a plant using example embodiments of the ultrasonic soil condition sensor device 1500. Since many ultrasonic transceiver sensor devices 1510s are configured in the device 1500 to interface the soil, e.g., with different areas of the sensor exposed to different soil components, a strategy is needed to determine the different sensor components. In one example, acoustic impedance maps are produced to identify where the roots and nematodes arc, in which their location on the produced acoustic impedance maps is determined based on considerable different measured impedances as compared to that of soil itself. The impedance and image data in root and nematode areas can be used to identify the health of root and type of nematodes. In these areas, the TOF measurements on transient heating can be used to further differentiate root types and nematode types. In the soil-only areas, the reference TOF and soil TOF will be used to extract the TOF versus a pulsed thermal heater response to extract thermal conductivity. Differential measurements of the time-of-flight (TOF), which depends on the medium elasticity, density, loss mechanisms, and temperature, will be used to extract different parameters. Then the TOF and impedance data in soil areas will be used to assess moisture levels and ionic levels, as the TOF and impedance are functions of the ionic-concentration based loss mechanisms. The impedance and TOF measurements will be conducted at a series of different carrier frequencies (around the main GHz frequencies used (e.g., 0.5 GHz or greater)) to assess the dispersion properties, giving additional physical parameters to map and identify physical variables.

As shown in FIG. 23, the example method for ultrasonic sensing of soil, soil environment, and objects in soil, using the ultrasonic soil condition sensor device 1500, includes a process 2310 to measure the soil and soil objects by generating acoustic pulse signals (e.g., at the piezoelectric transducers 1513) transmitted at the surface interface of the sensor device 1510 and the soil (e.g., at the outer surface of the contact layer 1519) and receiving returned acoustic signals reflected from the surface interface (e.g., received at the piezoelectric transducers 1513). The method includes a process 2320 to process to acoustic data to produce an acoustic impedance map and/or images of the interface surface and determine locations of the objects in the soil. For example, the acoustic impedance map and/or the images are processed to identify objects in the soil (e.g., nematodes, roots, or other) with respect to a location in the soil surrounding the ultrasonic soil condition sensor device 1500, which can distinguish which detected regions (surface interfaces) have one or more objects (such as roots, parasites, etc.) and which detected regions do not have an object present in that soil space.

For example, nematodes can be identified as they move on the surface while other components generally don't move with a consist slow velocity. Roots can be identified by acquiring the images and correlating the patterns with typical patterns associated with those measured with roots, e.g., in controlled implementations. Pattern matching approaches can be employed by the method, e.g., based on machine learning approaches, to identify and distinguish the type of objects on the sensor. For example, the method can include a process to transfer the data to an external computing device or network of computing devices in communication with each other (e.g., the cloud), which apply machine learning techniques to determine patterns in the sensor data, e.g., such as data processing in the cloud as data from several hundreds of sensors is transmitted to the cloud from example soil condition sensor devices 1500 deployed in the field and/or in controlled settings.

The method can include a process 2332 to determine thermal parameters (e.g., thermal conductivity) of the soil and/or contents in the soil. In such implementations, the ultrasonic soil condition sensor device 1500 can measure TOF of acoustic pulses with respect to the surface interface, in which transient heating can be used to further differentiate information of soil objects present in that region of the soil. The method can include a process 2334 to determine a moisture parameter of the soil and/or contents in the soil. In some implementations of the process 2334, direct RF measurements of the soil can be used to characterize electrical impedance providing additional data to differentiate parameters of the soil, like moisture. The method can include a process 2336 to measure the acoustic impedance versus the frequency response of the soil and/or objects in the soil at the surface interface.

In some implementations of the method, subsequent characterization processes for regions with an object present in the soil that are different from the subsequent characterization processes for regions of object-free soil.

Example results from implementations on dispersions have yielded the ability to sense different silicone rubber types. Given that the sensor is already using RF frequencies for GHz ultrasonic measurements, direct RF measurements of the soil can be used for soil electrical impedance providing additional data to differentiate. This measurement can be combined with the ultrasonic measurement to decouple soil moisture content and salinity, as it is known that soil permittivity is dependent on soil moisture and salinity levels. This multimodal measurement, combined with regression and AI approaches matched to measured data, can enable a sensor system that provides useful answers to farmers for actions.

The example approach can ensure root growth onto sensor surface during the growth phase. In implementations of the method shown in FIG. 23, the method can be used for extracting parameters from TOF and impedance maps. In the nematode and soil area, impedance versus frequency provides nematode and root properties. In soil areas, a pulsed thermal transient is used to extract thermal conductivity by measuring the reference TOF versus soil TOF. Impedance versus frequency on solid provides moisture information. Combination of thermal conductivity and reflectance data can model ionic concentration and porosity.

Figure 24:
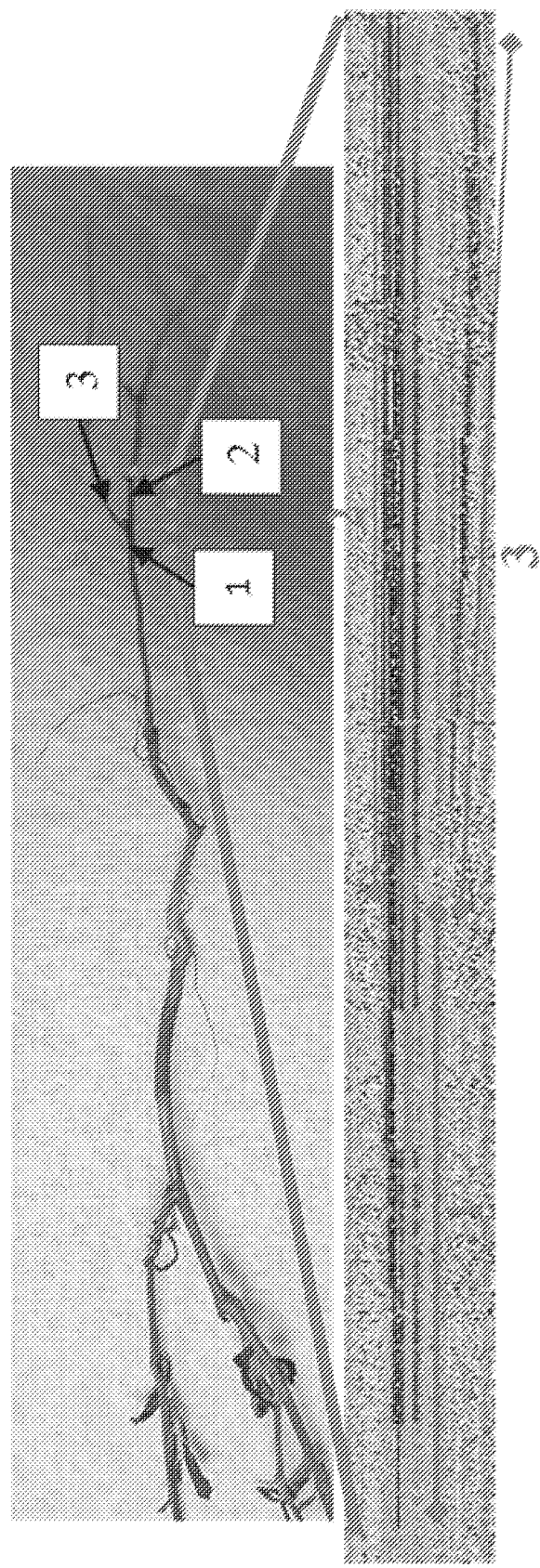
FIG. 24 shows an image depicting an example of imaged roots, showing the ability to detect bifurcations in roots, ultrasonic impedance map as darkness of the grayscale image.

FIG. 24 shows an image depicting an example of imaged roots, showing the ability to detect bifurcations in roots, ultrasonic impedance map as darkness of the grayscale image.

In some example implementations, for example, parameters of GHz US imaging to measure the roots and nematodes can be optimized. Wired sensors can be used and software can be developed to extract the root and nematode images and study over time. The software and hardware co-optimization can include adjusting the transducer sizes, ultrasonic frequencies. For example, it is envisioned that the SNR can be increased to >30 dB of the ultrasonic transducers and image processing filters can be optimized to create surface and 3D renditions of objects on the sonic imagers. Optical images of the plant above the soil can be used to develop correlations with ultrasonic image data.

For example, the physical aspects of the soil can be measured independently of each other—the time of flight, and the return amplitude, as a function of the ultrasonic carrier frequency. Pump-probe method of applying RF fields to move ions, and temperature transients with integrated heaters can be used to "pump" to extract different TOF and return amplitudes. The parameters can be measured with sufficient resolution to be useable for plant health assessment.

In some example implementations, a portable system can be placed below plant seedlings for measurement as the plant grows. In some implementations, the portable system can have target volume of 4 cc; yet, the portable system can be customized to smaller sizes, e.g., potentially reaching less than 1 cc. In some implementations, the data collected can be retrieved using a Bluetooth wireless interface, operating under the control of a wakeup RF receiver. For example, CMOS-integrated AlN transducers can be used to miniaturize the system volume. The RF reader can be a COTS microcontroller software defined radio to communicate with the sensor unit.

The example system is able to address various challenges. For example, nematodes can be imaged with sufficient resolution to discriminate between different species of nematodes. The nematode diameter ranges from 5-100 um and there are great many beneficial nematodes than the number of adversarial nematodes. The movement of the nematodes, types of motion, and sizes may lead to specific signatures to different kinds of nematodes. High SNR and spatial resolution can be used to measure the parameters constructively.

For example, physical variables can be measured with sufficient resolution to classify effects on plant health. In conventional systems, the ionic concentration sensing is not able display sufficient resolution and require high power to achieve performance. The disclosed processes to include electrical electrodes, such as platinum, can be used to measure electrochemical properties.

EXAMPLES

In an example embodiment in accordance with the present technology (example 1), an ultrasonic transceiver sensor device includes a substrate including a semiconductor material; a CMOS layer attached to a first side of the substrate; an array of piezoelectric transducers coupled to the CMOS layer and operable to generate ultrasonic pulses having a frequency of at least 0.5 GHz; and a contact layer attached to a second side of the substrate opposite the first side to provide a surface for contact with an object, wherein an ultrasonic pulse generated by a piezoelectric transducer of the array is directed to propagate through the substrate and the contact layer, such that when the object is in contact with the surface of the contact layer, a reflected ultrasonic pulse is produced and propagates through the contact layer and the substrate to be received at the array of piezoelectric transducers, wherein CMOS elements of the CMOS layer in communication with the array of piezoelectric transducers are operable to receive and process outputs from the piezoelectric transducers produced in response to the received reflected ultrasonic pulses.

Example 2 includes the ultrasonic transceiver sensor device of any of the preceding or subsequent examples 1-26, wherein reflected ultrasonic pulses received at the piezoelectric transducers include varying times and amplitudes associated with valleys and peaks of the object in contact with the contact layer that correspond to echo signals of different delays and magnitudes to represent physical features of the object in contact with the ultrasonic transceiver sensor device.

Example 3 includes the ultrasonic transceiver sensor device of any of the preceding or subsequent examples 1-26, further comprising a plurality of ridges formed on the surface of the contact layer, wherein the ridges are configured to change in shape based on an applied force by the object, such that reflected ultrasonic pulses received at the piezoelectric transducers are returned from the ridges that correspond to echo signals of different delays and magnitudes corresponding to the applied force.

Example 4 includes the ultrasonic transceiver sensor device of any of the preceding or subsequent examples 1-26, wherein plurality of ridges facilitate increased resolution of a differential between the generated ultrasonic pulse transmitted toward the object in contact with the plurality of ridges and the reflected ultrasonic pulses received at the piezoelectric transducers are returned from the ridges, such that a type of force, including a normal force, a shear force, or a combination of both, is determinable.

Example 5 includes the ultrasonic transceiver sensor device of any of the preceding or subsequent examples 1-26, wherein the plurality of ridges is structured as a homogenous layer, wherein the ridges have a substantially uniform set of material properties and topology.

Example 6 includes the ultrasonic transceiver sensor device of any of the preceding or subsequent examples 1-26, wherein the plurality of ridges is structured as a heterogeneous layer, wherein the ridges have a varying set of material properties and topology.

Example 7 includes the ultrasonic transceiver sensor device of any of the preceding or subsequent examples 1-26, wherein the heterogenous layer includes groups of homogenous ridges that vary periodically or intermittently.

Example 8 includes the ultrasonic transceiver sensor device of any of the preceding or subsequent examples 1-26, wherein the CMOS elements of the CMOS layer in communication with the array of piezoelectric transducers are operable to receive and process outputs from the piezoelectric transducers produced in response to the generated ultrasonic pulses transmitted toward the contact layer and the received reflected ultrasonic pulses, such that a thermal property of the object in contact with the surface is determined based on the relative time-of-flight (TOF) of the ultrasonic pulses.

Example 9 includes the ultrasonic transceiver sensor device of any of the preceding or subsequent examples 1-26, wherein thermal property is determined based on a time-of-flight (TOF) of the ultrasonic pulses transmitted toward the contact layer and the received reflected ultrasonic pulses that corresponds to a temperature profile across (i) the contact layer and the substrate and (ii) the object in contact with the surface.

Example 10 includes the ultrasonic transceiver sensor device of any of the preceding or subsequent examples 1-26, wherein the thermal property of the object is a temperature of a region of the object in contact with the surface.

Example 11 includes the ultrasonic transceiver sensor device of any of the preceding or subsequent examples 1-26, wherein the device is operable to determine a transient thermal time constant at the interface of the surface and the object in contact with the surface.

Example 12 includes the ultrasonic transceiver sensor device of any of the preceding or subsequent examples 1-26, further comprising a heating element coupled to the substrate to generate heat to control a temperature across the substrate.

Example 13 includes the ultrasonic transceiver sensor device of any of the preceding or subsequent examples 1-26, further comprising: a reference substrate including a semiconductor material attached to the array of piezoelectric transducers and/or the CMOS layer on an opposite side to the substrate, wherein heating element is operable to generate heat to control a temperature across the reference substrate.

Example 14 includes the ultrasonic transceiver sensor device of example 13, wherein the heating element is integrated within the CMOS layer.

Example 15 includes the ultrasonic transceiver sensor device of any of the preceding or subsequent examples 1-26, further comprising a reference substrate including a semiconductor material attached to the array of piezoelectric transducers and/or the CMOS layer on an opposite side to the substrate; and a heating element coupled to the reference substrate to generate heat to control a temperature across the reference substrate.

Example 16 includes the ultrasonic transceiver sensor device of example 15, wherein the heating element is integrated within the CMOS layer.

Example 17 includes the ultrasonic transceiver sensor device of any of the preceding or subsequent examples 1-26, wherein the contact layer includes a polymer material.

Example 18 includes the ultrasonic transceiver sensor device of any of the preceding or subsequent examples 1-26, wherein the polymer material includes polyvinylidene fluoride (PVDF), polydimethylsiloxane (PDMS), polyethylene, or parylene.

Example 19 includes the ultrasonic transceiver sensor device of any of the preceding or subsequent examples 1-26, wherein the polymer material includes a thickness of less than 10 μm, or less than 20 μm, or less than 100 μm, or less than 1 mm, or less than 10 mm.

Example 20 includes the ultrasonic transceiver sensor device of any of the preceding or subsequent examples 1-26, wherein the contact layer includes a combination of soft and hard materials.

Example 21 includes the ultrasonic transceiver sensor device of any of the preceding or subsequent examples 1-26, wherein the array of piezoelectric transducers includes an array of aluminum nitride (AlN) transducer elements.

Example 22 includes the ultrasonic transceiver sensor device of any of the preceding or subsequent examples 1-26, wherein the array of MN transducer elements include 10×10 elements each having a size of 20 μm×20 μm.

Example 23 includes the ultrasonic transceiver sensor device of any of the preceding or subsequent examples 1-26, wherein the substrate includes silicon.

Example 24 includes the ultrasonic transceiver sensor device of any of the preceding or subsequent examples 1-26, wherein the device includes a size dimension of 100 μm to 1000 μm.

Example 25 includes the ultrasonic transceiver sensor device of any of the preceding or subsequent examples 1-26, wherein the device is configured on a microchip or wafer scale array.

Example 26 includes the ultrasonic transceiver sensor device of any of the preceding examples of 1-25, wherein the ultrasonic transceiver sensor device is configured on a flexible base proximate to a second ultrasonic transceiver sensor device, separated by a soft polymer material between the ultrasonic transceiver sensor devices, and each ultrasonic transceiver sensor device in communication with a data processing unit via a bus.

In an example embodiment in accordance with the present technology (example 27), a sensing membrane for performing different sensing functions based on ultrasonic sensing includes a flexible base; an ultrasonic transceiver touch sensor coupled to the flexible base at a first location and configured to detect an object in contact with an exterior surface of the ultrasonic transceiver touch sensor based on transmitted ultrasonic signals at the surface and received reflected ultrasonic signals indicative of the object when the object is in contact to sense touch; an ultrasonic transceiver force sensor coupled to the flexible base at a second location and configured to detect a force applied by the object in contact with a ridge structure on an outer surface of the ultrasonic transceiver force sensor based on ultrasonic signals transmitted at the surface and returned ultrasonic signals received indicative of the applied force by the object to sense force; an ultrasonic transceiver temperature sensor coupled to the flexible base at a third location and configured to detect a thermal property of the object in contact with an external surface of the ultrasonic transceiver temperature sensor based on the relative time of flight of transmitted ultrasonic signals and received reflected ultrasonic signals from the surface when the object is in contact to sense temperature; and a bus in electrical communication with each of the ultrasonic transceiver touch sensor, ultrasonic transceiver force sensor, and ultrasonic transceiver temperature sensor, wherein the sensing membrane is in communication with a data processing unit to regulate transmission of the ultrasonic signals of each respective ultrasonic transceiver sensor and process data associated with the transmitted and received ultrasonic signals by each respective ultrasonic transceiver sensor.

Example 28 includes the sensing membrane of any of example 27 or subsequent examples 29-33, comprising an array of the ultrasonic transceiver sensors arranged on the flexible substrate and including a plurality of the ultrasonic transceiver touch sensors, a plurality of the ultrasonic transceiver force sensors, and a plurality of the ultrasonic transceiver temperatures sensors, wherein the ultrasonic transceiver sensors of the array are arranged to spatially distribute the ultrasonic transceiver touch sensors, the ultrasonic transceiver force sensors, and the ultrasonic transceiver temperature sensors to emulate sensing functions of a human hand.

Example 29 includes the sensing membrane of any of the preceding or subsequent examples 27-33, further comprising a signal processing circuit including a power source, ground and a differential amplifier coupled to the bus and in communication with the ultrasonic transceiver touch sensor, the ultrasonic transceiver force sensor, and the ultrasonic transceiver temperature sensor.

Example 30 includes the sensing membrane of any of the preceding or subsequent examples 27-33, wherein the ultrasonic transceiver touch sensor includes: a substrate including a semiconductor material; a CMOS layer attached to a first side of the substrate; an array of piezoelectric transducers coupled to the CMOS layer and operable to generate ultrasonic pulses having a frequency of at least 0.5 GHz; and a contact layer attached to a second side of the substrate opposite the first side to provide the exterior surface for contact with the object, wherein an ultrasonic pulse generated by a piezoelectric transducer of the array is directed to propagate through the substrate and the contact layer, such that when the object is in contact with the surface of the contact layer, a reflected ultrasonic pulse is produced and propagates through the contact layer and the substrate to be received at the array of piezoelectric transducers, wherein CMOS elements of the CMOS layer in communication with the array of piezoelectric transducers are operable to receive and process outputs from the piezoelectric transducers produced in response to the received reflected ultrasonic pulses.

Example 31 includes the sensing membrane of any of the preceding or subsequent examples 27-33, wherein the ultrasonic transceiver force sensor includes: a substrate including a semiconductor material; a CMOS layer attached to a first side of the substrate; an array of piezoelectric transducers coupled to the CMOS layer and operable to generate ultrasonic pulses having a frequency of at least 0.5 GHz; and a contact layer attached to a second side of the substrate opposite the first side to provide a surface for contact with an object, the contact layer including a plurality of the ridge structures formed on the surface of the contact layer, wherein the ridge structures are configured to change in shape based on an applied force by the object, wherein an ultrasonic pulse generated by a piezoelectric transducer of the array is directed to propagate through the substrate and the contact layer, such that when the object is in contact with the surface of the contact layer, the shape of the ridges change and affect a reflected ultrasonic pulse that propagates back through the substrate and is received at the piezoelectric transducers corresponding to echo signals of different delays and magnitudes corresponding to the applied force, wherein CMOS elements of the CMOS layer in communication with the array of piezoelectric transducers are operable to receive and process outputs from the piezoelectric transducers produced in response to the received reflected ultrasonic pulses.

Example 32 includes the sensing membrane of any of the preceding or subsequent examples 27-33, wherein the ultrasonic transceiver temperature sensor includes: a substrate including a semiconductor material; a CMOS layer attached to a first side of the substrate; and an array of piezoelectric transducers coupled to the CMOS layer and operable to generate ultrasonic pulses having a frequency of at least 0.5 GHz, wherein the array of piezoelectric transducers includes a group of transmit transducer elements to generate transmit ultrasonic pulses directed to propagate through the substrate and a group of receive transducer elements to receive reflected gigahertz ultrasonic pulses that propagate back through the substrate upon reflection by the object in contact with the external surface on the opposite side of the substrate to the first side, wherein CMOS elements of the CMOS layer in communication with the array of piezoelectric transducers are operable to receive and process outputs from the piezoelectric transducers produced in response to the generated transmit ultrasonic pulses and the received reflected ultrasonic pulses, such that a thermal property of the object in contact with the surface is determined based on the relative time of flight of the ultrasonic pulses.

Example 33 includes the sensing membrane of any of the preceding examples of 27-32, further comprising an array of soft polymer spacing structures coupled to the flexible base and positioned between adjacent ultrasonic transceiver sensors to provide spacing between the adjacent ultrasonic transceiver sensors.

In an example embodiment in accordance with the present technology (example 34), an ultrasonic sensor device for characterizing constituents in soil includes a housing including an opening; an ultrasonic transceiver sensor device contained in the housing, in which the ultrasonic transceiver sensor device includes a substrate including a semiconductor material, a CMOS layer attached to a first side of the substrate, an array of piezoelectric transducers coupled to the CMOS layer and operable to generate ultrasonic pulses having a frequency in a range of 0.5 GHz or less, and a contact layer attached to a second side of the substrate opposite the first side, wherein the ultrasonic transceiver sensor device is contained in the housing to position the contact layer at the opening to provide an exposed surface of the contact layer for contacting with soil or an object in the soil, wherein the ultrasonic transceiver sensor device is operable to generate an ultrasonic pulse by a piezoelectric transducer of the array that is directed to propagate through the substrate and the contact layer to the surface in contact with the soil or the object in the soil, such that a reflected ultrasonic pulse is produced at the surface that propagates through the contact layer and the substrate to be received at the array of piezoelectric transducers, wherein CMOS elements of the CMOS layer in communication with the array of piezoelectric transducers are operable to receive and process outputs from the piezoelectric transducers produced in response to the received reflected ultrasonic pulses; and a data processing and communications unit including a signal processing circuit, a power unit, and a wireless transmitter and/or receiver unit.

Example 35 includes the ultrasonic sensor device of any of example 34 or subsequent examples 36-61, wherein the contract layer is configured to provide a hydrophilic surface that contacts the soil or with the object in soil.

Example 36 includes the ultrasonic sensor device of any of the preceding or subsequent examples 34-61, wherein the contact layer includes an array of nanostructures protruding at a height of 10 nm to 20 nm to provide the hydrophilic surface.

Example 37 includes the ultrasonic sensor device of any of the preceding or subsequent examples 34-61, wherein the contact layer includes a plurality of ridges formed on the surface of the contact layer, wherein the ridges are configured to change in shape based on an applied force by the object in the soil, such that reflected ultrasonic pulses received at the piezoelectric transducers are returned from the ridges that correspond to echo signals of different delays and magnitudes corresponding to the applied force.

Example 38 includes the ultrasonic sensor device of any of the preceding or subsequent examples 34-61, wherein plurality of ridges facilitate increased resolution of a differential between the generated ultrasonic pulse transmitted toward the object in the soil in contact with the plurality of ridges and the reflected ultrasonic pulses received at the piezoelectric transducers are returned from the ridges, such that a type of force, including a normal force, a shear force, or a combination of both, is determinable.

Example 39 includes the ultrasonic sensor device of any of the preceding or subsequent examples 34-61, wherein the plurality of ridges is structured as a homogenous layer, wherein the ridges have a substantially uniform set of material properties and topology.

Example 40 includes the ultrasonic sensor device of any of the preceding or subsequent examples 34-61, wherein the plurality of ridges is structured as a heterogeneous layer, wherein the ridges have a varying set of material properties and topology.

Example 41 includes the ultrasonic sensor device of any of the preceding or subsequent examples 34-61, wherein the heterogenous layer includes groups of homogenous ridges that vary periodically or intermittently.

Example 42 includes the ultrasonic sensor device of any of the preceding or subsequent examples 34-61, wherein the CMOS elements of the CMOS layer in communication with the array of piezoelectric transducers are operable to receive and process outputs from the piezoelectric transducers produced in response to the generated ultrasonic pulses transmitted toward the contact layer and the received reflected ultrasonic pulses, such that a thermal property of the soil and/or the object in the soil in contact with the surface is determined based on the relative time-of-flight (TOF) of the ultrasonic pulses.

Example 43 includes the ultrasonic sensor device of any of the preceding or subsequent examples 34-61, wherein thermal property is determined based on a time-of-flight (TOF) of the ultrasonic pulses transmitted toward the contact layer and the received reflected ultrasonic pulses that corresponds to a temperature profile across (i) the contact layer and the substrate and (ii) the soil and/or the object in the soil in contact with the surface.

Example 44 includes the ultrasonic sensor device of any of the preceding or subsequent examples 34-61, wherein the thermal property of the soil and/or the object in the soil is a temperature of a region of the soil and/or the object in the soil in contact with the surface.

Example 45 includes the ultrasonic sensor device of any of the preceding or subsequent examples 34-61, wherein the device is operable to determine a transient thermal time constant at the interface of the surface and the soil and/or the object in the soil in contact with the surface.

Example 46 includes the ultrasonic sensor device of any of the preceding or subsequent examples 34-61, further comprising a heating element coupled to the substrate to generate heat to control a temperature across the substrate.

Example 47 includes the ultrasonic sensor device of any of the preceding or subsequent examples 34-61, further comprising a reference substrate including a semiconductor material attached to the array of piezoelectric transducers and/or the CMOS layer on an opposite side to the substrate, wherein heating element is operable to generate heat to control a temperature across the reference substrate.

Example 48 includes the ultrasonic sensor device of any of the preceding or subsequent examples 34-61, wherein the heating element is integrated within the CMOS layer.

Example 49 includes the ultrasonic sensor device of any of the preceding or subsequent examples 34-61, further comprising a reference substrate including a semiconductor material attached to the array of piezoelectric transducers and/or the CMOS layer on an opposite side to the substrate; and a heating element coupled to the reference substrate to generate heat to control a temperature across the reference substrate.

Example 50 includes the ultrasonic sensor device of any of the preceding or subsequent examples 34-61, wherein the heating element is integrated within the CMOS layer.

Example 51 includes the ultrasonic sensor device of any of the preceding or subsequent examples 34-61, wherein the wireless transmitter and/or receiver unit includes an RF transceiver and antenna contained in the housing and operable to transmit and/or receive data with an external device outside of the soil.

Example 52 includes the ultrasonic sensor device of any of the preceding or subsequent examples 34-61, wherein the housing includes a rigid elongated body with a sharp point on a first end to be inserted into the soil, wherein the one or more ultrasonic transceiver sensor devices are configured along corresponding openings arranged on the rigid elongated body toward the first end such that the one or more ultrasonic transceiver sensor devices are within soil when the ultrasonic sensor device is inserted into the soil.

Example 53 includes the ultrasonic sensor device of any of the preceding or subsequent examples 34-61, wherein the wireless transmitter and/or receiver unit includes an antenna disposed at a second end of the rigid elongated body such that it is positioned above the soil and operable to transmit and/or receive data with an external device outside of the soil.

Example 54 includes the ultrasonic sensor device of any of the preceding or subsequent examples 34-61, wherein the contact layer includes a polymer material.

Example 55 includes the ultrasonic sensor device of any of the preceding or subsequent examples 34-61, wherein the contact layer includes a combination of soft and hard materials.

Example 56 includes the ultrasonic sensor device of any of the preceding or subsequent examples 34-61, wherein the array of piezoelectric transducers includes an array of aluminum nitride (AlN) transducer elements.

Example 57 includes the ultrasonic sensor device of any of the preceding or subsequent examples 34-61, wherein the substrate includes silicon.

Example 58 includes the ultrasonic sensor device of any of the preceding or subsequent examples 34-61, wherein the ultrasonic sensor device includes a cubic shape.

Example 59 includes the ultrasonic sensor device of any of the preceding or subsequent examples 34-61, wherein the ultrasonic sensor device includes a size dimension of 2×2×2 cm$^3$.

Example 60 includes the ultrasonic sensor device of any of the preceding or subsequent examples 34-61, wherein the ultrasonic sensor device is operable to provide data for determining water content, chemical properties of the soil, root growth, or presence of a pest organism in the soil proximate the surface of the substrate.

Example 61 includes the ultrasonic sensor device of any of the preceding examples 34-60, wherein the pest organism includes a nematode.

In an example embodiment in accordance with the present technology (example 62), an ultrasonic transceiver force sensor device includes a substrate including a semiconductor material; a CMOS layer attached to a first side of the substrate; an array of piezoelectric transducers coupled to the CMOS layer and operable to generate ultrasonic pulses having a frequency of at least 0.5 GHz; and a contact layer attached to a second side of the substrate opposite the first side to provide a surface for contact with an object, the contact layer including a plurality of ridges formed on the surface of the contact layer, wherein the ridges are configured to change in shape based on an applied force by the object, wherein an ultrasonic pulse generated by a piezoelectric transducer of the array is directed to propagate through the substrate and the contact layer, such that when the object is in contact with the surface of the contact layer, the shape of the ridges change and affect a reflected ultrasonic pulse that propagates back through the substrate and is received at the piezoelectric transducers corresponding to echo signals of different delays and magnitudes corresponding to the applied force, wherein CMOS elements of the CMOS layer in communication with the array of piezoelectric transducers are operable to receive and process outputs from the piezoelectric transducers produced in response to the received reflected ultrasonic pulses.

In an example embodiment in accordance with the present technology (example 63), an ultrasonic transceiver temperature sensor device includes a substrate including a semiconductor material; a CMOS layer attached to a first side of the substrate; and an array of piezoelectric transducers coupled to the CMOS layer and operable to generate ultrasonic pulses having a frequency of at least 0.5 GHz, wherein the array of piezoelectric transducers includes a group of transmit transducer elements to generate transmit ultrasonic pulses directed to propagate through the substrate and a group of receive transducer elements to receive reflected gigahertz ultrasonic pulses that propagate back through the substrate upon reflection by an object in contact with a surface on the opposite side of the substrate to the first side, wherein CMOS elements of the CMOS layer in communication with the array of piezoelectric transducers are operable to receive and process outputs from the piezoelectric transducers produced in response to the generated transmit ultrasonic pulses and the received reflected ultrasonic pulses, such that a thermal property of the object in contact with the surface is determined based on the relative time of flight of the ultrasonic pulses.

Example 64 includes the ultrasonic transceiver temperature sensor device of example 62 or example 63, including features recited in any of examples 1-61.

Implementations of the subject matter and the functional operations described in this patent document and attached appendices can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document and attached appendices contain many specifics, these should not be construed as limitations on the scope of any invention or of what may be claimed, but rather as descriptions of features that may be specific to particular embodiments of particular inventions. Certain features that are described in this patent document and attached appendices in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendices should not be understood as requiring such separation in all embodiments.

Only a few implementations and examples are described and other implementations, enhancements and variations can be made based on what is described and illustrated in this patent document and attached appendices.

What is claimed is:

1. An ultrasonic transceiver sensor device, comprising:
a substrate including a semiconductor material;
a CMOS layer attached to a first side of the substrate;
an array of piezoelectric transducers coupled to the CMOS layer and operable to generate ultrasonic pulses having a frequency of at least 0.5 GHz; and
a contact layer, on a second side of the substrate opposite the first side, comprising a hydrophilic surface to attract moisture,
wherein an ultrasonic pulse generated by a piezoelectric transducer of the array is directed to propagate through the substrate and the contact layer, such that when an object is in contact with the hydrophilic surface of the contact layer, a reflected ultrasonic pulse is produced and propagates through the contact layer and the substrate to be received at the array of piezoelectric transducers, wherein CMOS elements of the CMOS layer in communication with the array of piezoelectric transducers are operable to receive and process outputs from the piezoelectric transducers produced in response to the received reflected ultrasonic pulses.

2. The ultrasonic transceiver sensor device of claim 1, wherein reflected ultrasonic pulses received at the piezoelectric transducers include varying times and amplitudes associated with valleys and peaks of the object in contact with the contact layer that correspond to echo signals of different delays and magnitudes to represent physical features of the object in contact with the ultrasonic transceiver sensor device.

3. The ultrasonic transceiver sensor device of claim 1, further comprising:
a plurality of ridges formed on, or as a part of, the hydrophilic surface of the contact layer to provide a structure that affects at least a time and a direction of the reflected ultrasonic pulse,
wherein the ridges are configured to change in shape based on an applied force by the object, such that reflected ultrasonic pulses received at the piezoelectric transducers are returned from the ridges that correspond to echo signals of different delays and magnitudes corresponding to the applied force.

4. The ultrasonic transceiver sensor device of claim 3, wherein the plurality of ridges facilitate increased resolution of a differential between a generated ultrasonic pulse transmitted toward the object in contact with the plurality of ridges and the reflected ultrasonic pulses received at the piezoelectric transducers are returned from the ridges, such that a type of force, including a normal force, a shear force, or a combination of both, is determinable.

5. The ultrasonic transceiver sensor device of claim 3, wherein the plurality of ridges is structured as a homogenous layer, wherein the ridges have a substantially uniform set of material properties and topology.

6. The ultrasonic transceiver sensor device of claim 3, wherein the plurality of ridges is structured as a heterogeneous layer, wherein the ridges have a varying set of material properties and topology.

7. The ultrasonic transceiver sensor device of claim 1, wherein the CMOS elements of the CMOS layer in communication with the array of piezoelectric transducers are operable to receive and process outputs from the piezoelectric transducers produced in response to the generated ultrasonic pulses transmitted toward the contact layer and the received reflected ultrasonic pulses, such that a thermal property of the object in contact with the surface is determined based on the relative time-of-flight (TOF) of the ultrasonic pulses.

8. The ultrasonic transceiver sensor device of claim 7, wherein the thermal property is determined based on a time-of-flight (TOF) of the ultrasonic pulses transmitted toward the contact layer and the received reflected ultrasonic pulses that corresponds to a temperature profile across (i) the contact layer and the substrate and (ii) the object in contact with the hydrophilic surface.

9. The ultrasonic transceiver sensor device of claim 7, wherein the thermal property of the object is a temperature of a region of the object in contact with the hydrophilic surface.

10. The ultrasonic transceiver sensor device of claim 1, further comprising:
a time-of-flight (TOF) reference block comprising a reference substrate operably coupled to at least one transducer in the array of piezoelectric transducers.

11. The ultrasonic transceiver sensor device of claim 10, further comprising:
at least one heating element coupled to or integrated with the reference substrate to heat the reference substrate, at least one heating element coupled to or integrated with the substrate to heat the substrate, or both at least one heating element coupled to or integrated with the reference substrate to heat the reference substrate and at least one heating element coupled to or integrated with the substrate to heat the substrate.

12. The ultrasonic transceiver sensor device of claim 1, wherein the array of piezoelectric transducers comprises a first piezoelectric transducer and a second piezoelectric transducer, disposed adjacent one another, each of the first piezoelectric transducer and the second piezoelectric transducer being electrically connected to in a data processing unit.

13. An ultrasonic soil sensor configured to characterize constituents in soil, comprising:
a housing;
an ultrasonic transceiver sensor borne on, within or partially within the housing, the ultrasonic transceiver sensor comprising:
a substrate including a semiconductor material;
a CMOS layer attached to a first side of the substrate, the CMOS layer comprising circuit elements;
an array of piezoelectric transducers, communicatively coupled to the circuit elements of the CMOS layer, configured to generate ultrasonic pulses having a frequency of at least 0.5 GHz; and
a contact layer, on a second side of the substrate opposite the first side, comprising a hydrophilic surface,
a processing device; and
a communication device,
wherein the ultrasonic transceiver sensor is borne by the housing with the hydrophilic surface of the contact layer disposed to communicate with an environment external to the housing,
wherein the ultrasonic transceiver sensor is configured to generate an ultrasonic pulse, via one or more piezoelectric transducers of the array of piezoelectric transducers, directed to propagate through the substrate and to the hydrophilic surface of the contact layer to yield a reflected ultrasonic pulse from the hydrophilic surface that propagates through the contact layer and the substrate and to the array of piezoelectric transducers,
wherein the piezoelectric transducers of the array of piezoelectric transducers produce output signals responsive to receipt of the reflected ultrasonic pulse, and
wherein the circuit elements of the CMOS layer are configured to receive the output signals from the piezoelectric transducers producing the output signals, and to transmit the output signals from the piezoelectric transducers to the processing device or to the communication device, or to process the output signals from the piezoelectric transducers producing the output signals prior to transmitting the output signals from the circuit elements to the processing device or to the communication device.

14. The ultrasonic soil sensor of claim 13, wherein the hydrophilic surface of the contact layer comprises nanostructures protruding outwardly from the hydrophilic surface at a height of between about 10 nm to 20 nm.

15. The ultrasonic soil sensor of claim 13, wherein the hydrophilic surface of the contact layer includes a plurality of ridges configured to deform responsive to an applied force and wherein characteristics of reflected ultrasonic pulses returned from the ridges and received at the piezoelectric transducers vary responsive to deformation of one or more of the plurality of ridges.

16. The ultrasonic soil sensor of claim 15,
wherein the plurality of ridges are configured to deform longitudinally to enable determination of via the reflected ultrasonic pulses, at least one characteristic of a normal force acting on one or more of the plurality of ridges,
wherein the plurality of ridges are configured to deform laterally to enable determination of, via the reflected ultrasonic pulses, at least one characteristic of a shear force acting on one or more of the plurality of ridges, or
wherein the plurality of ridges are configured to deform both laterally and longitudinally to enable determination of, via the reflected ultrasonic pulses, at least one characteristic of a normal force and at least one characteristic of a shear force acting on one or more of the plurality of ridges.

17. The ultrasonic soil sensor of claim 13,
wherein the circuit elements of the CMOS layer in communication with the array of piezoelectric transducers are operable to receive and process outputs from the piezoelectric transducers produced in response to the received reflected ultrasonic pulses, and
wherein the circuit elements are configured to determine, alone or together with the processing device, a thermal property of the soil in contact with the hydrophilic surface of the contact layer, a thermal property of an object in the soil in contact with the hydrophilic surface of the contact layer, or both a thermal property of the soil in contact with the hydrophilic surface of the contact layer and a thermal property of an object in the soil in contact with the layer hydrophilic surface, responsive to a time-of-flight (TOF) of the ultrasonic pulses.

18. The ultrasonic soil sensor of claim 17, further comprising a time-of-flight (TOF) reference block including a reference substrate operably coupled to the substrate.

19. The ultrasonic soil sensor of claim 18, further comprising at least one heating element coupled to or integrated with the substrate to heat the substrate.

20. The ultrasonic soil sensor of claim 18, further comprising at least one heating element coupled to or integrated with the reference substrate to heat the reference substrate.

21. The ultrasonic soil sensor of claim 13, wherein the housing includes a rigid elongated body having a first end configured to facilitate insertion into soil, wherein the ultrasonic transceiver sensor borne on, within, or partially within the housing is disposed at a predetermined position along a length of the rigid elongated body to dispose the hydrophilic surface of the contact layer in communication with soil following insertion of the at least the first end of the ultrasonic soil sensor into soil.

22. The ultrasonic soil sensor of claim 21, wherein the communication device comprises a wireless transmitter, a wireless receiver, or a wireless transceiver operable to respectively transmit, receive, or transmit and receive data with a remote external device.

23. The ultrasonic soil sensor of claim 22, further comprising an antenna, operably coupled to the wireless transmitter, the wireless receiver or the wireless transceiver, respectively, the antenna being disposed at a second end of the rigid elongated body opposite the first end of the rigid elongated body.

24. The ultrasonic soil sensor of claim 13, wherein the reflected ultrasonic pulses from the hydrophilic surface of the contact layer enable, via at least one of or both of the circuit elements and the processing device, determination of water content, chemical properties of the soil, root growth, presence of an organism, or characteristics of an organism in the soil proximate the surface of the substrate.

25. The ultrasonic soil sensor of claim 13, further comprising a memory device operably coupled to the circuit elements, to the processor, or to the communication device.

* * * * *